US006458532B1

(12) United States Patent
Detera-Wadleigh et al.

(10) Patent No.: US 6,458,532 B1
(45) Date of Patent: Oct. 1, 2002

(54) POLYNUCLEOTIDES ENCODING IMP.18P MYO-INOSITOL MONOPHOSPHATASE AND METHODS OF DETECTING SAID POLYNUCLEOTIDES

(75) Inventors: Sevilla D. Detera-Wadleigh, Bethesda, MD (US); Takeo Yoshikawa, Rockville, MD (US); Alan R. Sanders, Washington, DC (US); Lisa E. Esterling, Derwood, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/091,952
(22) PCT Filed: Oct. 28, 1997
(86) PCT No.: PCT/US97/19381
§ 371 (c)(1),
(2), (4) Date: Apr. 19, 1999
(87) PCT Pub. No.: WO98/18963
PCT Pub. Date: May 7, 1998

Related U.S. Application Data

(60) Provisional application No. 60/029,278, filed on Oct. 28, 1996.

(51) Int. Cl.[7] .......................... C12Q 1/68; C12P 19/34; C07H 21/04; C12N 15/63; C12N 1/21
(52) U.S. Cl. .......................... 435/6; 435/91.2; 435/21; 435/471; 435/455; 435/196; 435/325; 435/252.3; 435/320.1; 536/23.1; 536/23.5; 536/23.2; 536/24.31; 536/24.33; 514/44
(58) Field of Search ......................... 435/6, 91.2, 21, 435/471, 455, 196, 325, 252.3, 320.1; 536/23.1, 23.5, 23.2, 24.31, 24.33; 514/44

(56) References Cited

U.S. PATENT DOCUMENTS 5,716,806 A * 2/1998 Meissner .................. 435/69.1

FOREIGN PATENT DOCUMENTS

WO 96/08557 * 3/1996

OTHER PUBLICATIONS

McAllister et al. Biochem Journal. 284:749–754, 1992.*
Yoshikawa et al. Molecular Psychiatry. 2:393–397, 1997.*
Coon et al., "Analysis of chromosome 18 DNA markers in multiplex pedigrees with manic depression," *Biological Psychiatry* (1996) 39: 689–696.
Hillier et al., "The WashU–Merk EST Project," (1995) Database GenBank on STN, Accession No. R52482.
Sjoholt et al., "Genomic structure and chromosomal localization of a human myo–isoitol monophosphatase gene (IMPA)," *Genomics* (1997) 45: 113–122.
Stine, "Evidence for linkage of bipolar disorder to chromosome 18 with a parent–of–origin effect," *Am. J. Hum. Genet.* (1995) 57: 1384–1394.

* cited by examiner

*Primary Examiner*—Carla J. Myers
(74) *Attorney, Agent, or Firm*—Townsend and Townsend and Crew LLP

(57) ABSTRACT

Methods and compositions are provided for determining a genotype associated with increased susceptibility to manic-depressive illness. The genotype is determined using markers for a region of chromosome 18 exhibiting linkage disequilibrium with manic-depressive illness. The invention also provides for a novel myo-inositol monophosphatase protein encoded for on chromosome 18.

9 Claims, 8 Drawing Sheets

A 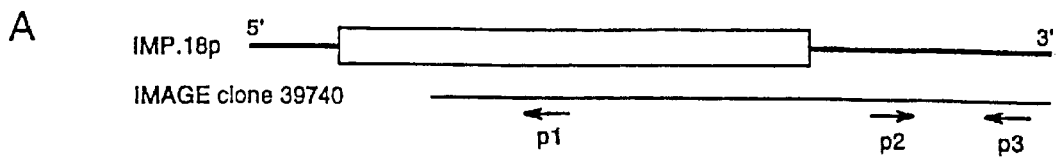

B
```
gtgggacgggcggcggactaggcacagagctgcgggagcaggcacagggagtgtggagcc    60
tggcggcgggacggcgggatccggtgggagccggagtcccgccgagggggggctggaggtg   120
gaggggcccggcgaggccgcg ATGAAGCCGAGCGGCGAGGACCAGGCGGCGCTGGCGGCC   180
                      M  K  P  S  G  E  D  Q  A  A  L  A  A   (13)

GGCCCCTGGGAGGAGTGCTTCCAGGCGGCCGTGCAGCTGGCGCTGCGGGCAGGACAGATC   240
G  P  W  E  E  C  F  Q  A  A  V  Q  L  A  L  R  A  G  Q  I    (33)

ATCAGAAAAGCCCTTACTGAGGAAAAACGTGTCTCAACAAAAACATCAGCTGCAGATCTT   300
I  R  K  A  L  T  E  E  K  R  V  S  T  K  T  S  A  A  D  L    (53)

GTGACAGAAACAGATCACCTTGTGGAAGATTTAATTATTTCTGAGTTGCGAGAGAGGTTT   360
V  T  E  T  D  H  L  V  E  D  L  I  I  S  E  L  R  E  R  F    (73)

CCTTCACACAGGTTCATTGCAGAAGAGGCCGCGGCTTCTGGGGCCAAGTGTGTGCTCACC   420
P  S  H  R  F  I  A  E  E  A  A  A  S  G  A  K  C  V  L  T    (93)

CACAGCCCGACGTGGATCATCGACCCCATCGACGGCACCTGCAATTTTGTGCACAGATTC   480
H  S  P  T  W  I  I  D  P  I  D  G  T  C  N  F  V  H  R  F    (113)

CCGACTGTGGCGGTTAGCATTGGATTTGCTGTTCGACAAGAGCTTGAATTCGGAGTGATT   540
P  T  V  A  V  S  I  G  F  A  V  R  Q  E  L  E  F  G  V  I    (133)

TACCACTGCACAGAGGAGCGGCTGTACACGGGCCGGCGGGGTCGGGGCGCCTTCTGCAAT   600
Y  H  C  T  E  E  R  L  Y  T  G  R  R  G  R  G  A  F  C  N    (153)

GGCCAGCGGCTCCGGGTCTCCGGGGAGACAGATCTCTCAAAGGCCTTGGTTCTGACAGAA   660
G  Q  R  L  R  V  S  G  E  T  D  L  S  K  A  L  V  L  T  E    (173)

ATTGGCCCCAAACGTGACCCTGCGACCCTGAAGCTGTTCCTGAGTAACATGGAGCGGCTG   720
I  G  P  K  R  D  P  A  T  L  K  L  F  L  S  N  M  E  R  L    (193)

CTGCATGCCAAGGCGCATGGGGTCCGAGTGATTGGAAGCTCCACATTGGCACTCTGCCAC   780
L  H  A  K  A  H  G  V  R  V  I  G  S  S  T  L  A  L  C  H    (213)

CTGGCCTCAGGGGCCGCGGATGCCTATTACCAGTTTGGCCTGCACTGCTGGGATCTGGCG   840
L  A  S  G  A  A  D  A  Y  Y  Q  F  G  L  H  C  W  D  L  A    (233)

GCTGCCACAGTCATCATCAGAGAAGCAGGCGGCATCGTGATAGACACTTCGGGTGGACCC   900
A  A  T  V  I  I  R  E  A  G  G  I  V  I  D  T  S  G  G  P    (253)

CTCGACCTCATGGCTTGCAGAGTGGTTGCGGCCAGCACCCGGGAGATGGCGATGCTCATA   960
L  D  L  M  A  C  R  V  V  A  A  S  T  R  E  M  A  M  L  I    (273)

GCTCAGGCCTTACAGACCATTAACTATGGGCGGGATGATGAGAAGTGA ctgcggctgagg  1020
A  Q  A  L  Q  T  I  N  Y  G  R  D  D  E  K  *                 (288)

caaagctgctcccaaggcctccctgggctgctgtgggctcctggggaggtggccctcgtg  1080
gcccacgctccatgccagtggctcacgctctgctcctggctaccccagagggagttgtca  1140
cgctacagtgagtggctggccttttaaatcgacgtctctctcaccaggatttggtgttta  1200
gctgtttctctcttttaatctcacgtagccttttttcaggttagtacgtgttcttctgtcag  1260
ggccaaaactcaaatctcctgtgaaatacgtattgataatccaatcttgattttccccc   1320
cagaatataaatctcaggtaataaggctttagaactgctgataaagcggatcgttctcag  1380
gccctcccccggagtacttcagaatgc aataaatcaaaataatgggcaaaaaaaaaaa   1440
aaaaaaa                                                       1447
```

FIG. 5

```
                    10        20         30         40         50        60
IMP.18p  MKPSGEDQAALAAGPWEECFQ-AAVQLALRAGQIIRKALTEEKRVSTKTS--AADLVTETDHL
Xen IMP         MEDR.Q..MDFL..SI.RK..SVVCA..K.DVSIMV..LAP...A..QK
Bov IMP         M.D..Q..MD-Y..T..GQ..EVV.E..KN.MNIMV.S--P......A..QK
Hum IMP         M.D..Q..MD-Y..T..RQ..EVVCE.IKN.MN.ML.S..PV.....A..QK
Rat IMP         M.D..Q..MD-Y..T..RQ..EVVCE.IKN.MN.ML.S..PV.....A..QK 70        80        90        100       110       120
IMP.18p  VEDLIISELRERFPSHRFIAEEAAASGAKCVLTHSPTWIIDPIDGTCNFVHRFPTVAVSI
Xen IMP  ..EM...SIK.KY...S..G..SV.A..GST..DN...........T.........
Bov IMP  ..KML.TSIK.KY...S..G..SV.A.E.SI..DN...........T........F.
Hum IMP  ..KML..SIK.KY...S..G..SV.A.E.SI..DN...........T........F.
Rat IMP  ..KML..SIK.KY...S..G..SV.A.E.SI..DN...........T........F.
                                                          └─ motif A ─┐

130       140       150       160       170       180
IMP.18p  GFAVRQELEFGVIYHCTEERLYTGRRGRGAFCNGQRLRVSGETDLSKALVLTEIGPKRDP
Xen IMP  ....HKQV....V.S.V.DKM...K.K.S.....K.Q...IT.SMII..L.SN.N.
Bov IMP  ....HKQV....V.S.V.DKM...K.K.......K.Q...HQE.IT.S.LV..L.SS.T.
Hum IMP  ..V.NKKM...IV.S.L.DKM...K.K.......K.Q...QQE.IT.S.LV..L.SS.T.
Hum IMP  ....NKKI....V.S.V.GKM...A.K.......K.Q...QQE.IT.S.LV..L.SS.T.
Rat IMP  ....NKKI....V.S.V.GKM...A.K.......K.Q...QQE.IT.S.LV..L.SS.T.

190       200       210       220       230       240
IMP.18p  ATLK-LFLSNMERLLHAKAHGVRVIGSSTLALCHLASGAADAYYQFGLHCWDLAAATVIIR
Xen IMP  EFI.TVS.......CIPI..I.AV.TAAVNM.LV.T.G....EM.....M..S..VT
Bov IMP  E.VR-II....I....CLPI..I.GV.TAA.NM.LV.A......EM.I....V.G.I.VT
Hum IMP  E.VR-MV.....K.FCIPV..I.SV.TAAVNM.LV.T.G.....EM.I....V.G.I.VT
Rat IMP  E.VR-MV.....K.FCIPV..I.SV.TAAVNM.LV.T.G.....EM.I....V.G.I.VT
                                                              └─ motif B ─┐

250       260       270       280    288
IMP.18p  EAGGIVIDTSGGPLDLMACRVVAASTREMAMLIAQALQTINYGRDDEK
Xen IMP  ....TIL.AT..LF...S..IIS..S..I.ER..KE..I.PLE...G.STNS
Bov IMP  ....VLL.VT...F..SR..I.S.NKTL.ER..KEI.I.PLQ....D
Hum IMP  ....VLM.VT...F..SR..I...NN.IL.ER..KEI.V.PLQ....D
Hum IMP  ....VLM.VT...F..SR..I..NN.IL8ER..KEI.V.PLQ....S
Rat IMP  ....VLM.VT...F..SR..I..NN.IL8ER..KEI.V.PLQ....S
```

FIG. 6

```
-1032 gtccagccgctgtcctcgcagtgtttggggttagcggagggagagct tgt
                                                    HNF
 -982 ttgcgaccaaacttgccgcgcg gggcgg ccgcttgcaggaacactgcggc
       -5                      Sp1
 -932 cttgtgcgctcggcggtctgagctcct gcgaggcc gagaacgacgcctag
                                    AP2
 -882 cgcccagcggcctccgcgaacaaaaagcgaccggtcggaaggtgctggcc -832 cagccgcccctggcgctcgagcccgaatccggccacagaccatgaaggga -782 cgcccggcac cacgtg cgcggggatccgcggacgggacgctccccggcac
                 E-box
 -732 ctccggggctgggccggcaccgcacggtcccacccagacagtagctg ccc
                                                      AP2
 -682 cgggc cccaaaacagccgttcctagctcctccctcccagtttctgcggt -632 ggcccaag ccgccctccg cgcgcttgacccagaacagtacggagttctgc
               AP2
 -582 acgagccgggggtggggcctgtctcagcgcgcggcggt gggcggggc tt
                                                 Sp1
 -532 ggacacgggcccggctcaacttgagg gaggcggggc tcgaggctcagagg
                                    Sp1
 -482 agttggagcccgctctgcgcgctgcgggacggggcacggcggagcagggt -432 tgggtccgcctcgagcggggagggtgatgctgcaccaca gggcggggc t
                                                 SP1
 -382 ggaggtaaagcgcggagcggagagggaccaggctcggcactgatttgtgt -332 tca gggctagccc aga gggcggggc caggtacggggcgcagccgggagc
         p53            Sp1
 -282 gggag gggcgg tgcaggacggggccgggcacggcgcgggaa gaggcc agg
          Sp1                                         t-antigen
 -232 agcagcaacgggtgcg gggcggggc cgggagcgtcaag gggcgg gaaga
                        Sp1                      Sp1
 -182 gggggg aat gggcggggcc gagctctgcgaggggcgaggtggggaatgca
                 Sp1
 -132 gagcggggcc ggacgcgggagcagggagct gggcgg ggagcg gggcgg gg
        GCF                           Sp1         Sp1
  -82 agctgggctgggctcggcac gggcgggc ggagggtggggagcggaaag
                             Sp1           ⟶
  -32 caggacgcgcggctcccgcggcccgc TGGCTGCCCTTC CCGCCAGCGC AG
                                                 AP2
  +19 GTGTGGGAC GGGCGG CGGACTAGGCACAGAGCTGCGGGAGCAGGCACAGG
                Sp1
  +69 GAGTGTGGAGCCTGGCGGCGGGACGGCGGGTCCGGTGGGAGCCGGAGTCC
 +119 CGCCGAGGGGGGCTGGAGGTGGAGGGGCCCGGCGAGGCCGCGATGAAGCC
 +169 GAGCGGCGAGGACCA                                    p
```

POLYNUCLEOTIDES ENCODING IMP.18P MYO-INOSITOL MONOPHOSPHATASE AND METHODS OF DETECTING SAID POLYNUCLEOTIDES

CROSS REFERENCE TO RELATED APPLICATIONS

The present application is the National Stage of International Application No. PCT/US97/19381, filed Oct. 28, 1997, which claims the priority benefit of U.S. Provisional Application No. 60/029,278, filed Oct. 28, 1996.

FIELD OF THE INVENTION

The present invention relates to compositions and methods for determining the genotype associated with an increased or decreased susceptibility to manic-depressive illness. The invention also provides a means to determine an individual's increased or decreased risk of developing manic-depressive illness.

BACKGROUND OF THE INVENTION

Genome screening efforts by several groups, designed to identify regions linked to bipolar disorder, have revealed evidence for potential susceptibility loci on chromosome 18. Berrettini (1994) *Proc Natl Acad Sci USA* 91:5918–5921, reported evidence for a susceptibility locus in the pericentromeric region of the chromosome. In a subsequent study on an independent pedigree series, Stine (1995) *Am. J. Hum. Genet.* 57:1384–1394, found support for the prior hypothesis on 18p (Berrettini et al., *Proc Natl Acad. Sci. USA*, 91:5918–5921, 1994). In the same study, Stine (1995) supra, presented evidence for a possible additional linkage on 18q. Recently, Freimer (1996) *Nature Genet.* 12:436–441, proposed a predisposing locus close to the telomere of 18q in Costa Rican kindreds. These reports suggest that the regions potentially implicated in bipolar disorder encompass a very large portion of chromosome 18.

In addition to bipolar disorder, more than 25 other diseases have been localized to chromosome 18, approximately 80% of which still await the discovery of the underlying defective gene (Overhauser et al., *Cytogenet Cell Gene*, 71:106–117, 1995; Online Mendelian Inheritance in Man (OMIM) (TM). (Database on line. 1995; URL: http://www3.ncbi.nlm.nih.gov/omim/. cited Jan. 19, 1996)). Since this chromosome has a genetic length estimated to be 150 cM [Cooperative Human Linkage Center (CHLC), *Science* 265:2049–2054, 1994], which includes about 4.5% of the total length of the genome, it is expected to encode several thousand genes. Approximately 40 genes have been mapped to this chromosome [Overhauser et al., 1995; Genome Database (GDB), URL: http.//gdbwww.gdb.org/gdb/browser/docs/topq.html>[database online]. (1990-). Updated daily (cited Jan. 19, 1996]; OMIM, [Database on line. 1995; cited Jan. 19, 1996]. Between 1993 and 1995, only 14 genes have been added to the list of chromosome 18 genes (Geurts van Kessel et al., *Cytogenet Cell Gene*, 65:141–165, 1994; Overhauser et al., *Cytogenet Cell Gene*, 71:106–117, 1995). Therefore, a dense transcriptional map, which would be valuable in positional cloning of susceptibility genes, remains to be developed for chromosome 18.

SUMMARY OF THE INVENTION

In one aspect the present invention is directed to a method for determining a genotype associated with increased susceptibility to manic-depressive illness. The method comprises determining the genotype of an affected individual with at least one polymorphic marker localized within the chromosomal region defined by and including markers D18S843 and D18S869, and determining therefrom the genotype associated with increased susceptibility to manic-depressive disorder.

In preferred embodiments the polymorphic marker is amplified by primers which selectively hybridize, under stringent conditions, to the same nucleic acid sequences as primers of SEQ ID NO:1 and SEQ ID NO:2 (see Table 1, below, forward and reverse primers to amplify Clone 22). Typically the polymorphic marker is amplified by the polymerase chain reaction.

In other embodiments the method of further comprises determining the genotype of a tested individual wherein the genotype is determined with at least one polymorphic marker localized within the chromosomal region defined by and including markers D18S843 and D18S869. The genotype of the tested individual is compared to the genotype associated with increased susceptibility to manic-depressive illness and the increased or decreased risk of the tested individual developing manic-depressive illness is

TABLE 1

PCR PRIMER SEQUENCES

| Name | Primers | SEQ ID NO: | Name | Primers | SEQ ID NO: |
|---|---|---|---|---|---|
| Clone 22 | F-TACAAAAGAGGACAAAGCAC | 30 | D18S73 | F-TGCCACTGCAACAATGC | 31 |
|  | R-GGTGCCTGTATATAAGTTGA | 32 |  | R-CCCAGCAATCAACCTTTAAG | 33 |
| Clone 24 | F-CTACAGAATAGAATACATGGCG | 34 | D18S869 | F-TGTTTATTTGTTTGACTCAATGG | 35 |
|  | R-GAGCTCTGAACTGTATTCAGA | 36 |  | R-GAGTGAATGCTGTACAAACAGC | 37 |
| Clone 29 | F-TCTCAGCTTACTCAACCT | 38 | D18S996 | F-GATGGAAAGCCATTTTATTTTC | 39 |
|  | R-GATGAGGTGGAACAATCAC | 40 |  | R-TCGTACTATGAAATTTTTAAGCCTT | 41 |
| GNAL | F-GGTCTGTACAGTGTAATAAACC | 42 | FB14A10 | F-CCTTCCCCTCTATTCTCAAA | 43 |
|  | R-CTACTGCAAAATGTGTCCTGTC | 44 |  | R-GAGCGAGACTGTCTCAAAAA | 45 |
| Clone 37 | F-CACATTAGCCAGTCTGATAAAG | 46 | GC32001 | F-GAGTTGTGGGGGGAATAGT | 47 |
|  | R-AAGTTACACACAGTAGCTGA | 48 |  | R-ATACGGAGGTTGAACTAGGAAGG | 49 |
| AFMa058yg5 | F-TAGATGCTATATTAGGCTGGGTCTC | 50 | GP4B15 | F-CGGTTCTGGATTTATCAGTA | 51 |
|  | R-GAACTTACAGCACTGGCTCTCC | 52 |  | R-AGGGTTGCAATGAGCTGAG | 53 |
| AFMa152wg9 | F-AAGAACAAAAGGTCACCTGTCA | 54 | IB-1114 | F-GCCACACACAAATTTTTCTC | 55 |
|  | R-TGTCTCACCTCTGCTCACTCAT | 56 |  | R-ACAGGGTGTAAGAGGAGAGG | 57 |
| CHLC.GGA16G02 | F-ATGGAAGGAAAAACAGAGGG | 58 | NIB-1802 | F-CTGATCACATTTCATACAGC | 59 |
|  | R-GAACTCTTCAAGAGGGGAGC | 60 |  | R-TGTATGTGGGCTTAACTGTT | 61 |

TABLE 1-continued

PCR PRIMER SEQUENCES

| Name | Primers | SEQ ID NO: | Name | Primers | SEQ ID NO: |
|---|---|---|---|---|---|
| D18S1114 | F-ATCAGTATAATGATGGATGAATCAC | 62 | SGC-31363 | F-CTACTGGGAGGTAGGTAATCTCAG | 63 |
|  | R-TGAGGCAAGAGGGTCAC | 64 |  | R-GCAAAACCAACCACATCAAA | 65 |
| D18S1116 | F-TCTGCCACTTTTTATGGG | 66 | SGC34207 | F-GATCCTGTTCTTTCAGCAGG | 67 |
|  | R-CAATGTTTTAACTTCTAGGACAAAT | 68 |  | R-TTTAACCAGCTGGAGTGAAGG | 69 |
| D18S1150 | F-GGCACAGGAAACGTGAAT | 70 | WI-11680 | F-ACAGATACTTTTCCACGCAACA | 71 |
|  | R-CACAAGGATGCCAGCC | 72 |  | R-AAAAAGATGTACGGTCTGGCC | 73 |
| D18S1153 | F-ATGGAGGCTCTGAGACCCTT | 74 | WI-13171 | F-TTTTATTTGGACAAGAGAACTTGTG | 75 |
|  | R-CTTGCCTGATGCCTGAAAT | 76 |  | R-ATGATCAGCTCTGAGGTGCA | 77 |
| D18S1158 | F-GCATCTATGCAGTGCCAAAT | 78 | WI-18080 | F-TGGCATAAAGTTTGCAAATATCA | 79 |
|  | R-TCATTAGCAACAAGGATCTCC | 80 |  | R-ATACACCAAAGGAGAAGGATTAACA | 81 |
| D18S1228 | F-AGACAGTTGAAAAGGACACAAATG | 82 | D18S1066 | F-TGCTGTTGCCTCTCAGCATCTC | 83 |
|  | R-TGGTGATGGGACTTTTCAAA | 84 |  | R-CACCTTTCAAGTGCTTGGCAGTC | 85 |
| D18S378 | F-AGCCTGGGTGACAGAGCAA | 86 | D18S1215 | F-GTTTGCTGCATCTCCCAATT | 87 |
|  | R-ACAGGGAAAGCTGGGGGAT | 88 |  | R-GTGCCCACATTGTTGTGAAG | 89 |
| D18S40 | F-CAAGATAGATGCATTTTCCAGT | 90 | D18S1299 | F-TTTAAGCCTCAAGGGACCCT | 91 |
|  | R-CATCCAAAGGGTGAATGTGT | 92 |  | R-AGATTGAGGACCAGGTGGTG | 93 |
| D18S464 | F-GCCAGACTTTGTGCCATTTC | 94 | D18S1226 | F-CTCTTAAGTTGAGTGAAGTGGAAGC | 95 |
|  | R-TTTCCTGAATCTCTTGTGGTTTG | 96 |  | R-CGCAAAAGTCAGGAAAGAGG | 97 |
| D18S482 | F-ATGAGTGAATGCCAACTTCG | 98 | SHGC-32282 | F-TTACGCATTTTGTATCAGACTTACA | 99 |
|  | R-CCTGGCTGACAGAGTGAGT | 100 |  | R-GGTGGAGTATCAGAAGTGATTTTAG | 101 |
| D18S53 | F-GGTCACCTACAACTTTGGATG | 102 | D18S1315 | F-TGGACTTCTACCCCCATCTG | 103 |
|  | R-TGCATGTAAATATCAGAGTCTGTT | 104 |  | R-TTTGAAACCTGGACACTTTGG | 105 |
| D18S71 | F-ACCCGCTCAAAAGCCT | 106 | D18S843 | F-GTCCTCATCTGTAAAACGGG | 107 |
|  | R-TTAATGGATTATCAAGAGTGGTTCT | 108 |  | R-CCACTAACTAGTTTGTGACTTTGG | 109 | determined therefrom. Generally, the polymorphic marker of the tested individual is amplified by primers which selectively hybridize, under stringent conditions, to the same nucleic acid sequences as primers of SEQ ID NO:1 and SEQ ID NO:2.

In another aspect, the present invention is directed to a nucleic acid composition comprising oligonucleotide primers which selectively hybridize, under stringent conditions, to the same nucleic acid sequence as primers of SEQ ID NO:1 and SEQ ID NO:2. In an additional aspect the present invention is directed to a nucleic acid of less than 10 kB and comprising a polymorphic marker amplified by oligonucleotide primers of SEQ ID NO:1 and SEQ ID NO:2.

In yet another aspect, the present invention is directed to a method for determining an increased susceptibility to manic-depressive illness in an individual, comprising determining the genotype of the individual with oligonucleotide primers. The oligonucleotide primers amplify a polymorphic site as primers of SEQ ID NO:1 and SEQ ID NO:2. This polymorphic marker can be found in at least two forms, designated as "allele 1" of clone 22 (SEQ ID NO:14) or "allele 2" of clone 22 (SEQ ID NO:15). The presence of allele 2 of the polymorphic marker indicates an increased susceptibility to manic-depressive illness.

The invention further provides for a isolated nucleic acid encoding an IMP.18p myo-inositol monophosphatase, the protein defined as having a calculated molecular weight of between about 22 to 34 kDa, and where the protein's activity includes hydrolysis of myo-inositol 1-phosphate to generate inositol and inorganic phosphate; and where the protein specifically binds to an antibody raised against an IMP.18p myo-inositol monophosphatase protein, or immunogenic fragment thereof, consisting of SEQ ID NO:17; or, having at least 60% amino acid sequence identity to an IMP.18p myo-inositol monophosphatase protein consisting of SEQ ID NO:17, as measured using a sequence comparison algorithm. In one embodiment, the nucleic acid encodes a IMP.18p myo-inositol monophosphatase having a calculated molecular weight of about 28 to 29 kDa. In other embodiments, the isolated nucleic acid: encodes a protein which has at least 80% amino acid sequence identity to the IMP.18p myo-inositol monophosphatase protein of SEQ ID NO:17, as measured using a sequence comparison algorithm; encodes a protein having the sequence set forth in SEQ ID NO:17; specifically hybridizes to SEQ ID NO:16 under stringent conditions; or, encodes an IMP.18p myo-inositol monophosphatase protein which specifically binds to an antibody directed against a protein having a sequence as set forth in SEQ ID NO:17.

In further embodiments, the invention also provides for a polynucleotide or fragment thereof comprising a purified antisense nucleotide capable of hybridizing to and having a nucleic acid sequence complementary to at least a portion of an IMP.18p myo-inositol monophosphatase polynucleotide. The invention also provides for an expression vector comprising a nucleic acid encoding an IMP.18p myo-inositol monophosphatase or its antisense sequence. Further embodiments provide for a cell comprising an exogenous nucleic acid sequence encoding an IMP.18p myo-inositol monophosphatase protein. Another embodiment provides for an organism into which an exogenous nucleic acid sequence which specifically hybridizes under stringent conditions to SEQ ID NO:16 or which comprises a nucleic acid encoding an IMP.18p myo-inositol monophosphatase or fragment thereof, has been introduced, and the organism expresses the exogenous nucleic acid as an IMP.18p myo-inositol monophosphatase protein, or fragment thereof. In one embodiment, the organism's exogenous nucleic acid sequence is translated into an IMP.18p myo-inositol monophosphatase protein which is expressed externally from the organism.

The invention also provides for an isolated IMP.18p myo-inositol monophosphatase protein having a calculated molecular weight of about 22 to 34 kDa; where the protein's activity includes hydrolysis of myo-inositol 1-phosphate to generate inositol and inorganic phosphate; and specifically binds to an antibody raised against a myo-inositol monophosphatase protein, or immunogenic fragment thereof, consisting of SEQ ID NO:17, or has at least 60% amino acid sequence identity to a myo-inositol monophosphatase protein consisting of SEQ ID NO:17, as measured using a sequence comparison algorithm. In one embodiment, the isolated IMP.18p myo-inositol monophosphatase protein can also be found in humans. In further embodiments, the isolated IMP.18p myo-inositol monophosphatase protein has a calculated molecular weight of about 28 to 29 kDa; or, has a sequence as set forth in SEQ ID NO:17.

The invention further provides for an isolated antibody which is specifically immunoreactive under immunologically reactive conditions to an IMP.18p myo-inositol monophosphatase protein having the sequence as set forth in SEQ ID NO:17. In another embodiment, the isolated antibody is specifically immunoreactive under immunologically reactive conditions to an IMP.18p myo-inositol monophosphatase protein encoded by a IMP.18p myo-inositol monophosphatase nucleic acid of the invention.

Also provided for in the invention is a pharmaceutical composition comprising an acceptable carrier and an IMP.18p myo-inositol monophosphatase protein; an anti-IMP.18p myo-inositol monophosphatase antibody or binding fragment thereof; or a polynucleotide encoding an IMP.18p myo-inositol monophosphatase protein.

The invention also provides for a method for quantifying the amount of a myo-inositol monophosphatase in a mammal, comprising: obtaining a cell or tissue sample from the mammal; and, determining the amount of an IMP.18p myo-inositol monophosphatase gene product in the cell or tissue.

Another embodiment provides for a method for detecting the presence of a polynucleotide sequence encoding at least a portion of an IMP.18p myo-inositol monophosphatase in a biological sample, comprising the steps of providing a biological sample suspected of containing a IMP.18p myo-inositol monophosphatase-encoding nucleic acid and a probe capable of hybridizing to at least a portion of an IMP.18p myo-inositol monophosphatase nucleotide sequence, or a fragment thereof, from a biological sample; then combining the nucleic acid-containing biological sample with the probe under conditions such that a hybridization complex is formed between the nucleic acid and the probe; and detecting the hybridization complex. In one embodiment the nucleic acid in the biological sample is ribonucleic acid. In another embodiment, the detected hybridization complex correlates with expression of an IMP.18p myo-inositol monophosphatase in the biological sample.

The invention also provides for a method of determining whether a test compound is a modulator of an IMP.18p myo-inositol monophosphatase activity, the method comprising the steps of: providing a composition comprising an IMP.18p myo-inositol monophosphatase protein; contacting the monophosphatase with the test compound; and measuring the activity of the monophosphatase, wherein a change in monophosphatase activity in the presence of the test compound is an indicator of whether the test compound modulates monophosphatase activity. In one embodiment, the composition comprises monophosphatase is encoded a an IMP.18p myo-inositol monophosphatase polypeptide of the invention. In further embodiments, the composition comprises a cell or an organism.

BRIEF DESCRIPTION OF THE FIGURES

FIGS. 4A, 4B, and 4C show hybridization in: fetal brain, lung, liver and kidney; adult heart, brain, lung, liver, skeletal muscle, kidney, and pancreas; and, adult brain amygdala, caudate nucleus, corpus callosum, hippocampus, hypothalamus, substantia nigra, subthalamic nucleus, and thalamus. Control hybridizations with a GAPDH probe are also shown.

FIG. 5B shows the complete 1447 base pair full-length cDNA nucleotide sequence (SEQ ID NO:16) and the corresponding predicted amino acid sequence (SEQ ID NO:17) of the novel IMP.18p of the invention. FIG. 5A shows a schematic representation of this newly discovered message aligned with clone #39740 (IMAGE Consortium).

FIG. 6 shows the alignment of the deduced amino acid sequence of IMP.18p (SEQ ID NO:17) with other IMPs and protein motifs (Xenopus (Xen)=SEQ ID NO:25; bovine (Bov)=SEQ ID NO:27; human (Hum)=SEQ ID NO:28; rat (Rat)=SEQ ID NO:26) characteristic of the myo-inositol monophosphatase protein family.

FIG. 8 shows the promoter sequence for IMP.18p (SEQ ID NO:29).

DETAILED DESCRIPTION OF THE INVENTION

Figure 1:
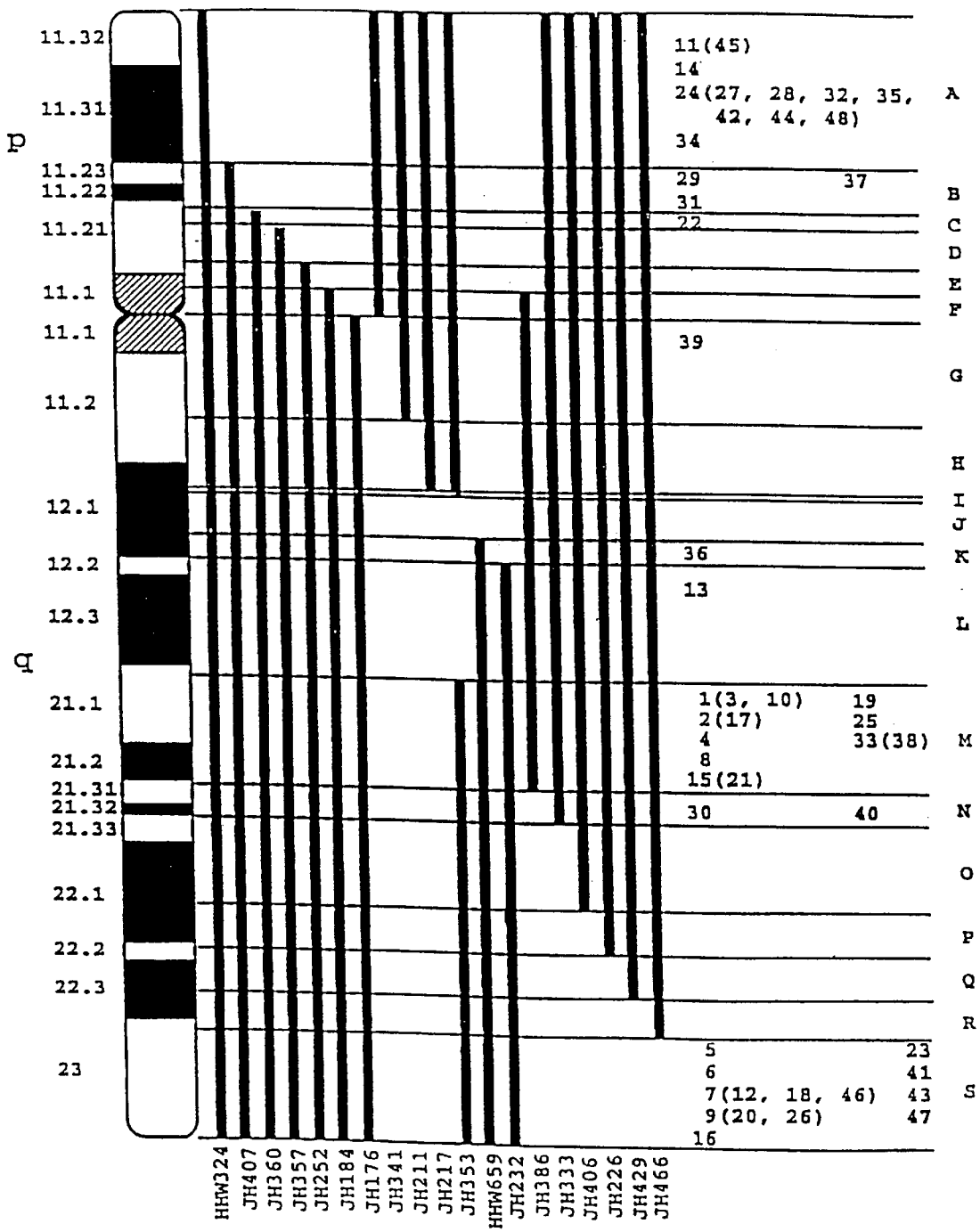
FIG. 1 shows the assignment of brain transcripts to chromosome 18 cytogenetic bins. cDNA selection yielded a total of 48 brain-expressed transcripts (numbered 1 to 48) that mapped specifically to the indicated regions of chromosome 18. Redundant transcripts are in parenthesis next to the first member of each redundant group. The somatic cell hybrids that subdivide the chromosome into cytogenetic bins (represented by A to S, from pter to qter, right hand side) and the names of the cell lines (bottom) are indicated.

In the present invention, a region of chromosome 18 has been identified that is tightly linked to a locus associated with susceptibility to manic-depressive illness, including affective disorders. Linkage disequilibrium between a particular form of a marker in the population and the presence of the manic-depressive illness provides a means to determine the increased susceptibility of an individual to manic-depressive illness. Accordingly, the methods and compositions of the present invention provide a means to alert clinicians to a genetic predisposition towards developing manic-depressive illness. The methods of the invention are useful in genetic counseling of individuals from families affected with manic-depressive illness, and aid in the differential diagnosis of manic-depressive illness from other psychiatric pathologies.

A susceptibility region for bipolar disorder has been found on the pericentromeric portion of chromosome 18 (Berrettini (1994) *Proc. Natl. Acad. Sci. USA* 91:5918–5924). The invention provides the novel discovery that genes and markers corresponding to bipolar disease map to the region of chromosome 18 designated region 18p11.2. This finding led to the discovery of a novel gene encoded in 18p11.2 whose chromosomal location is linked with bipolar disorder, as described in Example 13.

This novel, full-length cDNA, designated IMP.18p (alternatively designated IMPA2), was isolated and sequenced (SEQ ID NO:16, see FIG. 5B), as described in Example 13. Its predicted polypeptide translation product is 288 amino acids (SEQ ID NO:17, see FIG. 5B). The deduced amino acid sequence revealed approximately 54% sequence identity with a human brain myo-inositol monophosphatase (IMP), as described by McAllister, (1992) *Biochem J.* 284:749–754, GenBank Accession #P29218 (also designated IMPA1). The IMP.18p sequence also included motifs characteristic of other IMP proteins (as described in detail below). Thus, the IMP.18p of the invention is a novel myo-inositol monophosphatase (IMP) protein.

The invention also provides for novel anti-IMP.18p reagents in the form of anti-IMP.18p antibodies and IMP.18p-encoding nucleic acids to identify polymorphic variants of IMP.18p within the scope of the claimed invention. Use these novel reagents in various antibody-based and nucleic acid-based assays to clearly describe the identification and isolation of such polymorphic variants are described below.

To provide a more precise location of this gene, mapping with a panel of radiation hybrids (RH) was conducted. Multipoint RH analysis placed the gene between GNAL and D18S71 within the 18p11.2 region (see FIG. 3). Thus, IMP.18p is a gene localized within the chromosomal region defined by and including markers D18S843 and D18S869. Because of the physical position of IMP.18p coding sequence on chromosome 18 and its potential function, IMP.18p is an important gene for the treatment and diagnosis of manic depressive illnesses, including bipolar disorder.

Lithium is the most commonly prescribed medication and effective treatment for manic depression/bipolar disorder. Its therapeutic action is in part mediated through the inhibition of IMP, an enzyme which has a crucial role in the phosphatidylinositol signaling pathway (reviewed in Atack (1996) "Inositol monophosphatase, the putative therapeutic target for lithium," *Brain Res. Rev.* 22:183–190; see also Ragan (1988) *Biochem J.* 249:143–149). IMP is a homodimer, with each subunit organized in an alpha beta alpha beta alpha arrangement of alpha-helices and beta-sheets. This type of structure seems crucial to a two-metal catalyzed mechanism. Lithium appears to inhibit the IMP enzyme following substrate hydrolysis by occupying the second metal binding site before a phosphate group can dissociate from its interaction with the first metal site.

As IMP is a molecular target for the therapeutic effects of lithium, inhibitors of IMP can be lithium-mimetics. Thus, the novel IMP.18p of the invention, which is distantly related to inositol monophosphatase enzymes, can be used to not only to identify inhibitors specific for IMP.18p, but also as a novel means to identify and isolate new inhibitors of IMPs as alternatives to lithium.

In disease states associated with increased levels of IMP activity, such as bipolar disease, the enzymatic activity and levels of IMP.18p is altered in specific brain areas. Thus, the IMP.18p nucleic acid sequence of the invention provides for novel means to measure levels of IMP and diagnose the corresponding disease state.

Because of the location and function of IMP.18p, it qualifies as a novel target for diagnosis, therapeutics and molecular scanning, i.e., identification of mutations, polymorphisms and further members of this new myo-inositol monophosphatase enzyme family.

Definitions

Units, prefixes, and symbols can be denoted in their SI accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention which can be had by reference to the specification as a whole. Accordingly, the terms defined immediately below are more fully defined by reference to the specification in its entirety.

As used herein, "manic-depressive illness" and bipolar disorder, including bipolar I (BPI) and bipolar II (BPII), refer to the same phenotype and can be used interchangeably. Manic depressive disorder includes reference to schizoaffective disorder, or recurrent Major Depressive Illness (i.e., recurrent unipolar illness). See, "Research Diagnostic Criteria," Spitzer et al., *Arch. Gen. Psychiat.*, 35:773–779 (1978); Endicott, J. and Spitzer, L., *Arch. Gen. Psychiat.*, 35:837–862 (1978); and, Diagnostic and Statistical Manual of Mental Disorders III-R, (1980), American Psychiatric Association, Washington D.C., Spitzer and Williams (ed.), each of which is incorporated herein by reference. An individual affected by manic-depressive illness is an "affected individual."

As used herein, "marker" includes reference to a locus on a chromosome that serves to identify a unique position on the chromosome. A "polymorphic marker" includes reference to a marker which can appear in multiple forms, i.e, these different forms sometimes referred to as "alleles" (alleles are defined as different variations of a gene or marker). Different forms of the marker can be used to follow their transmission from parent to child and throughout generations (when they are present in a homologous pair, allow transmission of each of the chromosomes in that pair to be followed).

A genotype may be defined by use of a single or a plurality of markers.

As used herein, "chromosomal region" includes reference to a length of chromosome which may be measured by reference to the linear segment of DNA which it comprises. The chromosomal region can be defined by reference to two unique DNA sequences, i.e., markers.

As used herein, "genotype associated with increased susceptibility to manic-depressive illness" includes reference to a genotype which has a higher probability of occurrence in a manic-depressive illness affected individual than in members of the general United States population who are past the age of onset but unaffected by manic-depressive illness.

As used herein, "increased" means greater than that of the U.S. population average. Thus, an increased susceptibility to manic-depressive illness includes reference to a greater risk of developing manic-depressive illness than the average risk for the U.S. population.

As used herein, "decreased" means less than that of the U.S. population average. Thus, a decreased susceptibility to manic-depressive illness includes reference to a lesser risk of developing manic-depressive illness than the average risk for the U.S. population.

As used herein, "determining" the "risk of the tested individual developing familial manic-depressive illness"

means ascertaining the probability of the tested individual developing manic-depressive illness after the individual reaches the age of onset. The determination of risk may be a quantitatively assessed or may be assessed qualitatively as higher, lower, or equivalent to the average risk to the U.S. population.

As used herein, "tested individual" includes reference to a human whose genotype is being determined. The tested individual may be pre- or postpartum.

As used herein, "localized within the chromosomal region defined by and including" with respect to particular markers includes reference to a contiguous length of a chromosome delimited by and including the stated markers.

As used herein, "manic-depressive illness genotype" includes reference to a genotype determined with at least one polymorphic marker within the chromosomal region defined by markers linked to the locus associated with susceptibility to manic-depressive illness. Preferably, the genotype is determined using polymorphic markers within 5 centimorgans of the polymorphic marker defined by SEQ ID NO:1 and SEQ ID NO:2. In a preferred embodiment, the chromosomal region is defined (flanked) by and includes chromosomal markers D18S843 and D18S869. In a particularly preferred embodiment, the genotype is determined using the marker amplified by oligonucleotide primers of SEQ ID NO:1 and SEQ ID NO:2 (Table 1).

As used herein, "isolated," "purified" or "biologically pure" refer to material which is substantially or essentially free from components which normally accompany or interact with it as found in its naturally occurring environment. The isolated material optionally comprises material not found with the material in its natural environment. Purity and homogeneity are typically determined using analytical chemistry techniques, e.g., sequence analysis, gel electrophoresis or high performance liquid chromatography (HPLC). A protein that is the predominant species present in a preparation is substantially purified. In particular, an isolated IMP.18p or clone 22 nucleic acid is separated from open reading frames which flank the IMP.18p or clone 22 gene and encode proteins other than IMP.18p or clone 22. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

As used herein, "nucleic acid," "polynucleotide," or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (see Batzer et al., *Nucleic Acid Res.* 19:5081 (1991); Ohtsuka et al., *J. Biol. Chem.* 260:2605–2608 (1985); Cassol et al., 1992; Rossolini et al., *Mol. Cell. Probes* 8:91–98 (1994)). The term encompasses nucleic acids, i.e., oligonucleotides, containing known analogues of natural nucleotides which have similar or improved binding properties, for the purposes desired. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphor-amidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, A Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923–1937; Antisense Research and Applications (1993, CRC Press) in its entirety and specifically Chapter 15, by Sanghvi, entitled "Heterocyclic base modifications in nucleic acids and their applications in antisense oligonucleotides." PNAs contain nonionic backbones, such as N-(2-aminoethyl) glycine units. Phosphorothioate linkages are described in WO 97/03211; WO 96/39154; Mata (1997) *Toxicol Appl Pharmacol* 144:189–197. Other synthetic backbones encompasses by the term include methylphosphonate linkages or alternating methylphosphonate and phosphodiester linkages (Strauss-Soukup (1997) *Biochemistry* 36:8692–8698), and benzylphosphonate linkages which, compared with unmodified oligonucleotides and methylphosphonates, are more stable against nucleases and exhibit a higher lipophilicity (Samstag (1996) *Antisense Nucleic Acid Drug Dev* 6:153–156). The term nucleic acid is used interchangeably with gene, cDNA, mRNA, oligonucleotide primer, probe and amplification product. The term "exogenous nucleic acid" refers to a nucleic acid that has been isolated, synthesized, cloned, ligated, excised in conjunction with another nucleic acid, in a manner that is not found in nature, and/or introduced into and/or expressed in a cell or cellular environment other than or at levels or forms different than the cell or cellular environment in which said nucleic acid or protein is be found in nature. The term encompasses both nucleic acids originally obtained from a different organism or cell type than the cell type in which it is expressed, and also nucleic acids that are obtained from the same cell line as the cell line in which it is expressed. invention.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.*, 82:2306–2309 (1985), or the ciliate Macronucleus, may be used when the nucleic acid is expressed in using the translational machinery of these organisms.

As used herein, "having amino acid (or nucleic acid) sequence identity as measured using a sequence comparison algorithm" means optimal alignment of sequences for comparison using any means to analyze sequence identity (homology) known in the art, e.g., by the progressive alignment method of termed "PILEUP" (see below); by the local homology algorithm of Smith & Waterman, *Adv. Appl. Math.* 2: 482 (1981); by the homology alignment algorithm of Needleman & Wunsch, *J. Mol. Biol.* 48:443 (1970); by the search for similarity method of Pearson & Lipman, *Proc.*

Nat'l. Acad. Sci. USA 85: 2444 (1988); by computerized implementations of these algorithms (GAP, BESTFIT, FASTA, and TFASTA in the Wisconsin Genetics Software Package, Genetics Computer Group, 575 Science Dr., Madison, Wis.); or, by inspection. See also Morrison (1997) Mol. Biol. Evol. 14:428–441, as an example of the use of PileUp, ClustalW, TreeAlign, MALIGN, and SAM sequence alignment computer programs.

One example, PILEUP, creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5: 151–153 (1989). The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison. For example, IMP.18p can be compared to other IMP sequences using the following parameters: default gap weight (3.00), default gap length weight (0.10), and weighted end gaps.

Another example of algorithm that is suitable for determining sequence similarity is the BLAST algorithm, which is described in Altschul et al., J. Mol. Biol. 215: 403–410 (1990). Software for performing BLAST analyses is publicly available through the National Center for Biotechnology Information, http://www.ncbi.nlm.nih.gov. This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

The BLAST algorithm performs a statistical analysis of the similarity between two sequences (see, e.g., Karlin & Altschul, Proc. Nat'l. Acad. Sci. USA 90: 5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to IMP.18p nucleic acid of SEQ ID NO:16 if the smallest sum probability in a comparison of the test nucleic acid to the IMP.18p nucleic acid is less than about 0.1, more preferably less than about 0.01, and most preferably less than about 0.00 1. Where the test nucleic acid encodes an IMP.18p or clone 22 polypeptide, it is considered similar to the IMP.18p nucleic acid of SEQ ID NO:16 if the comparison results in a smallest sum probability of less than about 0.5, and more preferably less than about 0.2.

A "comparison window", as used herein, includes reference to a segment of about 10 to 20 residues in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman (1981) Adv. Appl. Math. 2: 482; by the homology alignment algorithm of Needleman and Wunsch (1970) J. Mol. Biol. 48: 443; by the search for similarity method of Pearson and Lipman (1988) Proc. Natl. Acad. Sci. USA 85: 2444; by computerized implementations of these algorithms (including, but not limited to CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA); the CLUSTAL program is well described by Higgins and Sharp (1988) Gene, 73: 237–244 and Higgins and Sharp (1989) CABIOS 5: 151–153; Corpet, et al. (1988) Nucleic Acids Research 16, 10881–90; Huang, et al. (1992) Computer Applications in the Biosciences 8, 155–65, and Pearson, et al. (1994) Methods in Molecular Biology 24, 307–31. "Sequence identity" in the context of two nucleic acid or polypeptide sequences includes reference to the nucleotides (or residues) in the two sequences which are the same when aligned for maximum correspondence over a specified "comparison window." When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a fall mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA). An indication that two peptide sequences are substantially similar is that one peptide is immunologically reactive with antibodies raised against the second peptide. Thus, a peptide is substantially similar to a second peptide, for example, where the two peptides differ only by a conservative substitution.

By "selectively hybridizing to," "specifically hybridizing to" or "selective hybridization" is meant hybridization, under stringent hybridization conditions, of a nucleic acid sequence to a specified nucleic acid target sequence to a detectably greater degree than its hybridization to non-target nucleic acid sequences. Specifically, as used herein, a specific or selective hybridization reaction (which is, by definition, under stringent hybridization conditions) will be at least about 10 times greater than the background signal or noise. Generally, selectively hybridizing primer sequences yield an amplicon composition which can comprise at least 90% of the target amplicon. Selectively hybridizing sequences can have at least about 80% sequence identity, preferably 90% sequence identity, and most preferably 100% sequence identity (i.e., complementary) with each other. "Percentage of sequence identity" is determined by comparing two optimally aligned sequences over a comparison window (10–20 nucleotides), wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, "stringent conditions" includes reference to conditions under which a nucleic acid sequence, such as a probe, will preferentially hybridize to its target sequence and/or hybridize to its target sequence to the substantial exclusion of non-target sequences. As defined herein, a specific or selective hybridization reaction under stringent hybridization conditions will be at least about 5 to 10 times greater than the background signal or noise. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary the target sequence hybridize to the target sequence at equilibrium. (As the target sequences are generally present in excess, at Tm 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C. "Stringent hybridization conditions" or "stringent conditions" in the context of nucleic acid hybridization assay formats are sequence dependent, and are different under different environmental parameters. An extensive guide to the hybridization of nucleic acids is found in Tijssen (1993) *Laboratory Techniques in Biochemistry and Molecular Biology— Hybridization with Nucleic Acid Probes* Part I, Chapter 2 "Overview of principles of hybridization and the strategy of nucleic acid probe assays", Elsevier, N.Y.

As used herein, "antibody composition" includes reference to at least one antibody. In turn, "antibody" includes reference to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab', F(ab')$_2$, Fab, Fv, rIgG, and, inverted IgG). See, Pierce Catalog and Handbook, 1994–1995 (Pierce Chemical Co., Rockford, Ill.). An antibody immunologically reactive with a particular antigen can be generated in vivo or by recombinant methods such as selection of libraries of recombinant antibodies in phage or similar vectors. See, e.g., Huse et al. (1989) *Science* 246:1275–1281; and Ward, et al. (1989) *Nature* 341:544–546; and Vaughan et al. (1996) *Nature Biotechnology*, 14:309–314.

As used herein, "specifically reactive" includes reference to the preferential association of a ligand, in whole or part, with a particular target molecule (i.e., "binding partner" or "binding moiety") relative to compositions lacking that target molecule. As defined herein, a specific or selective binding reaction will be at least about 10 times greater than the background signal or noise. It is, of course, recognized that a certain degree of non-specific interaction may occur between a ligand and a non-target molecule. Nevertheless, specific binding, may be distinguished as mediated through specific recognition of the target molecule. Typically specific binding results in a much stronger association between the ligand and the target molecule than between the ligand and non-target molecule. Specific binding by an antibody to a protein under such conditions requires an antibody that is selected for its specificity for a particular protein. The affinity constant of the antibody binding site for its cognate monovalent antigen is at least between $10^6$–$10^7$, usually at least $10^8$, preferably at least $10^9$, more preferably at least $10^{10}$, and most preferably at least $10^{11}$ liters/mole. The phrase "specifically (or selectively) binds to an antibody" or "specifically (or selectively) immunoreactive with," refers to an antibody binding reaction (including, at a minimum, an immunogenic binding fragment) that is determinative of the presence of a protein in a heterogeneous population of proteins and other compositions or biologics. Thus, under designated immunoassay conditions, the specified antibodies bind to a particular protein and do not bind in a significant amount to other proteins present in the sample. As defined herein, a specific or selective antibody binding reaction will be at least about 10 times greater than the background signal or noise. Specific binding to an antibody under such conditions may require an antibody that is selected for its specificity for a particular protein. For example, antibodies raised to IMP.18p with the amino acid sequence encoded in SEQ ID NO:17 are selected to obtain antibodies specifically immunoreactive with IMP.18p proteins and polymorphic variants of IMP.18p within the scope of the claimed invention, and not with other proteins. The anti-IMP.18p antibodies and antisera of the invention have less than 10% cross-reactivity to (e.g., as they are immunosorbed against) previously characterized anti-IMP polypeptides, as discussed below.

A variety of immunoassay formats may be used to select antibodies specifically immunoreactive with a particular protein and its polymorphic variants, as discussed in detail below. Solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). For example, as discussed below, a competitive binding immunoassay is used to identify and isolate putative IMP.18p polymorphic variants within the scope of the claimed invention.

An "immunogen" or "immunogenic fragment" refers to a compound or composition comprising a carbohydrate, peptide, polypeptide or protein which is "immunogenic," i.e., capable of eliciting, augmenting or boosting a cellular and/or humoral immune response, either alone or in combination or linked or fused to another substance. An immunogenic composition can be a peptide of at least about 5 amino acids, a peptide of 10 amino acids in length, or preferably, the a fragment 15 amino acids in length and more preferably a fragment 20 amino acids in length or greater. The immunogen (immunogenic fragment) can comprise a "carrier" polypeptide and a hapten (e.g., a carrier polypeptide fused or linked (chemically or otherwise) to a peptidel protein fragment against which the desired antibody will specifically recognize). The immunogen can be recombinantly expressed in an immunization vector, which can be simply naked DNA comprising the immunogen's coding sequence operably linked to a promoter. The immunogen (immunogenic fragment) includes antigenic determinants, or epitopes (described below), to which antibodies or TCRs bind, which are typically 3 to 10 amino acids in length. An "immunological carrier" is an composition which, when linked, joined, chemically coupled or fused to a second composition (e.g., protein, peptide, polysaccharide or the like) boosts or augments the cellular or humoral response to the composition. Any physiologic mechanism can be involved in this augmentation or boosting of the immune response. An immunogenic carrier is typically a polypeptide linked or fused to a second composition of interest—the immunogenic fragment—comprising a protein, peptide or polysaccharide, where the carrier stimulates a cellular (T cell mediated) immune response that boosts or augments the humoral (B cell mediated, antibody-generating) immune response to the composition of interest. These second compositions can be "haptens," which are typically defined as compounds of low molecular weight that are not immunogenic by themselves, but that, when coupled to carrier molecules, can elicit antibodies directed to epitopes on the hapten. Alternatively, an immunogenic fragment can be linked to a carrier simply to facilitate manipulation of the peptide in the generation of the immune response (see, for example, Rondard (1997) *Biochemistry* 36:8962–8968). An "epitope" refers to an antigenic determinant or antigen site on the immunogenic fragment that interacts with an antibody or a T cell receptor (TCR). An "antigen" is a molecule or composition that induces the production of an immune response. An antibody or TCR binds to a specific conformational (possibly charge-dependent) domain of the antigen, called the "antigenic determinant" or "epitope" (TCRs bind the epitope in association with a third molecule, a major histocompatibility complex (MHC) protein).

The term "immunologically reactive conditions" refers to any environment in which antibodies can bind to antigens, such as the IMP.18p of the invention or immunogenic fragments thereof. These conditions can be physiologic conditions similar to those seen in vivo, or, in vitro conditions compatible with antibody-antigen binding, such as in an immunological binding assay.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The amino acids and analogs referred to herein are described by shorthand designations as follows:

| Amino Acid Nomenclature | | |
|---|---|---|
| Name | 3-letter | 1-letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Those of ordinary skill will readily understand that proteins of the present invention embrace minor variants of the isoforms of clone 22 SEQ ID NO:3 and SEQ ID NO:4; and, IMP.18p proteins. Accordingly, the present invention embraces conservatively modified variants of the clone 22 and IMP.18p proteins and substantially similar variants of clone 22 and IMP.18p proteins. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W.H. Freeman and Company.

One of ordinary skill will recognize that individual substitutions, deletions or additions to a protein sequence which alters, adds or deletes a single amino acid or a small percentage of amino acids in the encoded sequence is a "conservatively modified variant" where the alteration results in the substitution of an amino acid with a chemically similar amino acid.

As used herein, "calculated molecular weight" of a polypeptide or peptide is the molecular weight based on the polypeptide's or peptide's deduced amino acid sequence—the deduced translation product—as encoded by the corresponding nucleic acid. In contrast, the "apparent" molecular weight is measured, empirical value. The apparent molecular weight of a protein can be determined by many different methods, all known to one of skill in the art. Some methods of determination include: SDS gel electrophoresis, native gel electrophoresis, molecular exclusion chromatography, zonal centrifugation, mass spectroscopy. Disparity between results of different techniques can be due to factors inherent in the technique. For example, native gel electrophoresis, molecular exclusion chromatography and zonal centrifugation depend on the size of the protein. The proteins that are cysteine rich can form many disulfide bonds, both intra- and intermolecular. SDS gel electrophoresis depends on the binding of SDS to amino acids present in the protein. Some amino acids bind SDS more tightly than others, therefore, proteins will migrate differently depending on their amino acid composition. Mass spectroscopy and calculated molecular weight from the sequence in part depend upon the frequency that particular amino acids are present in the protein and the molecular weight of the particular amino acid. If a protein is glycosylated, mass spectroscopy results will reflect the glycosylation but a calculated molecular weight may not.

As used herein, "recombinant" includes reference to a protein produced using cells that do not have in their native form an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.*, 82:2306–2309 (1985), or the ciliate Macronucleus, may be used when the nucleic acid is expressed in using the translational machinery of these organisms.

As used herein, "immunologically cross-reactive" or "immunologically reactive" includes reference to an antigen which is specifically reactive with an antibody which was generated using the same ("immunologically reactive") or different ("immunologically cross-reactive") antigen.

As used herein, "isoform" includes reference to a family of functionally related proteins that differ in their amino acid sequences but are derived from the same nuclear transcript.

The term "modulator" refers to any synthetic or natural compound or composition that can change in any way activity of protein of the invention, including IMP.18p or clone 22 proteins. A modulator can be an agonist or an antagonist. A modulator can be, but is not limited to, any organic and inorganic compound; including, for example, small molecules, peptides, proteins, sugars, nucleic acids, fatty acids and the like.

Method of Determining Increased Susceptibility To Manic-Depressive Illness

The present invention is directed to a method for determining a genotype associated with increased susceptibility to manic-depressive illness. The method comprises determining the genotype of a human individual diagnosed as manic-depressive. Methods of genotyping are well known to those of ordinary skill in the art. The genotype is determined using at least one polymorphic marker from within the region of chromosome 18 localized by and including the markers D18S843 and D18S869, see FIG. 3. Other markers within this region and the forward (F) and reverse (R) primers for amplification of and subsequent use of these markers for mapping are shown in Table 1.

Primers for polymorphic markers within this region of chromosome 18, including the markers D18S843 and D18S869, are publicly available on the internet. See, for example, The Genome Database at URL: http://gdbwww.gdb.org/; National Center for Biotechnology Information at URL: http://www.ncbi.nlm.nih.gov/SCIENCE96/ (cited in *Science*, Oct. 25, 1996, incorporated herein by reference); Cooperative Human Linkage Center at URL: http://www.chlc.org/; and the Location Database at URL: http.//cedar.genetics.soton.ac.uk/public_html/the information available in each of these databases on the date of filing is incorporated herein by reference. Primers and probes for markers are available from the ATCC. See the latest ATCC Repository listing, for example, on-line Internet or ATCC/NIH Repository Catalogue of Human and Mouse DNA Probes and Libraries, Eighth Edition 1995 (American Type Culture Collection, Rockville, Md.), incorporated herein by reference.

In preferred embodiments, genotyping within the interval of chromosome 18 localized by markers D18S843 and D18S869 (see FIG. 3) is determined using one of the markers selected from the group consisting of the marker of clone 22, D18S1116, and D18S1150. In a particularly preferred embodiment, the marker of clone 22 is used for determining the genotype. Preferably, the genotype within the interval of D18S843 and D18S869 is determined using markers D18S1153 ((also designated S53 in Table 3, below), D18S40 (also designated S40 in Table 3), D18S482, D18S71 (also designated S71 in Table 3), or D18S843.

TABLE 3

Infant brain derived cDNA clones mapping to chromosome 18.

| Clone Number | Our Insert Size (kB) | dbEST Insert Size (kb) | GenBank Accession Number | | Gene Homology* | EST Homology^ | Cytogenetic Bin |
|---|---|---|---|---|---|---|---|
| | | | 5' | 3' | | | |
| 1 | 1.4 | 1.7 | R51685 | R51596 | HS63XDAP | NA | M |
| 2 | 1.6 | NA | R61592 | R61536 | unknown | EST64032 | M |
| 3 | 1.6 | 2.1 | T77500 | R38384 | HS63XDAP | NA | M |
| 4 | 1.6 | 1.6 | R56762 | R56915 | unknown | unknown | M |

TABLE 3-continued

Infant brain derived cDNA clones mapping to chromosome 18.

| Clone Number | Our Insert Size (kB) | dbEST Insert Size (kb) | GenBank Accession Number 5' | GenBank Accession Number 3' | Gene Homology* | EST Homology^ | Cytogenetic Bin |
|---|---|---|---|---|---|---|---|
| 5 | 1.2 | 1.4 | HOS457 | HOS745 | unknown | unknown | S |
| 6 | 1.5 | 1.5 | R54360 | R54361 | unknown | unknown | S |
| 7 | 1.6 | 1.9 | T78290 | R37939 | MBP | NA | S |
| 8 | 1.9 | 2.4 | R20367 | R43753 | unknown | unknown | M |
| 9 | 1.2 | 1.2 | R18592 | R41672 | unknown | EST197262 | S |
| 10 | 1.3 | 1.4 | R15875 | R37298 | HS63XDAP | NA | M |
| 11 | 1.5 | 1.5 | R34535 | R49065 | PTFRM | NA | A |
| 12 | 1.8 | 2.0 | H17696 | H17080 | MBP | NA | S |
| 13 | 1.7 | 1.9 | R52596 | R52541 | unknown | unknown | L |
| 14 | 1.8 | 2.0 | R13520 | R20642 | unknown | unknown | A |
| 15 | 1.4 | NA | R16321 | R41398 | unknown | EST228925 | K |
| 16 | 1.7 | NA | HO8970 | HO9539 | unknown | unknown | S |
| 17 | 1.6 | 2.1 | R17799 | R43004 | unknown | EST64032 | M |
| 18 | 1.5 | 1.0 | R22831 | R46021 | MBP | NA | S |
| 19 | 2.0 | 2.8 | R14016 | R39139 | unknown | unknown | M |
| 20 | 1.1 | 1.3 | R11914 | R39106 | unknown | EST197262 | S |
| 21 | 1.5 | 2.0 | R19053 | R44040 | unknown | EST228925 | M |
| 22 | 1.1 | 1.2 | R13448 | R44696 | unknown | unknown | C |
| 23 | 1.1 | 1.2 | TS0229 | R38716 | unknown | D188928E | S |
| 24 | 1.2 | 1.5 | R35001 | R49388 | unknown | EST91427 | A |
| 25 | 1.9 | 2.1 | R17655 | R43373 | unknown | unknown | M |
| 26 | 1.0 | 1.2 | R20441 | R44144 | unknown | EST197262 | S |
| 27 | 1.3 | 1.4 | R19332 | R44600 | unknown | EST91427 | A |
| 28 | 1.8 | NA | H08354 | H08355 | unknown | EST91427 | A |
| 29 | 1.8 | 1.7 | none | R39845 | unknown | unknown | B |
| 30 | 1.3 | 1.4 | R52394 | R52395 | unknown | EST130984 | N |
| 31 | 1.1 | 1.3 | H17749 | H17636 | GMAL | NA | B |
| 32 | 1.1 | 1.1 | H06013 | H05964 | unknown | EST91427 | A |
| 33 | 1.7 | 1.9 | T74001 | TS7210 | unknown | unknown | M |
| 34 | 1.9 | 1.3 | T50579 | R38876 | unknown | unknown | A |
| 35 | 1.4 | NA | R60481 | R60245 | unknown | EST91427 | A |
| 36 | 1.2 | NA | R59504 | R53505 | unknown | unknown | K |
| 37 | 1.9 | 2.1 | R20248 | R43704 | unknown | unknown | B |
| 38 | 1.1 | 1.1 | H08492 | H08770 | unknown | unknown | M |
| 39 | 1.6 | 1.7 | H11689 | H11600 | unknown | unknown | G |
| 40 | 1.7 | 1.9 | R19498 | R43846 | HUMKIAAN | NA | N |
| 41 | 1.6 | 2.0 | H17610 | H17501 | unknown | unknown | S |
| 42 | 1.8 | 5.9 | R17567 | R42507 | unknown | EST91427 | A |
| 43 | 1.5 | 1.5 | R20380 | R43767 | unknown | unknown | S |
| 44 | 1.6 | 1.6 | H17267 | H17268 | unknown | EST91427 | A |
| 45 | 1.6 | 1.6 | TS0517 | R38994 | PTFRM | NA | A |
| 46 | 1.6 | 1.4 | R20075 | none | MBF | NA | S |
| 47 | 1.2 | 1.3 | T66113 | T65029 | unknown | unknown | S |
| 48 | 1.3 | 1.3 | R15279 | none | unknown | EST91427 | A |

*Determined vis BLASTN searches (Altschul, 1990) and intragroup redundancy of >89% over >100 base pairs with another of the 48 clones via Pasta (Pearson and Lipman, 1988).
^Determinded by searching the UniQene (Boguski and Schuler, 1995) site with the above GenBank account numbers which showed homology with six UniQene groups (taking into account redundancy), one member of whihc had been previously mapped to chromosome 18.

As will be recognized by those of skill, the complementary sequences of these primers may likewise be employed for amplifying or selectively hybridizing and detecting their target marker. Additional target regions may be identified by walking from known chromosome markers as described above. Techniques for chromosome walking are well known in the art as described in Sambrook et al., *Molecular Cloning. A Laboratory Manual*, Cold Spring Harbor Press, 1989. Vectors which are optimized for chromosome walking are commercially available (e.g., lambda-DASH and lambda-FIX (Stratagene Cloning Systems, La Jolla, Calif.).

Figure 3:
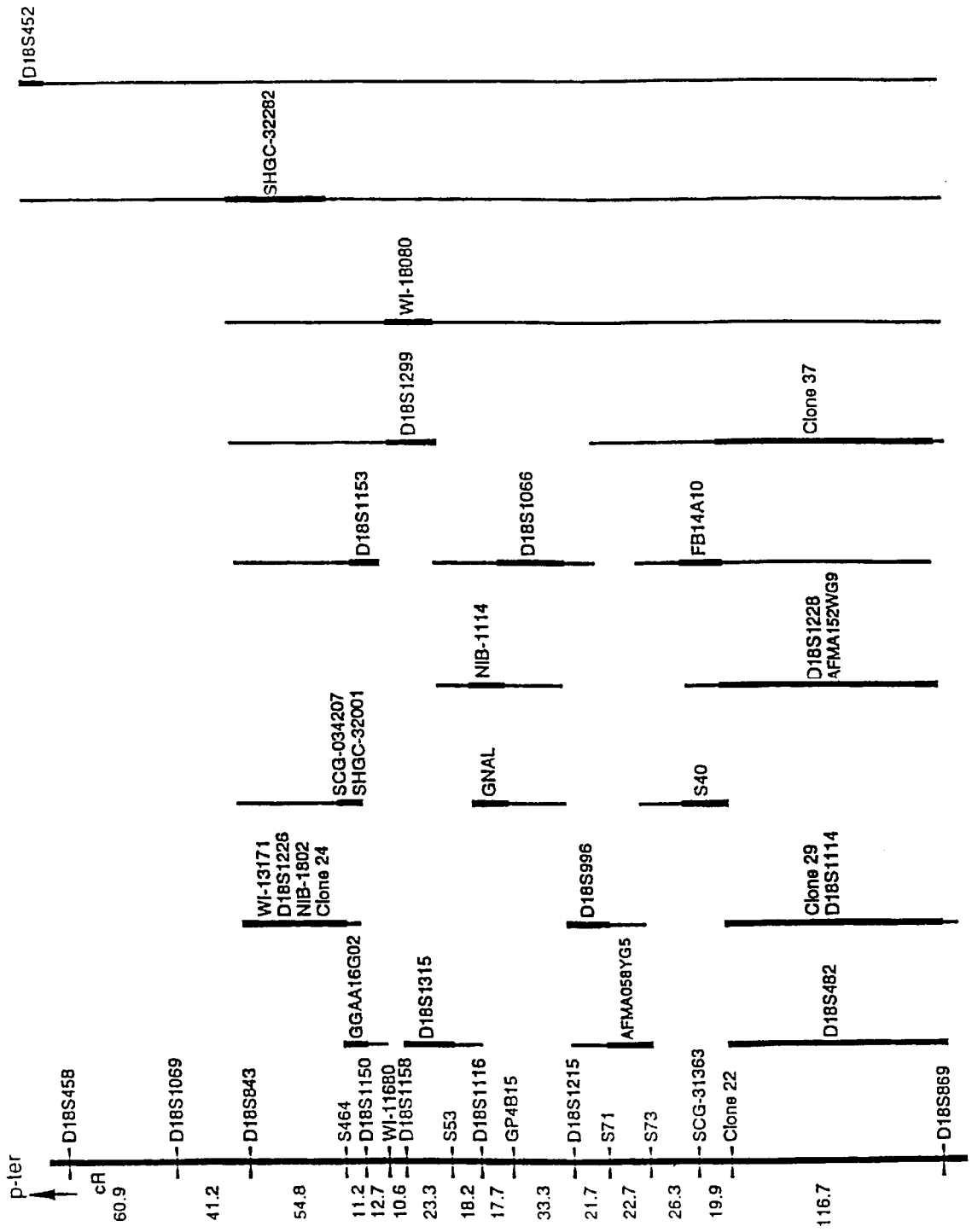
FIG. 3 shows the results of radiation hybrid mapping of the 18p11.2 region. Distances are shown in centirays (cR). Vertical lines represent probable locations of the indicated markers. Thickened vertical lines indicate the most probable location of the indicated markers.

New markers may result from physical mapping of the interval defined by (flanked by) markers D18S843 and D18S869, see FIG. 3. In a particularly preferred embodiment, the polymorphic marker of clone 22 is employed. The polymorphic marker of clone 22 is a microsatellite marker comprising a trinucleotide repeat amplified by primers with the sequences set forth in SEQ ID NO:1 and SEQ ID NO:2 (Table 1). Allele 1 and allele 2 comprise the two polymorphisms at the clone 22 locus. The polymorphism amplified by primers of SEQ ID NO:1 and SEQ ID NO:2 is a trinucleotide repeat consisting essentially of 10 GCT trinucleotides for allele 1 (SEQ ID NO:14), while the polymorphism amplified by these primers is a trinucleotide repeat consisting essentially of 9 GCT trinucleotides for allele 2. The presence of allele 2 (SEQ ID NO:15) of the polymorphic marker indicates an increased susceptibility to manic-depressive illness.

Markers from within the region localized by and including markers D18S843 and D18S869 are linked to a locus associated with susceptibility to manic-depressive illness (bipolar disorder). Linkage disequilibrium between a polymorphism from this region and the appearance of manic-depressive illness provides a means of associating the appearance of that polymorphism in an individual with an increased susceptibility to manic-depressive illness. Consequently, a polymorphism exhibiting linkage disequilibrium with the appearance of manic-depressive illness can be used as a standard against which an increased susceptibility to manic-depressive illness can be determined for an individual whose disease status is unknown.

In the present method, a statistically significant correlation between the presence of a particular polymorphism with the presence of manic-depressive illness in an individual allows for the determination of the genotype(s) associated with increased or decreased susceptibility to familial manic-depressive illness. In a preferred embodiment, the transmission disequilibrium test (TDT) is employed to determine a genotype associated with increased susceptibility to manic-depressive illness. See, Spielman et al., *Am. J. Hum. Gene.*, 52:506–516 (1993); Spielman and Ewens, *Am. J. Hum. Gene.*, 59:983–989 (1996), both of which are incorporated herein by reference. Briefly, the TDT considers parents who are heterozygous for an allele associated with disease and evaluates the frequency with which that allele or its alternate is transmitted to affected offspring.

The genotype of the tested individual can be conveniently determined with at least one polymorphic marker localized within the chromosomal region defined (flanked) by and including markers D18S43 and D18S869 (FIG. 3). Typically, the same marker or markers are used as in determining the genotype associated with increased susceptibility to manic-depressive illness. In a preferred embodiment, the polymorphic marker is amplified by primers which selectively hybridize, under stringent conditions, to the same nucleic acid sequences as primers of SEQ ID NO:1 and SEQ ID NO:2 (Table 1).

Methods of amplifying sequences are well known to those of ordinary skill in the art. Amplification systems include the polymerase chain reaction (PCR) system, strand displacement amplification (SDA), see, e.g., *Diagnostic Molecular Microbiology: Principles and Applications*, Ed. D. H. Persing et al., American Society for Microbiology, Washington, D.C.; ligase chain reaction (LCR) (Wu (1989) *Genomics* 4:560; Landegren (1988) *Science* 241:1077; Barringer (1990) *Gene* 89:117); transcription amplification (Kwoh *Proc. Natl. Acad. Sci. USA*, 86:1173 (1989)); and, self-sustained sequence replication (Guatelli (1990) *Proc. Natl. Acad. Sci. USA*, 87:1874); Q Beta replicase amplification and other RNA polymerase mediated techniques (e.g., NASBA, Cangene, Mississauga, Ontario); see Berger (1987) *Methods Enzymol.* 152:307–316, Sambrook, and Ausubel, as well as Mullis (1987) U.S. Pat. Nos. 4,683,195 and 4,683,202; Arnheim (1990) *C&EN* 36–47; Lomell *J. Clin. Chem.*, 35:1826 (1989); Van Brunt, *Biotechnology*, 8:291–294 (1990); Wu (1989) *Gene* 4:560; Sooknanan (1995) *Biotechnology* 13:563–564. Methods for cloning in vitro amplified nucleic acids are described in Wallace, U.S. Pat. No. 5,426,039.

The PCR process is well-known in the art and is thus not described in detail herein. For a review of PCR methods and protocols, see, e.g., Innis, et al. eds. *PCR Protocols. A Guide to Methods and Application* (Academic Press, Inc., San Diego, Calif. 1990). PCR reagents and protocols are also available from commercial vendors, such as Roche Molecular Systems. See, U.S. Pat. Nos. 4,683,195; 4,683,202; 4,800,159; 4,965,188, each of which is incorporated herein by reference. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a preferred embodiment of the PCR process, strand separation is achieved by heating the reaction to a sufficiently high temperature for a sufficient time to cause the denaturation of the duplex but not to cause an irreversible denaturation of the polymerase. Template-dependent extension of primers in PCR is catalyzed by a polymerizing agent in the presence of adequate amounts of four deoxyribonucleotide triphosphates (typically DATP, dGTP, dCTP, and dTTP) in a reaction medium comprised of the appropriate salts, metal cations, and pH buffering system. Suitable polymerizing agents are enzymes known to catalyze template-dependent DNA synthesis. The methods of the present invention may be performed on a wide variety of human cells including somatic cell hybrids, purified nuclei, chromosomal preparations or nucleic acid sequences comprising a marker to a chromosomal region of the present invention. The cells may be somatic or germline and from any time in gestation including fertilized embryo or preimplantation blastocysts. Preferably, somatic cells are employed to avoid the possibility of meiotic recombination events between a marker and locus associated with susceptibility to manic-depressive illness and to more readily allow determination of the genotype for a homologous chromosome pair.

The methods of the present invention may conveniently be practiced with markers which differ as to sequence or length, such as RFLPs (restriction fragment length polymorphisms) and microsatellite markers such as STRPs (short tandem repeat polymorphisms) or VNTRs (variable number tandem repeats). Generally, the sizes will be determined by standard gel electrophoresis techniques as described in Sambrook et al., *Molecular Cloning, A Laboratory Manual*, Cold Spring Harbor Press, 1989, and Polymeropoulos et al., *Genomics*, 12:492–496 (1992). Polyacrylamide gel electrophoresis is particularly preferred because of its capability of high discrimination. Generally, autoradiography is employed to simultaneously visualize and identify the markers.

Amplification of markers is generally performed with labeled nucleotide bases that provide a means for identifying the amplified product following the procedure. Alternatively, labeled nucleic acid primers can be employed as probes.

Probes can be used to selectively hybridize and detect and isolate a nucleic acid sequence (e.g., a cDNA or gene) of interest. For example, labeled probes can be used to detect RFLP markers which differ in size after digestion with one or more restriction enzymes which have been separated, as by electrophoresis.

Where the nucleic acid encoding a clone 22 or IMP.18p protein is to be used as a nucleic acid probe, it is often desirable to label the nucleic acid with detectable labels. The labels may be incorporated by any of a number of means well known to those of skill in the art. The label can be simultaneously incorporated during the amplification procedure in the preparation of the nucleic acids. Thus, for example, polymerase chain reaction (PCR) with labeled primers or labeled nucleotides will provide a labeled amplification product. In another preferred embodiment, transcription amplification using a labeled nucleotide (e.g., fluorescein-labeled UTP and/or CTP) incorporates a label into the transcribed nucleic acids.

Alternatively, a label may be added directly to an original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g., with a labeled RNA) by phosphorylation of the nucleic acid and subsequent attachment (ligation) of a nucleic acid linker joining the sample nucleic acid to a label (e.g., a fluorophore).

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate. Probes may be labeled with visual labels such as photoluminescents, Texas red, rhodamine and its derivatives, red leuco dye and 3,3', 5,5'-tetramethylbenzidine (TMB), fluorescein and its derivatives, dansyl, umbelliferone and the like. Enzymes such as horse radish peroxidase, alkaline phosphatase, or equivalents can be used, especially in ELISAs. Magnetic beads, fluorescent dyes (e.g., fluorescein, texas red, rhodamine, green fluorescent protein, and the like), radio-labels (e.g., $^3$H, $^{125}$I, $^{35}$S, $^{14}$C, or $^{32}$P), and colorimetric labels such as colloidal gold or colored glass or plastic (e.g., polystyrene, polypropylene, latex, etc.) beads are also useful labeling means. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Those of skill will recognize that polymorphic markers within the region localized within and including D18S843 and D18S869 can be identified by variations at the protein level when the polymorphism occurs within a coding region. The present invention includes the use of polymorphisms which manifest themselves at both the nucleic acid and protein sequence levels. Accordingly, means of distinguishing polymorphisms include, but are not limited to, differences arising from antigenicity, substrate specificity, or activity of encoded proteins.

Isolation of nucleic acids from biological samples for use in the present invention may be carried out by a variety of means well known in the art. For example, see those described in Rothbart et al., 1989, in *PCR Technology* (Erlich ed., Stockton Press, New York) and Han et al., 1987, *Biochemistry*, 26:1617–1625. Kits are also commercially available for the extraction of high-molecular weight DNA for PCR. These kits include Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, NH), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA prior to practicing the methods of the present invention. In some case, the informative marker may be transcribed into RNA by the cells. In this instance, RNA may be used for amplification or for comparison between the tested individual and affected family member.

In another aspect, the present invention provides a method for determining an increased susceptibility to manic-depressive illness in an individual. Due to linkage disequilibrium the presence of allele 2 (SEQ ID NO:15) of the clone 22 polymorphism appears more frequently amongst individuals in the U.S. population who have increased susceptibility to manic-depressive illness than individuals who lack this allele. Consequently, the presence of allele of clone 22 is itself determinative of an increased susceptibility to manic-depressive illness. The tested individual may be a member of any racial or ethnic group, including, for example, individuals of European, African, or Asian descent. In preferred embodiments, the tested individual is of European descent. The method comprises determining the genotype of the individual using the polymorphic marker of clone 22. The polymorphic marker of clone 22 can be amplified with oligonucleotide primers which amplify the same polymorphic marker as primers of SEQ ID NO:1 and SEQ ID NO:2. Use of such primers on a target comprising allele 1 yields the nucleic acid having the sequence shown in SEQ ID NO:14. The allele 1 polymorphism consists of 10 trinucleotide (GCT) repeats. Use these same primers with a target nucleic acid of allele 2 yields the nucleic acid having the sequence shown in SEQ ID NO:15. The allele 2 polymorphism consists of 9 trinucleotide (GCT) repeats. Thus, primers of the present invention will amplify the region of the trinucleotide repeat polymorphism of clone 22. Those of skill will recognize that the priming of a target sequence is performed under stringent conditions such that the primers selectively hybridize to their target sequence. Preferably, the primers employed to amplify the polymorphism of clone 22 comprise the sequence of SEQ ID NO:1 and SEQ ID NO:2. The primers of SEQ ID NO:1 and SEQ ID NO:2 may comprise additional sequences to aid in such processes as purification, labeling, or subdloning. The use of additional 5' terminal sequences (i.e., tails) or 5' labels is well known to the skilled artisan.

Nucleic Acid and Protein Compositions

The invention provides for novel nucleic acids, and proteins encoded therefrom, derived from a specific area of human chromosome 18. Genetic variations in this chromosomal region have been shown to be associated with manic depressive illness, including bipolar disease, making these nucleic acids and proteins useful as diagnostic markers and targets for preventive and therapeutic treatments. Specific embodiments include novel nucleic acids and proteins identified as clone 22 and IMP.18p, both of which are encoded in this chromosome 18 region. These and other sequences within the region localized by and including markers D18S843 and D18S869, being linked to a locus associated with susceptibility to manic-depressive illness, are also used as diagnostic markers in the invention. The invention provides for novel nucleic acid and antibody reagents used to identify and isolate these nucleic acids sequences and proteins. The invention also provides for characterization and isolation of related species of clone 22 and IMP18.p using the novel reagents of the invention.

For example, one embodiment provides for a method for detecting the presence of, and thereby isolating, a polynucleotide sequence encoding at least a portion of an IMP.18p myo-inositol monophosphatase in a biological sample, comprising the steps of reacting a biological sample suspected of containing an IMP.18p nucleic acid with a probe comprising a nucleotide sequence of an IMP.18p, or a fragment thereof, capable of hybridizing to a myo-inositol monophosphatase-encoding nucleic acid from the biological sample. Embodiments which provide for a means of detecting these novel nucleic acids or proteins thus also provide means to diagnosing a myo-inositol monophosphatase-related conditions in a mammal. These methods comprise obtaining a cell or tissue sample from the mammal; determining the amount of an gene product in the cell or tissue; and comparing the amount of the gene product in the cell or tissue with the amount in a healthy cell or tissue of the same type; wherein a different amount of gene product in the sample from the mammal and the healthy cell or tissue is diagnostic of a myo-inositol monophosphatase-related condition.

On another embodiment, the invention provides for clone 22 nucleic acid and protein encoded therefrom. The common subsequence of the native (naturally occurring) clone 22 mRNA transcript is shown in DNA form as SEQ ID NO:6. This common sequence is expressed with one of two different 5' untranslated regions, SEQ ID NO:12 or SEQ ID NO:13. The present invention includes isolated nucleic acids comprising the common sequence, the 5' untranslated regions of SEQ ID NO:12 and SEQ ID NO:13, and subsequences thereof.

Two isoforms of clone 22 proteins are provided herein. The present invention includes these isolated proteins and subsequences thereof. One isoform of a clone 22 protein has the amino acid sequence shown in SEQ ID NO:3. The present invention provides isolated nucleic acids comprising a nucleic acid encoding the clone 22 protein of SEQ ID NO:3 and subsequences thereof. The present invention also provides isolated proteins comprising the amino acid sequence shown SEQ ID NO:3 and subsequences thereof.

The second isoform of the clone 22 protein comprises the amino acid sequence of SEQ ID NO:3 but lacks the amino acid sequence from position 113 to 130 (i.e., EGCLWPSDSAAPRLGASE) (SEQ ID NO:5). The second isoform has the protein sequence shown in SEQ ID NO:4. The present invention includes isolated nucleic acids comprising a nucleic acid encoding the alternatively spliced clone 22 protein of SEQ ID NO:4 and subsequences thereof. The present invention also provides isolated proteins comprising the amino acid sequence shown in SEQ ID NO:4 and subsequences thereof. Thus, the present invention provides nucleic acids ("clone 22 nucleic acids") and proteins ("clone 22 proteins") which include both full-length and subsequences of isolated native nucleic acids and proteins of clone 22.

With the amino acid sequences of the clone 22 and IMP.18p proteins provided herein, one of skill can readily construct a variety of clones containing nucleic acids which encode the same protein but vary in nucleic acid sequence due to the degeneracy of the genetic code. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook, et al., *Molecular Cloning: A Laboratory Manual* (2nd Ed., Vols. 1–3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987). Product information from manufacturers of biological reagents and experimental equipment also provide information useful in known biological methods.

In some embodiments the isolated nucleic acids of the present invention comprise the sequence shown in SEQ ID NO:6 from nucleotide 116 to 1033 (i.e., the sequence coding for the protein of SEQ ID NO:3); this nucleic acid is identified herein as SEQ ID NO:7. In other embodiments nucleic acids of the present invention comprise the sequence shown in SEQ ID NO:6 from nucleotide 116 to 1033 but lacking the sequence from nucleotide 452 to 505 corresponding to the region from Glu 113 to Glu 130 (i.e., lacking the region coding for the protein of SEQ ID NO:5); this nucleic acid is identified herein as SEQ ID NO:8.

A nucleic acid encoding the protein of SEQ ID NO:3 or SEQ ID NO:4 can be amplified from human brain cDNA libraries using primers which selectively hybridize, under stringent conditions, to the same nucleic acid sequence as primers of SEQ ID NO:9 and SEQ ID NO:10. Thus, for example, isolated nucleic acids encoding the isolated proteins of SEQ ID NO:3 or SEQ ID NO:4 can be amplified using oligonucleotide primers which selectively hybridize, under stringent conditions, to the same nucleic acid sequences of SEQ ID NO:7 and SEQ ID NO:8, respectively, as primers of SEQ ID NO:9 and SEQ ID NO:10.

The IMP.18p nucleic acid sequence (SEQ ID NO:16) and protein sequence information (SEQ ID NO:17) can be used to design PCR primers which can be used to identify related IMP species, such as: SEQ ID NO:18 and SEQ ID NO:19; SEQ ID NO:20 and SEQ ID NO:21; and, SEQ ID NO:22 and SEQ ID NO:23, can be used to directly amplify IMP species. The SEQ ID NO:18 (forward) and SEQ ID NO:19 (reverse) primer pair amplifies full length IMP.18p cDNA protein coding sequence:

5'-ATG AAG CCG AGC GGC GAG GAC-3' (SEQ ID NO:18)

5'-CTT CTC ATC ATC CCG CCC ATA G-3' (SEQ ID NO:19)

PCR primers such as SEQ ID NO:(forward, beginning at residue number 901, see FIG. 5B) and SEQ ID NO:21 (reverse, beginning residue 1380) can also be used to directly amplify new IMP species or to generate a DNA probe that would include mature protein coding region and much of the 3' untranslated region, i.e., the poly-A attachment site. These primers, whether used to directly amplify new IMP species, used directly as probes, or used to generate (by PCR amplification) longer DNA probes, will also hybridize to a wide variety of different IMP species, especially those including IMP sequence variants that are better conserved in the 3'-untranslated region than in the mature protein coding region:

5'-CTC GAC CTC ATGOGCT TGC AGA G-3' (SEQ ID NO:20)

5'-CTG AGA ACG ATC CGC TTT ATC-3' (SEQ ID NO:21)

PCR primers such as SEQ ID NO:22 (forward primer) and SEQ ID NO:23 (reverse) can also be used to directly amplify new IMP species and isoforms or to generate a DNA probe that would include an internal subset of IMP coding sequence. SEQ ID NO:22 and SEQ ID NO:23 primer pair amplifies an internal block of the coding sequence of IMP.18p protein. SEQ ID NO:22 and SEQ ID NO:23 correspond to coding sequence immediately upstream and downstream of motif A and motif B (discussed below), respectively (amino acids number 98 to 111 and 230 to 244, respectively, see FIG. 6; as numbered in FIG. 5B). As can be seen in FIG. 6, these primers correspond to relatively non-conserved IMP sequence:

5'-GTG TGT GCT CAC CCC GAC TGT-3' (SEQ ID NO:22)

5'-CCC GAA GTG TCT ATC ACG ATG-3' (SEQ ID NO:23)

The subsequences of the isolated nucleic acids of the present invention are at least N nucleotides in length, where N is any one of the integers selected from the group consisting of from 15 to 900. Typically, the subsequences are at least 20 nucleotides in length, preferably at least 25 nucleotides in length, preferably at least 30 nucleotides in length, and often at least 35, 40, or 50 nucleotides in length. The subsequences of the isolated proteins of the present invention are at least N' amino acids in length, where N' is any one of the integers from 5 to 300. The amino acid subsequences are derived from contiguous amino acids from the protein sequences of SEQ ID NO:3 or SEQ ID NO:4. The nucleic acid subsequences are derived from contiguous nucleotides from the nucleic acid sequences of SEQ ID NO:7 or SEQ ID NO:8. "Contiguous" with respect to a specified number of amino acid residues or nucleotides, includes reference to a sequence of amino acids or nucleotides, respectively, of the specified number from within the specified reference sequence which has the identical order of amino acids or nucleotides and the same adjacent amino acids or nucleotides as in the reference sequence.

The present invention also provides isolated mammalian proteins comprising a clone 22 protein subsequence and an IMP.18p subsequence of at least 10 contiguous amino acids, preferably at least 15 contiguous amino acids, more preferably at least 20 contiguous amino acids, and most preferably at least 25, 30, 35, or 40 contiguous amino acids. In the case of clone 22, these amino acid sequences are from SEQ ID NO:3. In the case of IMP.18p, these amino acid sequences are from SEQ ID NO:17. The isolated mammalian proteins are immunologically cross-reactive to an antibody composition that is generated from (e.g., screened, synthesized, or elicited) and specifically reactive to a protein immunogen of SEQ ID NO:3 and SEQ ID NO:17 for clone 22 and IMP.18p, respectively. The mammalian protein may be isolated from any number of mammals including: rat, nice, cattle, dog, pig, guinea pig, or rabbit, and most preferably a primate such as macaques, chimpanzees, or humans.

The isolated clone 22 and IMP.18p proteins of the present invention can be constructed using standard recombinant or synthetic methods. Solid phase synthesis of isolated proteins of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, *Solid-Phase Peptide Synthesis*; pp. 3–284 in *The Peptides: Analysis, Synthesis, Biology*. Vol. 2: *Special Methods in Peptide Synthesis*, Part A., Merrifield, et al. *J. Am. Chem. Soc.*, 85: 2149–2156 (1963), and Stewart et al., *Solid Phase Peptide Synthesis*, 2nd ed. Pierce Chem. Co., Rockford, Ill. (1984). Detailed descriptions of the procedures for solid phase synthesis of nucleic acids by phosphite-triester, phosphotriester, and H-phosphonate chemistries are widely available. For example, the solid phase phosphoramidite triester method of Beaucage and Carruthers using an automated synthesizer is described in Itakura, U.S. Pat. No. 4,401,796; Carruthers, U.S. Pat. Nos. 4,458,066 and 4,500,707; Carruthers (1982) *Genetic Engineering* 4:1–17; see also Needham-VanDevanter (1984) *Nucleic Acids Res.* 12:6159–6168; Beigelman (1995) *Nucleic Acids Res* 23: 3989–3994; Jones, chapt 2, Atkinson, chapt 3, and Sproat, chapt 4, in OLIGONUCLEOTIDE SYNTHESIS: A PRACTICAL APPROACH, Gait (ed.), IRL Press, Washington D.C. (1984); Froehler (1986) *Tetrahedron Lett.* 27:469–472; Froebler, *Nucleic Acids Res.* 14:5399–5407 (1986); Sinha, *Tetrahedron Lett.* 24:5843–5846 (1983); and Sinha, *Nucl. Acids Res.* 12:4539–4557 (1984). Methods to purify oligonucleotides include native acrylamide gel electrophoresis, anion-exchange HPLC, as described in Pearson (1983) *J. Chrom.* 255:137–149. The sequence of the synthetic oligonucleotide can be verified using any chemical degradation method, for example, see Maxam (1980) *Methods in Enzymology* 65:499–560, Xiao (1996) *Antisense Nucleic Acid Drug Dev* 6:247–258, or for solid-phase chemical degradation procedures, Rosenthal (1987) *Nucleic Acids Symp Ser* 18:249–252.

Proteins of greater length may be synthesized by condensation of the amino and carboxy termini of shorter fragments. Methods of forming peptide bonds by activation of a carboxy terminal end (e.g., by the use of the coupling reagent N,N'-dicycylohexyl carbodiimide) is known to those of skill.

Subsequences of nucleic acids can be used as probes to detect or isolate the clone 22 and IMP.18p encoding nucleic acids for further analysis of the polymorphism contained therein for purposes described more fully, supra. Additionally, subsequences can be utilized as primers for amplification of the clone 22 and IMP.18p polymorphisms. The subsequence may be derived from within any portion of the clone 22 isoforms and IMP.18p coding sequence. Probes specific to one or the other isoform of clone 22 can be used to study differential transcription of these isoforms.

Isolated nucleic acids of the present invention can also be used for recombinant expression of the proteins of the present invention for use as immunogens in the preparation of antibodies. Subsequences can also be used for detecting and/or quantifying clone 22 protein and IMP.18p expression by assaying for the gene transcript (e.g., nuclear RNA, mRNA) using nucleic acids coding for clone 22 and IMP.18p proteins. The assay can be for the presence or absence of the normal gene or gene product, for the presence or absence of an abnormal gene or gene product, or quantification of the transcription levels of normal or abnormal clone 22 and IMP.18p gene product. Nucleic acid assays are well known in the art and included in standard molecular biology references such as those incorporated by reference herein.

For example, amongst the various hybridization formats well known to the skilled artisan is included solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3):230–250 (1986); Haase et al., *Methods in Virology*, Vol. VII, pp. 189–226 (1984); Wilkinson, "The theory and practice of in situ hybridization" In: *In situ Hybridization*, Ed. D. G. Wilkinson. IRL Press, Oxford University Press, Oxford; and *Nucleic Acid Hybridization: A Practical Approach*, Ed. Hames, B. D. and Higgins, S. J., IRL Press (1987).

Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%.

The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium as described below. Thus, despite the lack of 100 percent complementarity under reduced conditions of stringency, functional nucleic acids of the present invention having minor base differences from the nucleic acid targets are possible. Therefore, under hybridization conditions of reduced stringency, it may be possible to construct an oligonucleotide having substantial identity to an oligonucleotide complementary to the target sequence while maintaining an acceptable degree of specificity. Substantial identity in the context of nucleic acids means that the two molecules hybridize to each other under stringent conditions. Generally, stringent conditions are selected to be about 5° C. to 20° C. lower than the thermal melting point ($T_m$) for the specific sequence at a defined ionic strength and pH. Typically, stringent conditions will be those in which the salt concentration is about 0.02 molar at pH 7 and the temperature is at least about 60° C., more preferably 65° C.; however, for in situ hybridization the temperature is preferably 40° C. Stringent conditions typically include at least one wash in 0.2×SSC at a temperature of at least about 50° C., usually about 55° C. to about 60° C., for 20 minutes, or equivalent conditions. The hybridization format or buffers are not critical aspects of the present invention and those of skill will recognize that firther advances, improvements, or modifications in nucleic acid hybridization, amplification, and detection are within the scope of the invention.

The nucleic acids of the present invention, whether derived from a biological source, artificially constructed or both, can be operably linked to a promoter. Those of ordinary skill will recognize that an isolated duplex clone 22 or IMP.18p nucleic acid operably linked to a promoter in forward orientation can direct transcription of mRNA which can be translated into a clone 22 or IMP.18p protein of the present invention. An isolated duplex clone 22 or IMP.18p nucleic acid operably linked to a promoter in reverse orientation can direct transcription of antisense mRNA. Antisense nucleic acids can be used for probes in assays for normal or abnormal gene product or to quantitate the expression of mRNA coding for the clone 22 or IMP.18p protein in, for example, drug assays. Accordingly, the isolated nucleic acids of the present invention are inclusive of both sense and antisense nucleic acids.

The isolated nucleic acid compositions of this invention, whether RNA, cDNA, genomic DNA, or a hybrid of the various combinations, are isolated from biological sources or synthesized in vitro. Deoxynucleotides encoding isolated proteins of the present invention can be prepared by any suitable method including, for example, cloning and restriction of appropriate sequences as discussed supra, or by direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.*, 22: 1859–1862 (1981); the solid phase phosphorarnidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168; and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Once the nucleic acid encoding a protein of the present invention is isolated and cloned, one may express the desired protein in a recombinantly engineered cell such as bacteria, yeast, insect (especially employing baculoviral vectors), and mammalian cells. It is expected that those of skill in the art are knowledgeable in the numerous expression systems available for expression of proteins. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the protein. To obtain high level expression of a cloned gene, it is desirable to construct expression vectors which contain, at the minimum, a strong promoter to direct transcription, a ribosome binding site for translational initiation, and a transcription/translation terminator. One of skill would recognize that minor modifications can be made to a clone 22 or IMP.18p protein. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Examples of techniques and instructions sufficient to direct persons of skill through many cloning exercises are found in Berger and Kirnmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Cloning vectors and host cells are readily obtained through commercial sources or from the American Type Culture Collection, each of which is incorporated herein by reference.

1. Expression in Prokarvotes

Bacterial strains which can be used to express the nucleic acid of the invention include Escherichia coli, Bacillus subtillus, Streptococcus cremoris, Streptococcus lactis, Streptococcus thermophilus, Leuconostoc citrovorum, Leuconostoc mesenteroides, Lactobacillus acidophilus, Lactobacillus lactis, Bifidobacterium bifidum, Bifidobacteriu breve, and Bifidobacterium longum.

Examples of regulatory regions suitable for this purpose in E. coli are the promoter and operator region of the E. coli tryptophan biosynthetic pathway as described by Yanofsky, Bacteriol. 158:1018–1024 (1984), and the lefiward promoter of phage lambda ($P_L$) as described by Herskowitz and Hagen, Ann. Rev. Gene., 14:399–445 (1980). The inclusion of selection markers in DNA vectors transfected in E. coli is also useful. Examples of such markers include genes specifying resistance to ampicillin, tetracycline, or chloramphenicol. See, Sambrook, et al. for details concerning selection markers for use in E. coli.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for clone 22 proteins are available using E. coli, Bacillus sp. and Salmonella (Palva, et al., Gene 22:229–235 (1983); Mosbach, et al., Nature 302:543–545 (1983)).

When expressing clone 22 or IMP.18p proteins in S. typhimurium, one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the S. typhimurium, the foreign gene is incorporated into the chromosome by homologous recombination between the flanking sequences and chromosomal DNA.

An example of how this can be achieved is based on the his operon of Salmonella. Two steps are involved in this process. First, a segment of the his operon must be deleted in the Salmonella strain selected as the carrier. Second, a plasmid carrying the deleted his region downstream of the gene encoding the clone 22 or IMP.18p protein is transfected into the his Salmonella strain. Integration of both the his sequences and a gene encoding a clone 22 or IMP.18p protein occurs, resulting in recombinant strains which can be selected as $his^+$.

Recombinant proteins are expressed by transformed bacteria in large amounts, typically after promoter induction; but expression can be constitutive. Bacteria are grown according to standard procedures in the art. Because some proteins can be difficult to isolate with intact biological activity, preferably fresh bacteria cells are used for isolation of protein. Use of cells that are frozen after growth but prior to lysis typically results in negligible yields of active protein.

Detection of the expressed protein is achieved by methods known in the art and include, for example, radioimmunoassays, Western blotting techniques or immunoprecipitation.

Proteins expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of about 100–150 µg/ml lysozyme and 0.1% Nonidet P40, a non-ionic detergent. The cell suspension can be homogenized using a Polytron (Brinkman Instruments, Westbury, N.Y.). Alternatively, the cells can be sonicated on ice. Alternate methods of lysing bacteria are apparent to those of skill in the art (see, e.g., Sambrook et al., supra; Ausubel et al, supra).

The cell suspension is generally centrifuged and the pellet containing the inclusion bodies resuspended in buffer that does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties); the proteins that formed the inclusion bodies may then be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of immunologically and/or biologically active protein. After solubilization, the protein can be separated from other bacterial proteins by standard separation techniques.

Alternatively, it is possible to purify the protein of interest from bacteria periplasm. Where IMP.18p or clone 22, for example, is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art. Purification from E. coli can also be achieved following procedures described in U.S. Pat. No. 4,511,503.

2. Expression in Eukaryotes

A variety of eukaryotic expression systems such as yeast, insect cell lines, bird, fish, frog, and mammalian cells, are known to those of skill in the art. As explained briefly below, the isolated proteins of the present invention may be expressed in these eukaryotic systems.

Yeast expression systems, being eukaryotic, provide an attractive alternative to bacterial systems for some applications, for an overview of yeast expression systems, see *Protein Engineering Principles and Practice*, eds. Cleland et al., Wiley-Liss, Inc. p 129 (1996). A variety of yeast vectors are publicly available. For example, the expression vector pPICZ B (Invitrogen, San Diego, Calif.) can be used to express the protein of the invention in yeast, such as *Pichia pastoris*. Yeast episomal plasmids comprising inducible promoters can be used for the intracellular expression of proteins the invention. Vectors include the pYES2 expression vector (Invitrogen, San Diego, Calif.) and pBS24.1 (Boeke (1984) *Mol. Gen. Gene.* 197:345); see also Jacobs (1988) *Gene* 67:259–269. Yeast promoters for yeast expression vectors suitable for exogenous protein expression include the inducible promoter from the alcohol dehydrogenase gene, ADH2, also called the yeast alcohol dehydrogenase II gene promoter (ADH2P). The protein of interest can be fused at the amino terminal end to the secretion signal sequence of the yeast mating pheromone alpha-factor (MF alpha 1S) and fused at the carboxy terminal end to the alcohol dehydrogenase II gene terminator (ADH2T), see van Rensburg (1997) *J. Biotechnol.* 55:43–53. The yeast alpha mating pheromone signal sequence allows for secretion of the expressed polypeptide. Direct intracellular expression of IMP.18p is usefuil for a variety of cell-based screens for activity and modulators of enzyme activity.

Yeast strains which can be used to express exogenous nucleic acids include *Pichia pastoris, Hansenula polymorpha, Torulopsis holmil, Saccharomyces fragilis, Saccharomyces cerevisiae, Saccharomyces lactis,* and *Candida pseudotropicalis*. A large number of vectors are available for *S. cerevisiae. Kluyveromyces lactis,* and the methylotrophs *Hansenula polymorpha* and *Pichia pastoris* offer certain advantages over baker's yeast *S. cerevisiae* for the production of certain proteins, see Gellissen (1997) *Gene* 190:87–97; Wegner (1990) *FEMS Microbiol. Rev.* 87:279.

Synthesis of heterologous proteins in yeast is well known. *Methods in Yeast Genetics*, Sherman, F., et al., Cold Spring Harbor Laboratory, (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., 1979, *Gene*, 8:17–24; Broach, et al., (1979), *Gene*, 8:121–133).

Two procedures are used in transfecting yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, (1978), *Nature* (London), 275:104–109; and Hinnen, A., et al. (1978), *Proc. Natl. Acad. Sci. USA*, 75:1929–1933. The second procedure does not involve removal of the cell wall. Instead the cells are treated with lithium chloride or acetate and PEG and put on selective plates (Ito, H., et al. (1983), *J. Bact.*, 153:163–168).

Clone 22 proteins or IMP.18p, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding clone 22 or IMP.18p proteins can also be ligated to various expression vectors for use in transfecting cell cultures of, for instance, mammalian, insect, bird, amphibian, or fish origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the CHO cell lines, and various human cells such as COS cell lines, HeLa cells, myeloma cell lines, Jurkat cells. Other animal cells useful for production of IMP18.p and clone 22 proteins are available, for instance, from the American Type Culture Collection Catalogue of Cell Lines and Hybridomas (7th edition, 1992).

Expression vectors for these cells can include expression control sequences, such as an origin of replication, a promoter (e.g., the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. The expression vector typically contains a transcription unit or "expression cassette" that contains all the additional elements required for the expression of the IMP18.p or clone 22 encoding DNA in host cells. A typical expression cassette thus contains a promoter operably linked to the DNA sequence encoding protein coding sequence and signals required for efficient polyadenylation of the transcript, ribosome binding sites, and translation termination.

The DNA sequence encoding the IMP18.p and clone 22 proteins can typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*.

Additional elements of the expression cassette may include enhancers and, if genomic DNA is used as the structural gene, introns with functional splice donor and acceptor sites.

Appropriate vectors for expressing clone 22 or IMP.18p proteins in insect cells are usually derived from the SF9 baculovirus. Suitable insect cell lines include mosquito larvae, silkworm, armyworm, moth and Drosophila cell lines such as a Schneider cell line (See Schneider *J. Embryol. Exp. Morphol.* 27:353–365 (1987).

As indicated above, the vector, e.g., a plasmid, which is used to transfect the host cell, preferably contains DNA sequences to initiate transcription and sequences to control the translation of the protein. These sequences are referred to as expression control sequences.

As with yeast, when higher animal host cells are employed, polyadenlyation or trnnsription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VPI intron from SV40 (Sprague, J. et al., (1983), *J. Virol.* 45: 773–781).

Expression vectors containing regulatory elements from eukaryotic viruses are typically used in eukaryotic expression vectors, e.g., SV40 vectors, papilloma virus vectors, and vectors derived from Epstein Bar virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells. Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach* Ed. D. M. Glover, IRL Press, Arlington, Va. pp. 213–238.

Some expression systems have markers that provide gene amplification such as thymidine kinase, hygromycin B phosphotransferase, and dihydrofolate reductase. Gene amplification, whether by higher vector copy number or by replication of a gene in a chromosome, can increase yields of recombinant proteins in mammalian and other cells. One in vitro amplification method for heterologous gene expression in mammalian cells is based on the stable transfection of cells with long, linear DNA molecules having several copies of complete expression units, coding for the gene of interest, linked to one terminal unit coding for a selectable marker. As another example, gene amplification of the gene of interest can be achieved by linking it to a dihydrofolate reductase (Dhfr) gene and administering methotrexate to the transfected cells; this method can increase recombinant protein production many fold (see Monaco (1996) *Gene* 180:145–150).

Alternatively, high yield expression systems not involving gene amplification are also suitable, such as using a baccu-lovirus vector in insect cells, with for example an IMP.18p encoding sequence under the direction of the polyhedrin promoter or other strong baculovirus promoters. A commonly used insect system utilizes *Spodoptera frugiperda* infected with a baculovirus, such as *Autographa californica* nuclear polyhedrosis virus. This virus can be used to infect Sf21 (Deutschmann (1994) *Enzyme Microb Technol* 16:506–512) or Sf9 cells (MaxBac 2.0, Invitrogen, San Diego, Calif.) (Zhu (1996) *J Virol Methods* 62(1), 71–79) derived from *Spodoptera frugiperda*, High Five cells derived from *Trichoplusia ni* insect cells (Parrington (1997) *Virus Genes* 14(1), 63–72), and *Lymantria dispar* (Vaughn (1997) *In Vitro Cell Dev Biol Anim* 33:479–482); see also Grabherr (1997) *Biotechniques* 22: 730–735). Baculovirus transfer vectors can be used to replace the wild-type AcM-NPV polyhedron gene with a heterologous gene of interest. Sequences that flank the polyhedrin gene in the wild-type genome are positioned 5' and 3' of the expression cassette on the transfer vectors. Following cotransfection with AcM-NPV DNA, a homologous recombination event occurs between these sequences resulting in a recombinant virus carrying the gene of interest and the polyhedrin p10 or ppromoter. Baculovirus expression vectors are publicly available, such as pAC360 (Invitrogen, San Diego, Calif.). In addition to manufacturer s instructions accompanying the commercially available baculovirus systems, see "Current Protocols in Molecular Biology," Ausubel, Chapter 16.

The host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and micro-injection of the DNA directly into the cells. The transfected cells are cultured by means well known in the art. *Biochemical Methods in Cell Culture and Virology*, Kuchler, R. J., Dowden, Hutchinson and Ross, Inc., (1977). The expressed proteins are recovered by well known mechanical, chemical or enzymatic means.

The clone 22 or IMP.18p proteins of the present invention which are produced by recombinant DNA technology may be purified by standard techniques well known to those of skill in the art. Recombinantly produced clone 22 or IMP.18p proteins can be directly expressed or expressed as a fusion protein. The recombinant clone 22 or IMP.18p protein can be purified by a combination of cell lysis (e.g., sonication) and affmiity chromatography. For fusion products, subsequent digestion of the fusion protein with an appropriate proteolytic enzyme releases the desired recombinant clone 22 or IMP.18p protein.

The clone 22 or IMP.18p proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982); Deutscher, Guide to Protein Purification, Academic Press, 1990. For example, antibodies may be raised to the clone 22 or IMP.18p proteins as described herein. The protein may then be isolated from cells expressing the recombinant clone 22 or IMP.18p protein and further purified by standard protein chemistry techniques as described above.

Antibodies

The present invention provides antibodies specifically reactive, under immunologically reactive conditions, to an isolated protein of the present invention. Antibodies are raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated.

Many methods of making antibodies are known to persons of skill. The following discussion is presented as a general overview of the techniques available; however, one of skill will recognize that many variations upon the following methods are known.

A. Antibody Production

A number of immunogens are used to produce antibodies immunologically reactive with a clone 22 or IMP.18p protein. An isolated recombinant, synthetic, or native clone 22 protein of 5 contiguous amino acids in length or greater from SEQ ID NO:3 or 4 is the preferred immunogens (antigen) for the production of anti-clone 22 polypeptide monoclonal or polygonal antibodies. An isolated recombinant, synthetic, or native IMP.18p protein of 5 contiguous amino acids in length or greater from SEQ ID NO:17 is the preferred immunogens (antigen) for the production of anti-IMP.18p polypeptide monoclonal or polyclonal antibodies. In one class of preferred embodiments, an immunogenic protein conjugate is also included as an immunogen. Naturally occurring clone 22 or IMP.18p proteins are also used either in pure or impure form.

The clone 22 or IMP.18p protein is then injected into an animal capable of producing antibodies. Either monoclonal or polyclonal antibodies can be generated for subsequent use in immunoassays to measure the presence and quantity of the clone 22 or IMP.18p protein. Methods of producing polyclonal antibodies are known to those of skill in the art.

In brief, an immunogen (antigen), preferably a purified clone 22 or IMP.18p protein, a clone 22 or IMP.18p protein coupled to an appropriate carrier (e.g., GST, keyhole limpet hemanocyanin, etc.), or a clone 22 or IMP.18p protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the clone 22 or IMP.18p protein of interest. When appropriately high titers of antibody to the immunogen are obtained, blood is collected from the animal and antisera are prepared. Further fractionation of the antisera to enrich for antibodies reactive to the clone 22 or IMP. 18p protein is performed where desired (see, e.g., Coligan (1991) *Current Protocols in Immunology* Wiley/Greene, N.Y.; and Harlow and Lane (1989) *Antibodies: A Laboratory Manual* Cold Spring Harbor Press, N.Y.).

Antibodies, including binding fragments and single chain recombinant versions thereof, against predetermined fragments of clone 22 or IMP.18p protein are raised by immunizing animals, e.g., with conjugates of the fragments with carrier proteins as described above. Typically, the immunogen of interest is a clone 22 or IMP.18p protein of at least about 5 amino acids, more typically the clone 22 or IMP.18p protein is at least 10 amino acids in length, preferably, at least 15 amino acids in length, more preferably at least 25 amino acids in length. In particularly preferred embodiments, the immunogen is derived from the extra- or intra-cytoplasmic region of the clone 22 protein. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a clone 22 or IMP.18p protein from which the immunogen was derived. Specific monoclonal and polyclonal antibodies will usually bind with an affinity constant of at least between $10^{-6}$ to $10^{-7}$ M, preferably at least $10^{-8}$ M, preferably at least $10^{-9}$ M, more preferably at least $10^{-10}$ M, most preferably at least $10^{-11}$ M.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen comprising a clone 22 or IMP.18p protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transfection with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The clone 22 or IMP.18p proteins and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246: 1275–1281; and Ward, et al. (1 989) *Nature* 341: 544–546; and Vaughan et al. (1 996) *Nature Biotechnology*, 14: 309–314). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845–851 (1996).

Frequently, the clone 22 or IMP.18p proteins and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant inmmunoglobulins may be produced. See, Cabilly, U.S. Pat. No. 4,816,567; and Queen et al. (1989) *Proc. Nat'l Acad. Sci. USA* 86: 10029–10033.

The antibodies of this invention are also used for affinity chromatography in isolating clone 22 or IMP.18p protein. Columns are prepared, e.g., with the antibodies linked to a solid support, e.g., particles, such as agarose, Sephadex, or the like, where a cell lysate is passed through the column, washed, and treated with increasing concentrations of a mnild denaturant, whereby purified clone 22 or IMP.18p protein are released.

The antibodies can be used to screen expression libraries for particular expression products such as normal or abnormal human clone 22 or IMP.18p proteins. Usually the antibodies in such a procedure are labeled with a moiety allowing easy detection of presence of antigen by antibody binding. Antibodies raised against a clone 22 or IMP.18p protein can also be used to raise anti-idiotypic antibodies. These are useful for detecting or diagnosing various pathological conditions related to the presence of the respective antigens.

B. Human or Humanized (Chimeric) Antibody Production

The anti-clone 22 or anti-IMP.18p protein antibodies of this invention can also be administered to a mammal (e.g., a human patient) for therapeutic purposes (e.g., as targeting molecules when conjugated or fused to effector molecules such as labels, cytotoxins, enzymes, growth factors. drugs, etc.). Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

i) Humanized (Chimeric) Antibodies

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos: 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

ii) Human Antibodies

In another embodiment, this invention provides for fully human anti-clone 22 or anti-IMP.18p protein antibodies. Human antibodies consist entirely of characteristically human polypeptide sequences. The human anti-clone 22 or anti-IMP.18p protein antibodies of this invention can be produced in using a wide variety of methods (see, e.g., Larrick et al., U.S. Pat. No. 5,001,065, for review).

In preferred embodiments, the human anti-clone 22 or anti-IMP.18p protein antibodies of the present invention are usually produced initially in trioma cells. Genes encoding the antibodies are then cloned and expressed in other cells, particularly, nonhuman mammalian cells. The general approach for producing human antibodies by trioma technology has been described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

The genes encoding the heavy and light chains of immunoglobulins secreted by trioma cell lines are cloned according to methods, including the polymerase chain reaction, known in the art (see, e.g., Sambrook et al., *Molecular Cloning: A Laboratory Manual*, 2nd ed., Cold Spring Harbor, N.Y., 1989; Berger & Kimmel, *Methods in Enzymology*, Vol. 152: *Guide to Molecular Cloning Techniques*, Academic Press, Inc., San Diego, Calif., 1987; Co et al. (1992) *J. Immunol.*, 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Clone 22 and IMP.18p Protein Immunoassays

Embodiments include means of detecting the clone 22 or IMP.18p proteins of the present invention using novel reagents provided for by the invention. In one embodiment, the clone 22 or IMP.18p proteins are detected and/or quantified using the novel antibodies provided for by the invention utilizing any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte (in this case clone 22 or IMP.18p protein). The capture agent is a moiety that specifically binds to the analyte. In a preferred embodiment, the capture agent is an antibody that specifically binds a clone 22 or IMP.18p protein(s). The antibody (anti-clone 22 or anti-IMP.18p protein antibody) may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled clone 22 or IMP.18p protein or a labeled anti-clone 22 or anti-IMP.18p protein antibody. Alternatively, the labeling agent may be a third moiety, such as another antibody, that specifically binds to the antibody/clone 22 protein complex.

In some embodiments, the labeling agent is a second clone 22 or IMP.18p protein antibody bearing a label. Alternatively, the second clone 22 or IMP. 18p protein antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401–1406, and Akerstrom, et al. (1985) *J. Immunol.*, 135: 2589–2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a clone 22 or IMP.18p protein in a biological sample generally comprises the steps of contacting the biological sample with an antibody which specifically reacts, under immunologically reactive conditions, to the clone 22 or IMP.18p protein. The antibody is allowed to bind to the clone 22 or IMP.18p protein under immunologically reactive conditions, and the presence of the bound antibody is detected directly or indirectly.

A. Non-Competitive Assay Formats

Immunoassays for detecting clone 22 or IMP.18p proteins of the present invention include competitive and noncompetitive formats. Noncompetitive immunoassays are assays in which the amount of captured analyte (in this case clone 22 or IMP.18p protein) is directly measured. In one preferred "sandwich" assay, for example, the capture agent (anti-clone 22 or anti-IMP.18p protein antibodies) can be bound directly to a solid substrate where they are immobilized. These immobilized antibodies then capture clone 22 or IMP.18p protein present in the test sample. The clone 22 or IMP.18p protein thus immobilized is then bound by a labeling agent, such as a second human clone 22 or IMP.18p protein antibody bearing a label. Alternatively, the second clone 22 or IMP.18p protein antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte (clone 22 or IMP.18p protein) present in the sample is measured indirectly by measuring the amount of an added (exogenous) analyte (clone 22 or IMP.18p protein) displaced (or competed away) from a capture agent (anti clone 22 or IMP.18p protein antibody) by the analyte present in the sample. In one competitive assay, a known amount of, in this case, clone 22 or IMP.18p protein is added to the sample and the sample is then contacted with a capture agent, in this case an antibody that specifically binds clone 22 or IMP.18p protein. The amount of clone 22 or IMP.18p protein bound to the antibody is inversely proportional to the concentration of clone 22 or IMP.18p protein present in the sample.

In some embodiments, the antibody is immobilized on a solid substrate. The amount of clone 22 or IMP.18p protein bound to the antibody may be determined either by measuring the amount of clone 22 or IMP.18p protein present in a clone 22 or IMP.18p protein/antibody complex, or alternatively by measuring the amount of remaining uncomplexed clone 22 or IMP.18p protein. The amount of clone 22 or IMP.18p protein may be detected by providing a labeled clone 22 or IMP.18p protein molecule.

A hapten inhibition assay is another preferred competitive assay. In this assay a known analyte, in this case clone 22 or IMP.18p protein is immobilized on a solid substrate. A known amount of anti-clone 22 or anti-IMP.18p protein antibody is added to the sample, and the sample is then contacted with the immobilized clone 22 or IMP.18p protein. In this case, the amount of anti-clone 22 or anti-IMP.18p protein antibody bound to the immobilized clone 22 or IMP.18p protein is inversely proportional to the amount of clone 22 or IMP.18p protein present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format are also used for crossreactivity determinations to permit one of skill to determine if a novel protein is a homologue, allele, or polymorphic variant of the IMP.18p polypeptide having the sequence set forth as SEQ ID NO:17, thus falling within the scope of the claimed invention. In this assay, the IMP.18p polypeptide with the sequence set forth as SEQ ID NO:17 is immobilized to a solid support. Putative IMP.18p polymorphic variants are added to the assay to compete with immobilized IMP.18p antigen for binding to a characterized anti-IMP.18p antisera. The ability of the putative IMP.18p polymorphic variants to compete with immobilized IMP.18p antigen for binding to the anti-IMP.18p antisera is compared to the ability of IMP.18p of SEQ ID NO:17, or immunogenic fragments thereof, to compete with immobilized antigen for binding to the antisera. The percent crossreactivity for the above proteins is calculated, using standard calculations.

To prepare the antisera for use in this competitive binding immunoassay, all IMP cross-reacting antibodies are first removed by immuno-absorption with known IMP polypeptides. Specifically, antisera are immunosorbed with the human IMP (huIMP) defined by McAllister (1992) *Biochem J.* 284:749–754, GenBank Accession #P29218; bovine IMP defined by York (1990) *Proc. Natl. Acad. Sci. USA* 87:9548–9552, GenBank Accession #P21327; and, rat IMP as defined by Parthasarathy (1997) *Gene* 191:81–87, GenBank Accession #U84038. Antisera with less than 10% crossreactivity with non-IMP.18p/SEQ ID NO:17 polypeptides are selected and pooled (i.e., 90% of the antisera is non-cross reactive, thus specific). Thus, the anti-IMP.18p antibodies and antisera of the invention have less than 10% cross-reactivity to (e.g., as they are immunosorbed against) previously characterized anti-IMP polypeptides, as discussed above. The immunoabsorbed antisera are used in a competitive binding immunoassay, as described below, to analyze whether an uncharacterized protein is an IMP.18p protein within the scope of the claimed invention.

In this competitive binding immunoassay, the IMP.18p protein of SEQ ID NO:17 competes with a second, putative IMP.18p polymorphic variant in an antibody binding reaction. The known and uncharacterized IMP.18p polypeptides are competitively reacted with antisera developed against and specifically reactive with the IMP.18p of SEQ ID NO:17 (antisera immunosorbed to ensure no cross-reactivity with previously characterized IMPs, as described above). The two polypeptides are each assayed at a wide range of concentrations. The amount of each polypeptide required to inhibit 50% of the binding of the anti-IMP.18p (SEQ ID NO:17) antisera to immobilized IMP.18p (SEQ ID NO:17) polypeptide is determined. If the amount of the second (uncharacterized) protein required is less than 10 times the amount of the characterized immunogen (IMP.18p/SEQ ID NO:17) that is required, then the second protein is said to specifically bind to an antibody generated to the characterized (IMP.18p/SEQ ID NO:17) immunogen.

Immunoassays in the competitive binding format can be used for crossreactivity determinations to permit one of skill to determine if a novel anti-IMP.18p antibody or antisera is sufficiently related to the anti-IMP.18p polypeptide of the invention with the sequence set forth as SEQ ID NO:17 so as to fall under (within the scope of) the claims of this invention. For example, the IMP.18p/SEQ ID NO:17 polypeptide is immobilized to a solid support. Test antibodies are added to the assay to compete with the binding of the known anti-IMP18.p/SEQ ID NO:17 antisera to the immobilized antigen (IMP.18p/SEQ ID NO:17). The ability of the test antisera to compete with the binding of the known antisera to the immobilized IMP.18p is compared. The percent crossreactivity for the above antibodies is calculated, using standard calculations.

C. Other Assay Formats

In other embodiments, Western blot (immunoblot) analysis is used to detect and quantify the presence of clone 22 or IMP.18p protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind clone 22 or IMP.18p protein. The anti-clone 22 or anti-IMP.18p protein antibodies specifically bind to clone 22 or IMP.18p protein, respectively, on the solid support. These antibodies may be directly labeled or alternatively may be subsequently detected using labeled antibodies (e.g., labeled sheep anti-mouse antibodies) that specifically bind to the anti-clone 22 or anti-IMP.18p protein.

Assaying for Activity and Modulators of IMP.18p Myo-Inositol Monophosphatase

The invention also provides for means to assay the activity of the novel IMP18.p myo-inositol monophosphatase enzyme. Using such assays, one embodiment provides for a method of determining whether a test compound is a modulator, such as an inhibitor/antagonist or agonist, of IMP.18p myo-inositol monophosphatase activity. The method involves contacting an active IMP.18p with a putative modulator test compound and measuring the activity of the IMP.18p. A change in the activity of the IMP.18p in the presence of the test compound is an indicator of whether the test compound is an antagonist or agonist/activator of IMP.18p. A variety of myo-inositol monophosphatase activity assays are known in the art which can be adapted by the skilled artisan to be used using the novel IMP.18p in the methods of the invention. Illustrative examples of such assays are set forth below.

Myo-inositol monophosphatases are major enzymes controlling the inositol intracellular signaling pathway. Numerous diacylglycerol and calcium-mobilizing enzymes are associated with this pathway, including serotonergic, muscarinic, adrenergic, metabotropic, histaminergic, cholecystokinin, tachykinin, bombesin, neurotensin and bradykinin receptors, to name a few examples. Activation of these receptors activates GTP binding proteins, which results in the phospholipase C hydrolysis of inositol-phospholipid. This reaction releases two intracellular messengers: myo-inositol 1,4,5-triphosphate (IP3) and diacylglycerol (DAG). IP3 releases intracellular calcium stores, which in turn activates a variety of second signals. triggering numerous physiologic effects, for example, ion channel activation. Levels of IP3 are controlled by sequential dephosphorylation, the last step generating the products inositol and phosphate from the substrate myo-inositol monophosphate (myo-inositol 1-phosphate) by the enzyme myo-inositol monophosphatase. Thus, the activity of myo-inositol monophosphates can be monitored in vitro or in vivo by measuring the loss or accumulation of a substrate or a product, respectively, over time.

Monitoring the activity and assessment of potential modulators of the novel IMP.18p of the invention can be accomplished in vitro by measuring the accumulation of either myo-inositol monophosphatase product in the form of radiolabeled inositol (e.g., $^{14}$C-inositol or $^{3}$H-inositol) or inorganic phosphate (Pi) (e.g., in a colorimetric assay or as $^{32}$Pi). For example, a Pi-release assay based on calorimetric means to measure changes in Pi concentration over time can be carried out as described by Ragan (1988) *Biochem. J.* 249:143–148, or, by Vadnal (1995) *Neuropsychopharmacol.* 12:277–285.

As in Vadnal (1995) supra, the reaction mixture can consist of 0.05 ml of 120 mM Tris-HCl, pH 7.8; 0.05 ml of 18 mM or 3 mM magnesium chloride; 0.05 ml of 4.2 mM D-myo-inositol 1-phosphate, 0.125 ml water alone or with positive controls or putative modulator test compounds or compositions. Known myo-inositol monophosphatase inhibitors (antagonists), such as lithium, carbamazepine and/or valproic acid, in varying amounts can be used as controls. A 0.025 ml solution of myo-inositol monophosphatase (e.g., IMP.18p, or another myo-inositol monophosphatase as a positive control) is added and the reaction mixture is incubated at 37° C. for about 15 minutes to an hour. The reaction is stopped by the addition of 0.05 nl of 20% trichloroacetic acid (TCA). The suspension is centrifuged and 0.10 ml of supernatant is used to estimate the liberated Pi using the malachite green reagent method, as, for example, described by Eisenberg (1987) *Methods Enzymol.* 141:127–143. Protein is assayed using the method of Lowry (1951) *J. Biol. Chem.* 193:265–275. Assays are usually run in triplicate. Alternatively, as in Ragan (1988) supra, the reaction mixture can be in a final volume of 0.300 ml containing 0.1 mM substrate, 250 mM potassium chloride, 50 mM Tris HCl, pH 8.0, and 3 mM magnesium chloride for period of time from 15 minutes to one hour. Released Pi can be measured calorimetrically using the method of Itaya (1966) *Clin. Chem. Acta* 14:361–366 (see also Kodama (1986) "The initial phosphate burst in ATP hydrolysis by myosin and subfragment-1 as studied by a modified malachite green method for determination of inorganic phosphate," *J. Biochem.* (Tokyo) 99:1465–1472). The specific activity of myo-inositol monophosphatase is expressed as nanomoles of phosphate liberated per minute (mU) per milligram protein.

Kinetic activity and assessment of potential modulators of the IMP.18p of the invention can also be accomplished in vivo by measuring accumulation of the substrate myo-inositol monophosphate (myo-inositot 1-phosphate) using, for example, assays described by Atack (1993) *J. of Neurochem.* 60:652–658; or, Ragan (1988) supra. Radiolabeled inositol monophosphate accumulation can be measured in tissue culture cells expressing IMP.18p in the presence of putative myo-inositol monophosphatase antagonists, for example, as described by Atack (1993) supra. The tissue culture cells can be genetically manipulated, as described above, to express the IMP.18p of the invention, or fragments or variations thereof For example, as described above, CHO cells can be manipulated to express very large amounts of exogenous protein. Specifically, to assess the effect of a putative antagonist or agonist on myo-inositol monophosphatase in vivo, CHO cells are first prelabeled with $^{3}$H-inositol. Prelabeling involves growing cells to confluence for two days in medium containing radiolabeled inositol (e.g., $^{14}$C-inositol or $^{3}$H-inositol). If using $^{3}$H-inositol, 0.5 uCi/ml 80 Ci/mmol (Amersham International) is used. On the day of the experiment, cells are harvested in Krebs-Henseleit buffer at $2\times10^6$ cells/ml containing 0.5 uCi/ml $^{3}$H-inositol. Aliquots of the harvested cells are incubated for one hour at 37° C. in a shaking water bath in the presence of 10 ul of various concentrations of known enzyme inhibitors and test compounds—putative enzyme modulators. Assays are terminated by addition of 300 ul of 1.0 M TCA and centrifuged. 500 ul of supemnatant is washed with water-saturated diethyl ether. The pH is adjusted to about 7.0 using 1 M Tris. The supernatants are then applied to Dowex columns. Columns are washed four times with 5 ml of water to elute free $^{3}$H-inositol; then washed three times with 5 ml of 25 mM arnmonium formate to elute beta-glycerophosphates. $^{3}$H-inositol 1-monophosphate is collected by washing the column with 10 ml of 200 mM ammonium phosphate and counted on a scintillation counter. Alternatively, $^{14}$C-inositol can be used, as described by Ragan (1988) supra. Inhibition of the myo-inositol monophosphatase will result in increased levels of the substrate myo-inositol monophosphate (myo-inositol 1-phosphate), while activation of the enzyme will result in decreased levels of substrate and increased levels of product (inositol and inorganic phosphate).

Using these assays and variations thereof, the kinetics of the IMP.18p enzyme with and without test modulators (e.g., competitive or non-competitive antagonists) can be analyzed using known methods (e.g., Lineweaver-Burke plots, as used, for example by Lee (1996) *Xenobiotica* 26: 831–838); for discussion on enzyme kinetic analysis generally see, for example, Suarez (1997) *Proc. Natl. Acad. Sci. USA* 94:7065–7069; Northrop (1997) *Bioorg. Med. Chem.* 5:641–644); Sterrer (1997) *J. Recept. Signal Transduct. Res.* 17:511–520).

Higih-Throughput Screening of Candidate IMP.18p Modulators

Conventionally, new chemical entities with useful properties are generated by identifying a chemical compound (called a "lead compound") with some desirable property or activity (in this case, e.g., an antagonist or agonist of IMP.18p), creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic or diagnostic compounds (candidate compounds). Such "combinatorial chemical libraries" are then screened in one or more assays, some of which are described above, to identify those library members (particular chemical species or subclasses) that display the desired characteristic activity (e.g., modulation of the activity of IMP.18p). The compounds thus identified can serve as conventional "lead compounds" or can themselves be used as potential or actual therapeutics. See also, van Breemen (1997) *Anal Chem* 69:2159–2164; Lam (1997) *Anticancer Drug Des* 12:145–167 (1997).

a. Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487–493, Houghton et al. (1991) *Nature*, 354: 84–88).

Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad Sci. USA* 90: 6909–6913), vinylogous polypeptides (Hagihara et al. (1992) *J. Amer. Chem. Soc.* 114: 6568), nonpeptidal peptidomimetics with a Beta- D- Glucose scaffolding (Hirschmann et al., (1992) *J. Amer. Chem. Soc.* 114: 9217–921 8), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries, peptide nucleic acid libraries (see, e.g., U.S. Pat. No. 5,539,083) antibody libraries (see, e.g., Vaughn et al. (1996) *Nature Biotechnology*, 14(3): 309–314), and PCT/US96/10287), carbohydrate libraries (see, e.g., Liang et al. (1996) *Science*, 274: 1520–1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. Nos. 5,506, 337, benzodiazepines 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif.; 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton. N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

b. High throughput assays of chemical libraries

Any of the assays for compounds inhibiting the virulence described herein are amenable to high throughput screening. As described above, having identified the nucleic acid associated with virulence, likely drug candidates either inhibit expression of the gene product, or inhibit the activity of the expressed protein. Preferred assays thus detect inhibition of transcription (i.e., inhibition of mRNA production) by the test compound(s), inhibition of protein expression by the test compound(s), or binding to the gene (e.g., gDNA, or cDNA) or gene product (e.g., mRNA or expressed protein) by the test compound(s). Alternatively, the assay can detect inhibition of the characteristic activity of the gene product or inhibition of or binding to a receptor or other transduction molecule that interacts with the gene product.

High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high thruput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Rational Drug Design

Potential modulators of enzyme activity can also be investigated utilizing "rational drug design" approaches. This involves an integrated set of methodologies that include structural analysis of target molecules, synthetic chemistries, and advanced computational tools. When used to design modulators, such as antagonists/inhibitors of protein targets, such as IMP.18p polypeptides, the objective of rational drug design is to understand a molecule's three-dimensional shape and chemistry. Rational drug design is aided by X-ray crystallographic data or NMR data, which can now be determined for the IMP.18p polypeptide in accordance with the methods and using the reagents provided by the invention. Calculations on electrostatics, hydrophobicities and solvent accessibility is also helpful. See, for example, Coldren (1997) *Proc. Natl. Acad. Sci. USA* 94:6635–6640.

Inhibitory Natural Compounds as Modulators of IMP.18p Activity

In addition, a large number of potentially useful activity-modifying compounds can be screened in extracts from natural products as a source material. Sources of such extracts can be from a large number of species of fungi, actinomyces, algae, insects, protozoa, plants, and bacteria. Those extracts showing inhibitory activity can then be analyzed to isolate the active molecule. See for example, Turner (1996) *J Ethnopharmacol* 51(1–3):39–43; Suh (1995) *Anticancer Res* 15:233–239.

Inhibitory Oligonucleotides

One particularly useful set of inhibitors provided by the present invention includes oligonucleotides which are able to either bind mRNA encoding IMP.18p or clone 22 polypeptides or to their corresponding genes. In either case, these oligos prevent or inhibit the production of functional protein.

Another useful class of inhibitors includes oligonucleotides which cause inactivation or cleavage of IMP.18p or clone 22 mRNA. That is, the oligonucleotide is chemically modified or has enzyme activity which causes such cleavage, such as ribozymes. As noted above, one may screen a pool of many different such oligonucleotides for those with the desired activity.

Another useful class of inhibitors includes oligonucleotides which bind polypeptides. Double- or single-stranded DNA or single-stranded RNA molecules that bind to specific polypeptides targets are called "aptamers." The specific oligonucleotide-polypeptide association may be mediated by electrostatic interactions. For example, aptamers specifically bind to anion-binding exosites on thrombin, which physiologically binds to the polyanionic heparin (Bock (1992) *Nature* 355:564–566). Because the present invention provides proteins in purified form in large quantities, those of skill in the art can readily screen for IMP.18p-binding aptamers using the methods of the invention.

Antisense Oligonucleotides

IMP.18p or clone 22 activity can be inhibited by targeting their respective mRNA with antisense oligonucleotides capable of binding the mRNA. In some situations, naturally occurring nucleic acids used as antisense oligonucleotides may need to be relatively long (18 to 40 nucleotides) and present at high concentrations. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) *Toxicol Appl Pharmacol* 144:189–197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

As noted above, combinatorial chemistry methodology can be used to create vast numbers of oligonucleotides that can be rapidly screened for specific oligonucleotides that have appropriate binding affinities and specificities toward any target, such as the IMP.18p of the invention, can be utilized (for general background information Gold (1995) *J. of Biol. Chem.* 270:13581–13584).

Inhibitory Ribozymes

Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule has complementarity to the target, such as the mRNA encoding IMP.18p.

The enzymatic ribozyme RNA molecule is able to cleave RNA and thereby inactivate a target RNA molecule. The complementarity functions to allow sufficient hybridization of the enzymatic ribozyme RNA molecule to the target RNA for cleavage to occur. One hundred percent complementarity is preferred, but complementarity as low as 50–75% may also be employed. The present invention provides ribozymes targeting any portion of the coding region for an IMP.18p or clone 22 gene that cleaves their corresponding mRNA in a manner that will inhibit the translation of the mRNA and thus reduce enzymatic activity. In addition, the invention provides ribozymes targeting the nascent RNA transcript of the IMP.18p or clone 22 gene to reduce activity.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) *Aids Research and Human Retroviruses* 8:183; hairpin motifs by Hampel (1989) *Biochemistry* 28:4929, and Hampel (1990) *Nuc. Acids Res.* 18:299; the hepatitis delta virus motif by Perrotta (1992) *Biochemistry* 31:16; the RNaseP motif by Guerrier-Takada (1983) *Cell* 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

Although the present invention has been described in some detail by way of illustration and example for purposes of clarity of understanding, it will be obvious that certain changes and modifications may be practiced within the scope of the appended claims.

EXAMPLES

The following examples are offered to illustrate, but not to limit the claimed invention.

Example 1

Chromosome 18-Specific Cosmid Clones Used for cDNA Selection

A human chromosome 18-specific cosmid library, LL18NC02, was provided by the Human Genome Center at the Lawrence Livermore Laboratory. The source of the chromosomes was a human/hamster hybrid cell line X11-4A (Chang et al., *Genomics*, 17:393–402, 1993; Trask et al., *Somat Cell Mol Gene*, 17:117–136, 1991) retaining a single copy of chromosome 18 as its sole human material. The chromosomal DNA was partially digested with MboI, dephosphorylated, then ligated into the BamHI site of the cosmid vector Lawrist 16 (Little, PFR (1987): *Choice and use of cosmid vectors*. In Glover DM (ed): "*Gene Cloning*" Vol. 3, IRL Press: Oxford, pp 19–42). The resulting arrayed library contained 145 96-well microtiter plates. A human genomic DNA probe hybridized to 84% of the clones in the library, 10% were positive with a rodent probe and the remaining 6% were non-recombinants since they failed to hybridize with either probe. The chromosome 18 cosmid library represents 467 Mb [13,920 clones ×84% ×40 kb (assumed average size of cosmid insert)] in chromosomal coverage. Ten pools of the library were prepared by combining the contents of all wells from plates 1–10 (pool 1), 11–25 (pool 2), 26–40 (pool 3), etc. Cultures of the cosmid pools were grown in LB/kanamycin and the DNA isolated using the Qiagen plasmid kit (Qiagen). The DNA was biotinylated for 20 minutes using the Bio-Nick kit (GIBCO-BRL). The unincorporated nucleotides were excluded by ethanol precipitation.

Example 2

Preparation of Primary cDNA

Total RNA was extracted from five regions of postmortem human brain (caudate, putarnen, hippocampus, amygdala, frontal cortex) and from human placenta by acid-guanidine, phenol/chloroform method (Chomzynski and Sacchi, *Anal Biochem*, 162:156–159, 1987). Poly(A)+ RNA was prepared using oligo(dT)-parainagnetic beads (Dynal), and double stranded cDNA was synthesized with random priming using the Invitrogen Copy kit. The cDNA was subdivided into eight pools, each containing 1 µg of brain-derived cDNA and 0.8 µg of placental cDNA. A batch of total human brain poly(A)+ RNA was purchased from Clontecti (in order to represent regions of the brain not included above), and 4 µg of double stranded EDNA was prepared as above. Each cDNA pool was ligated to an adaptor consisting of complementary oligonucleotides 1 and 2 (Lovett, *Proc Natl Acad Sci USA*, 88:9628–9632, 1994). Since the brain tissues obtained were frozen following a postmortem delay, placental cDNA was added in the selection to retain transcripts (common to both brain and placenta) that might have been labile during this delay.

Example 3

Direct cDNA Selection

Direct cDNA selection was performed using the magnetic bead capture technique described previously (Lovett et al., *Proc Natl Acad Sci USA*, 88:9628–9632, 1991; Lovett, "Current Protocols in Human Genetics" Vol. 1, John Wiley & Sons Inc: New York, pp 6.3.1–6.3.15, 1994) to a $Cot_{1/2}$ of 100, with some modifications. Briefly, repeats were blocked by mixing the starting cDNA pool with a mixture of low molecular weight Cot-1 DNA (2 µg per hybridization, GIBCO-BRL), high molecular weight Cot-1 DNA (20 ng per hybridization, GIBCO-BRL) and linearized cosmid vector DNA (30 ng per hybridization). The first round of selection was performed by hybridization of cDNA pools (1.8–2 µg each) and biotinylated cosmid pools (120 ng each). A second round of selection was conducted using 2 µg of amplified primary-selected cDNA and 120 ng of each biotinylated pool of cosmids. The PCR reactions for the primary- and secondary-selected cDNAs were performed using Expand Long Template PCR System (Boehringer Mannheim) with an initial denaturation at 94EC for 3 min, followed by 10 cycles of amplification at 94EC for 10 sec, 60EC for 30 sec and 68EC for 3 min, and 25 cycles using the same denaturation and annealing conditions, and an auto-extended elongation time of an additional 15 sec after every cycle.

Example 4

Hybridization of High Density Filters of a Normalized Infant Brain cDNA Library

Approximately 40,000 clones from a normalized infant brain library constructed by Soares et al. (1994), *Proc Natl Acad Sci USA*, 91:9228–9232, were previously arrayed at the Lawrence Livermore Laboratory into 408 96-well microtiter plates. We re-arrayed the library into 102 3 84-well microtiter plates and high density filters were produced (service done by Research Genetics, Inc). One 22×22 cm filter contained 36,864 clones and the remaining 2,304 clones were spotted on another filter.

Each pool of amplified secondary-selected eDNA was labeled with gamma-$^{32}$P-dCTP by random primer labeling (Boehringer Mannheim kit). One set of hybridizations of the high density filters was done using a mixture of all the pools of labeled secondary selected cDNA, after a preblocking procedure using total human placental DNA, low molecular weight Cot-1, and linearized cosmid vector. Hybridization was done using 2×10$^6$ cpm of preblocked cDNA per ml of Rapid-hyb buffer (Amersham) at 65EC for 2 hrs following a prehybridization of 1 hr. The final wash was in 0.1×SSC, 0.1% SDS at 60EC. Using the same conditions, a replica filter was hybridized with 5×10$^5$ cpm per ml of $^{32}$P-labeled human placental DNA.

Another set of hybridizations was performed using a mixture of two pools of secondary-selected cDNA. The hybridization pattern yielded by the secondary selected cDNAs was compared with that produced by human placental DNA. The clones corresponding to positive spots common to both filters were not picked due to the possibility that the signals were from repeat hybridization. In addition, the hybridization pattern obtained with the cDNA subpools were compared with that produced using a combination of all secondary selected cDNA pools. All high and medium intensity clones were chosen, and clones that gave low intensity signals but were comnnon to two or more filters were also picked. The insert sizes were determined using the colony PCR method described previously (Yoshikawa et al., *Biochim Biophys Acta*, 1264:63–71, 1995).

Example 5

Sequence Database Comparisons and Primer Design

The microtiter plate addresses of the positive clones chosen for further analysis were determined, and this allowed us to search the EST database (dbEST) (Boguski et al., *Nature Gene*, 4:332–333, 1993; URL:http://ncbi.nlm.nih.gov/Schuler/Unigene/Chr18.html, searched on Mar. 18, 1996) permitting the retrieval of the IMAGE cDNA ID number and corresponding Genome Database (GDB) account number. Approximately 40% of the cDNA clones contained a short 3' and/or 5' end STSs that were deposited by the sequencing collaboration of Washington University and Merck & Co. For these available sequences, primers were designed using the program PRIMER v2.2 (Resnick and Stein, Primer, v 2.2. The Whitehead Institute, Cambridge, Mass., 1995; URL: http://www-genome.wi.mit.edu), which had a Tm for primers set at between 52° C. and 55° C. (see Table 2, below).

Example 6

Mapping of eDNA Clones by PCR on Chromosome 18 Somatic Cell Hybrids

Genomic DNA was extracted from a panel of 20 somatic cell hybrids, one of which included the entire human chromosome 18 and the rest containing various segments of the chromosome (Overhauser et al., *Cytogenet Cell Gene*, 71:106–117, 1995). A diagram of the hybrids used in this study is shown in FIG. 1. Human genomic DNA and hamster genomic DNA were used as reference controls. Using this panel of chromosomal and genomic DNA as template and primer pairs derived from each clone mapping by PCR was conducted. If the initial primer pair failed to amplify, another pair was designed, or one of the primers in the original pair was modified.

PCR was performed using the Perkin Elmer Cetus Gene-Amp System 9600. Amplification was done in a 20 μl reaction containing either 80 ng (somatic cell hybrid) or 30 ng (human or hamster genomic DNA) template DNA, 5 μM of each primer, 200 μM of each dNTP and 0.75 unit of AmpliTaq (Perkin Elmer Cetus) in a standard PCR I buffer

TABLE 2

Primers used for PCR mapping.

| Clone Number | Forward | SEQ ID NO: | Reverse | SEQ ID NO: | Product Size (bp) |
|---|---|---|---|---|---|
| 1 | 5'-AGGAGTGGTGTACATTTCT-3' | 110 | 5'-ACCTGCAACACATTAGAAAC-3' | 111 | 134 |
| 2 | GGTTTCTTCAAAATTTATTAACAA | 112 | TCCTCCACTCATCTGTTTCT | 113 | 175 |
| 3 | CCTGACCTGATCAAGTTTA | 114 | GGTAAAGGAACAAGCTGC | 115 | 125 |
| 4* | TGATCACACAGTCAGCACTGT | 116 | GGGCAGAAGTTTCCAATTACC | 117 | 131 |
| 5 | TATTGAGACCTAAGTCAGCATCC | 118 | GACAGAAAGCAGGTTAGAGGT | 119 | 192 |
| 6 | GAAACTTTACATCAGGTGTCTC | 120 | ATGGACTAGGAGTTTAAGC | 121 | 283 |
| 7 | GGAACAGTGTACACTTTCC | 122 | TATATAGCCTCGATGATGAGAG | 123 | 185 |
| 8 | CATGAGAGGAAGAGGTCTTTAT | 124 | GGGTTATGTCTTAGTCGAG | 125 | 275 |
| 9 | TCAGTAGAAACTCAAGCTGCTTC | 126 | CTCCCTCTCAGTGTGAGGCT | 127 | 230 |
| 10 | CCTGACCTGATCAAGTTTAA | 128 | TGTACACCACTCCTCATGT | 129 | 179 |
| 11 | CGACGACTCATACAACATATC | 130 | GGTTACAGCTGAAGTGTAT | 131 | 177 |
| 12 | TATTCAGGAACAGTGTACAC | 132 | TCGATGATGAGAGGGTTAC | 133 | 174 |
| 13 | GAACACTTATCTCCTTCTTCAG | 134 | TCCACTCCTTTCACCTCTTCT | 135 | 243 |
| 14 | AGACAAGAGCAAAACACAAC | 136 | CTCTTTGCAGTTCAGTCTA | 137 | 169 |
| 15 | AGGIGAACCATTTGACTGGTTT | 138 | GCTTGTGTGTGGCTGTCCTT | 139 | 148 |
| 16 | GGCTAAACTTACAGTATGTAAGGAG | 140 | CTGTAAGGACAGACTACTCA | 141 | 152 |
| 17 | CCAGGAGGTTCAGCGGT | 142 | CGCAAAGCCATGAIAAACCG | 143 | 115 |
| 18$^A$ | TCAGGAACAGTGTACACTTTC | 144 | TGTGGGCTTAATACCATGTCT | 145 | 207 |
| 19 | GGAATCTCTGTACTTGCT | 146 | GTGACACATTACAAAGCCA | 147 | 154 |
| 20 | TCAGTAGAAACTCAAGCTGC | 148 | CCTCTTCCTCTTAAAGTGT | 149 | 101 |
| 21 | TCACTTCAGAATCACTACTC | 150 | ACCCATCCTATATGAAAAGC | 151 | 228 |

TABLE 2-continued

Primers used for PCR mapping.

| Clone Number | Forward | SEQ ID NO: | Reverse | SEQ ID NO: | Product Size (bp) |
|---|---|---|---|---|---|
| 22 | TACAAAAGAGGACAAAGCAC | 30 | GGTGCCTGTATATAAGTTGA | 32 | 157 |
| 23 | GGGATCATACTAAAGAGAAG | 152 | GGATAAACAGAGAGCTTGAT | 153 | 193 |
| 24 | CTACAGAATAGAATACATGGCG | 34 | GAGCTCTGAACTGTATTCAGA | 36 | 224 |
| 25 | GTCAGTTACTCTATTTGCTGTG | 154 | AACCTGTGCTGTAAAGTTCA | 155 | 233 |
| 26 | CTTAAGAGGAAGAGGCCAT | 156 | CTCTCCCTCTCAGTGTGAG | 157 | 145 |
| 27 | ACAATTAGGCATTGTTGATGG | 158 | CAGITCTTGCACATACAAGACA | 159 | 112 |
| 28 | ACCTTTGGCAAGGGGTATGA | 160 | TGTGAAGGCTGGGAAACACT | 161 | 207 |
| 29 | TCTCAGCTTACTCAACCT | 38 | GATGAGGTGGAACAATCAC | 40 | 138 |
| 30 | AACACTCAGCTCTGTAGAA | 162 | CGAGTCATCAATAGGACAA | 163 | 212 |
| 31 | GGTCTGTACAGTGTAATAAACC | 42 | CTACTGCAAAATGTGTCCTGTC | 44 | 124 |
| 32 | GAGCCAAGTGGAACTCTTGAA | 164 | GTCAGGAAAGAGGTTGTGAGC | 165 | 156 |
| 33 | ACACATATGTACACAGGAAC | 166 | TGTGTACAGCGAGTGAATTA | 167 | 103 |
| 34 | TTGTTCACACACAATCTAGG | 168 | ACTAGCATATCTGAATTCCCA | 169 | 159 |
| 35 | CTACAGAATAGAATACATGGCG | 170 | TTGAAACCAGACCCTGTAGT | 171 | 166 |
| 36 | CATTTAGTCCAGAGGCTCTT | 172 | TCCTCGAAGAGGTTGCAGC | 173 | 161 |
| 37 | CACATTAGCCAGTCTGATAAAG | 46 | AAGTTACACACAGTAGCTGA | 48 | 107 |
| 38 | CATTCAGCACACATAGAGTCTA | 174 | CCCTGTCCCTTGTATATGTA | 175 | 189 |
| 39 | AGTGTATCTACAACCTCAACTGTC | 176 | GTAAAGGCCCAATCAATGCACT | 177 | 109 |
| 40 | GCCAGATTCACAATTGATAG | 178 | CTGAAGGCACTTTATGTAC | 179 | 139 |
| 41 | CTGGAGCAGGTTAGATACACC | 180 | CTTCCCTCTTAACCTTTAGTGC | 181 | 143 |
| 42 | GTGTCTTGTATGTGCAAGAAC | 182 | GACTGGGTATCCTAGCTTAC | 183 | 157 |
| 43^ | TTAGTCAGACCCATTCAGTC | 184 | CCAGACTGCTTTATGTTAG | 185 | 103 |
| 44^ | GTGTCTTGTATGTGCAAGAAC | 186 | CCTAGCCTTACTGTTTTAAC | 187 | 146 |
| 45* | ACGATGCGATCCTGGAAG | 188 | CTGGCTTGAGTTTGTCTG | 189 | 113 |
| 46† | CCTTTCTGTGTGAAGATCAC | 190 | AAGAAAGTCCCAAGGGTGGA | 191 | 123 |
| 47† | GGAATGAGGGTTAGAGTCC | 192 | AGTGCTTCTGTAGCTCTT | 193 | 114 |
| 48* | TGAGGGTGTGAACCACTCTG | 194 | GAATCCTGGTGTGCCCAAGT | 195 | 137 |

*The 5' portion of the insert was used. The remainder were from the 3' portion.
^and † the Tm was ^ = 48° C. or † = 60° C. The remainder were 52° C.
An I in the primer sequence indicates the use of inosine for an unknown base.

(Perkin Elmer Cetus). "Touchdown" PCR was done as follows: 30 sec at 94EC, 30 sec at (T+11-n)EC (T is listed in Table 2 and n is cycle number), 1 min at 72EC for the first 10 cycles, and 30 sec at 94EC, 30 sec at TEC, 1 min at 72EC in the subsequent 25 cycles. The PCR products were separated on 3% Nusieve:Seakem agarose gels.

Example 7

Radiation Hybrid Mapping

The Stanford G3 radiation hybrid panel (Cox et al., Science, 250:245–250, 1990) (#RH01, available at Research Genetics, Inc.) was utilized to fine map the unique chromosome 18-specific brain cDNAs. This panel had a 500 kb resolution and an average of 26 kb per centiRay (cR), based on data available for chromosome 4 on 452 informative markers (http://shgc.stanford.edu/RHMap.html).

For radiation hybrid mapping, 40 ng of DNA from each of the 83 radiation hybrid cell lines were used as template, and PCR was performed with primers specific for a given cDNA clone (Table 3).

PCR was done in a 10 µl volume, and conditions were identical to those previously described for mapping with the chromosome 18 regional panel of somatic cell hybrids. Fifteen ng of human genomic DNA was used as positive control. The size of a PCR product, amplified from each radiation hybrid cell line, and a given pair of primers was determined by electrophoresis on a 3% Nusieve:Seakem agarose gel. For a given primer pair, the raw data indicating the presence or absence of an amplified product in each of the 83 radiation hybrid cell lines was submitted to the Stanford radiation hybrid e-mail server (http://shgc.stanford.edu/ rhserver/intro.html). If linkage to reference markers was found, the mapping data transmitted from Stanford included a list of linked markers (STSs), lod scores and distances in $cR_{(8000)}$. A lod score above 6 was used for assigning the unique clones to the Stanford framework map with a 95% confidence level.

Example 8 cDNA Selection and Isolation of EDNA Clones from an Infant Brain Library

To isolate brain-expressed transcripts that map specifically to chromosome 18, we performed direct cDNA selection with pools of chromosome 18 biotinylated cosmid clones and primary cDNAs derived from human brain and placenta. After two cycles of selection, the secondary selected cDNA was PCR amplified, and this was found to have an average size of about 400 bp. Longer cognate cDNA clones were isolated by using labeled amplified pools of secondary selected cDNAs to probe high density filters of an arrayed, normalized infant brain library (Soares et al., Proc Natl Acad Sci USA, 91:9228–9232, 1994). This strategy yielded a total of 174 positive cDNA clones. Analysis of the dbEST database revealed that less than half of these clones had available sequences of a few hundred bp on the 3' and/or the 5' ends.

Initially, we focused our analysis on clones that had these partial sequences to facilitate rapid chromosomal localization by PCR. The availability of these sequences also permitted comparison with sequences in the databases for homology to known genes, and evaluation of possible redundancies between the selected transcripts.

Example 9

Chromosomal Localization and Regional Mapping of Chromosome 18-Specific cDNAs To determine the chromosomal location of the positive cDNA clones we designed PCR primers from the 3' end sequence, whenever possible. Since the infant brain cDNA library was constructed by oligo (dT) priming and directional cloning this would most likely correspond to the 3' untranslated region (UTR), which is usually unique and uninterrupted by introns (Sikela and Auffray, Nature Gene 3:189–191, 1993). Primers were developed to produce PCR products of less than 300 bp. Our analysis indicated that 83% of 3' end-derived primer pairs and 74% of 5' end-derived primer pairs amplified a PCR product with the expected size.

In the initial step of the clone-based physical mapping, a panel of template DNAs was used for PCR amplification. These included: human placental DNA, somatic cell hybrid DNAs for the entire human chromosome 18 (HHW 324, FIG. 1) as well as segments (JH 353 and JH357, FIG. 2) of human chromosome 18, and hamster DNA. In addition, a number of somatic cell hybrid DNA isolates derived from other chromosomes were used as negative controls. After establishing that the cDNA was of human origin and was specifically localized to chromosome 18, mapping into subchromosomal regions was performed by PCR on a series of DNAs derived from somatic cell hybrids that subdivide the chromosome into cytogenetic bins (FIG. 1).

We found that the use of primers derived from 48 cDNA clones successfully amplified unique bands of the expected size, specifically on chromosome 18 somatic cell hybrid DNA (Table 2). Further analysis using the same primer pairs against sequence databases was conducted. By comparison using a BLASTN similarity search with GenBank (Altschul, J Mol Biol, 215:403–410, 1990) and a Level I sequence EST homology search of The Institute for Genome Research (TIGR) database (Adams et al., Nature, 377 (Suppl.):3–174, 1995), we found that of the 48 chromosome 18-specific cDNAs, 11 were highly homologous (defined as>89% homology over>100 bp) to segments of five previously known genes (see Table 4, below).

Myelin basic protein (MBP, Kamholz et al., Proc Natl Acad Sci USA, 83:4962–6, 1986), the 63 kDa protein kinase related to ERK3 (HS63KDAP, Li et a., Oncogene, 9:647–649, 1994) and the protein tyrosine phosphatase receptor, mu polypeptide (PTPRM, Suijkerbuijk et al., Cytogenet Cell Gene, 64(3–4):245–6, 1993) were each represented in four, three and two clones, respectively. The Gs alpha, olfactory type (GNAL, Zigman et al., Endocrinology, 133:2508–14. 1993) and 5' H. sapiens hypothetical protein (HUMKIAAN, Nomura et al., "Prediction of the coding sequences of unidentified human genes" (Genbank Accession #D42055, 1993)) were represented in one clone each. In addition, the map assignments obtained for transcripts of these five genes were consistent with previously reported data (Table 4 and FIG. 2).

A FASTA (Pearson and Lipman, Proc Natl Acad Sci USA, 85:6565–6572, 1988) sequence comparison among the remaining 37 cDNA clones to search for redundancy (defined as ∃ 89% identical sequence over>100 bp) indicated that 20 cDNAs were unique and 17 redundant cDNAs represented five groups of unique sequences. Therefore, including

TABLE 4

Chromosome 18 specific brain derived cDNAs homologous to known genes.

| Clone Number | BLASTN/TIGR sequence homology | Cytogenetic Location | Percentage Identical 5' | Percentage Identical 3' | Reference |
|---|---|---|---|---|---|
| 1 | 63 kDa protein kinase related to ERK3 (HS63KDAP) | 18q21.2–18q21.3 | 98.4 | 97.5 | Li et al. 1994 |
| 3 | 63 kDa protein kinase related to ERK3 (HS63KDAP) | 18q21.2–18q21.3 | 95.3 | 96.2 | Li et al. 1994 |
| 7 | Myelin basic protein (MBP) | 18q23 | 95.8 | 93.5 | Kamholz et al. 1986 |
| 10 | 63 kDa protein kinase related to ERK3 (HS63KDAP) | 18q21.2–18q21.3 | 99.6 | 98.4 | Li et al. 1994 |
| 11 | Protein tyrosine phosphatase. receptor-type, mu polypeptide (PTPRM) | 18p11.2 | none | 89.2 | Suijkerbuijk et al. 1993 |
| 12 | Myelin basic protein (MBP) | 18q23 | 95.7 | 92.1 | Kamholz et al. 1986 |
| 18 | Myelin basic protein (MBP) | 18q23 | 94.5 | 98.1 | Kamhoiz et al. 1986 |
| 31 | Guanine nucleotide-binding protein, alpha-subunit, olfactory type (GNAL) | 18p11.22–p11.21 | 98.9 | 98.6 | Zigman et al. 1993 |
| 40 | 5' H sapiene hypothetical protein (HUMKIAAN) | 18q21.3–18qter | 98.4 | none | Nomura et al. 1995 |
| 45 | Protein tyrosine phosphatase, receptor-type, mu polypeptide (PTPRM) | 18p11.2 | 94.0 | 90.0 | Suijkerbuijk et al. 1993 |
| 46 | Myelin basic protein (MBP) | 18q23 | 95.3 | none | Kamholz et al. 1986 |

(Table 2) revealed that each of these 48 clones mapped to a specific chromosome 18 cytogenetic bin (Table 3 and FIG. 1), therefore, confirming our initial data on the chromosomal assignment. The remaining clones mapped either ambiguously or elsewhere in the genome.

Interestingly, most of 48 brain transcripts appeared to cluster within discrete cytogenetic regions on chromosome 18: bins A and B, in the short arm and bins M and S, in the long arm (Table 3 and FIG. 1).

Example 10

Sequence Homology Comparisons to Identify Unique Chromosome 18-Specific Transcripts To determine the identity and uniqueness of each of the 48 chromosome 18-specific transcripts, a homology search the transcripts for the known genes, we have identified a total of 30 unique transcripts, of which 25 did not exhibit homology to previously known genes. The insert sizes of the cDNA clones that were determined to be chromosome 18-specific ranged from 1 to 2 kb (Table 3). To explore the presence of an open reading frame (ORF) in each clone and to further examine any homology to known genes, we determined the remaining sequence of the unique clones (sequences were deposited in the Genbank with the following accession numbers: U55777 and U55962 to U55991). We found potential polyadenylation signals in some of the clones. So far, no ORFs have been detected suggesting that a major portion of the cDNA clones corresponded to 3' UTRs. More importantly, comparison of the longer sequences of the cDNAs with sequences in the databases failed to reveal significant homology with any known genes, supporting the idea that these transcripts were derived from novel genes.

Example 11

Radiation Hybrid Mapping

To achieve a higher resolution map for each of the transcripts by PCR, we used the Stanford G3 radiation hybrid series and primers specific for each cDNA. Of the 25 unique transcripts, 19 were successfully linked to chromosome 18 STSs (see Table 5, below and FIGS. 2 and 3).

Figure 2:
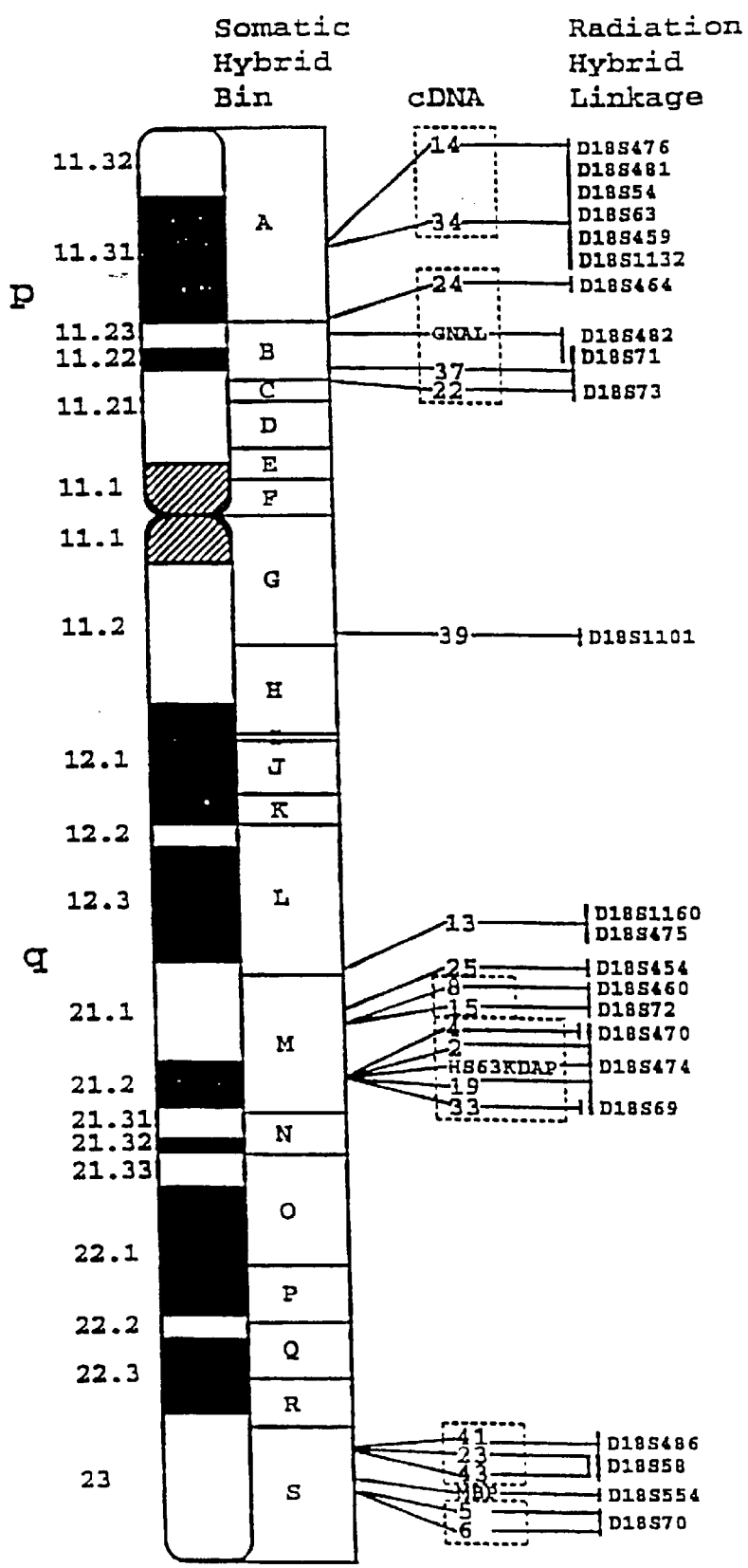
FIG. 2 shows the results of a high resolution mapping of transcripts versus chromosome 18 reference STS by the use of radiation hybrids. A schematic representation of the position of the unique transcripts with respect to linked STSs. Transcripts and genes that are members of a radiation hybrid linkage group are enclosed in dashed boxes. The approximate locations within the cytogenetic bins are also indicated.

The positions of the cDNAs in the radiation hybrid framework map were consistent with their subchromosomal assignments (FIGS. 1, 2, and 3). With this method, fine mapping was established for the unique transcripts as evidenced by the physical distance between them and the chromosome 18 STSs which ranged from approximately 4 to 46 cR, estimated to be between approximately 100 kb and 1100 kb (FIGS. 1, 2, and 3).

Radiation hybrid mapping was also used to position the known genes identified in this study against the 25 non-redundant transcripts. We found that HS63KDAP formed a high resolution linkage group with clones 2, 4, 19 and 33 (Table 5 and FIG. 2). The fine map locations of the anonymous markers D18S37, D18S53 and D18S40 were similarly examined, since they showed excess allele sharing in manic-depressive affected sib-pairs in two studies (Berrettini et al., *Proc Natl Acad Sci USA*, 91:5918–5921, 1994; Stine et al., *Am J Hum Gene*, 57:1384–1394, 1995). These three markers, GNAL and cDNA clones 22, 24 and 37 assembled into a separate radiation hybrid linkage group (Table 5 and FIG. 2). Further investigation into the linkage overlaps between the STSs, genes and

TABLE 5

Radiation hybrid mapping of unique cDNA clones*

| Test Market | Reference Marker | LOD | Distance to Reference Marker (cR8000) |
|---|---|---|---|
| 14 | D18S476 | 10.2 | 25.78 |
|  | D18S481 | 11.3 | 15.04 |
|  | D18S54 | 8.9 | 32.31 |
|  | D18S63 | 10.9 | 22.50 |
|  | D18S459 | 10.2 | 25.78 |
|  | D18S1132 | 7.0 | 42.16 |
| 34 | D18S476 | 8.3 | 32.61 |
|  | D18S481 | 12.4 | 16.08 |
|  | D18S54 | 12.7 | 15.96 |
|  | D18S63 | 14.6 | 9.61 |
|  | D18S459 | 14.6 | 9.61 |
|  | 14 | 7.6 | 38.31 |
|  | D18S1132 | 6.8 | 41.79 |
| 24 | D18S464 | 11.0 | 16.07 |
|  | D18S53 | 6.1 | 45.87 |
| OMAL | D18S482 | 7.8 | 36.15 |
|  | D18S71 | 9.0 | 31.62 |
| D18653 | D18S464 | 7.5 | 35.77 |
|  | D18S482 | 7.0 | 39.77 |
|  | D18S71 | 6.9 | 42.39 |
| 37 | D18S73 | 7.1 | 40.23 |
|  | D18S71 | 8.0 | 35.03 |
| 22 | D18S73 | 7.7 | 37.31 |
|  | D18S40 | 13.3 | 16.92 |
| D18640 | D18S73 | 11.2 | 21.40 |
|  | D18S71 | 7.3 | 40.07 |
| D18637 | D18S73 | 13.5 | 16.28 |
|  | D18S71 | 7.6 | 39.76 |

TABLE 5-continued

Radiation hybrid mapping of unique cDNA clones*

| Test Market | Reference Marker | LOD | Distance to Reference Marker (cR8000) |
|---|---|---|---|
| 39 | D18S1101 | 7.8 | 37.31 |
| 13 | D18S1160 | 7.8 | 28.72 |
|  | D18S475 | 7.7 | 19.22 |
| 25 | D18S454 | 10.3 | 10.73 |
| 8 | D18S460 | 7.8 | 28.65 |
|  | D18S72 | 7.8 | 28.72 |
| 15 | D18S460 | 7.2 | 30.83 |
|  | D18S72 | 8.5 | 24.10 |
|  | 6 | 12.5 | 8.60 |
| 4 | D18S470 | 6.1 | 42.49 |
|  | 19 | 6.6 | 35.80 |
| 2 | 19 | 14.3 | 4.08 |
|  | D18S470 | 12.6 | 11.47 |
|  | 4 | 6.0 | 40.67 |
|  | D18474 | 8.3 | 24.21 |
|  | D18S69 | 8.2 | 27.02 |
| HS63KDAP | 2 | 10.5 | 17.02 |
|  | D18S474 | 9.8 | 18.18 |
|  | 19 | 9.1 | 22.46 |
|  | D18S470 | 7.7 | 33.44 |
|  | D18S69 | 6.5 | 38.01 |
| 19 | D18S470 | 10.3 | 19.96 |
|  | D18S474 | 8.4 | 24.51 |
|  | D18S69 | 7.1 | 33.41 |
| 33 | D18S69 | 7.1 | 33.41 |
| 41 | D18S486 | 6.5 | 33.52 |
|  | D18S58 | 7.2 | 30.83 |
|  | 23 | 15.1 | 3.85 |
| 23 | D18S58 | 6.6 | 35.71 |
| 43 | 23 | 14.4 | 7.28 |
|  | 41 | 12.7 | 11.44 |
|  | 018S58 | 6.5 | 35.88 |
| MRP | D18S554 | 7.8 | 25.97 |
| 5 | D18S70 | 7.0 | 21.37 |
| 6 | D18S70 | 6.3 | 28.01 |
| 9 | NL |  |  |
| 16 | NL |  |  |
| 29 | NL |  |  |
| 30 | NL |  |  |
| 36 | NL |  |  |
| 47 | NL |  |  |
| HUMKIAAN | NL |  |  |
| PTPRN | NL |  |  |

*A description of the Stanford G3 radiation hybrid panel is in the text. Markers in bold represent cDNAs identified in this study or anonymous STSs.
NL markers which could not be mapped to the radiation hybrid framework markers.

unique transcripts showed that at least six radiation hybrid linkage groups were evident (FIG. 2). Based on these physical relationships, a map order within each linkage group could be deduced.

In sum, using direct cDNA selection and physical mapping by PCR, we have identified and positionally catalogued 48 chromosome 18-specific cDNAs that are expressed in infant brain. Sequence database comparison revealed a level of redundancy in the 48 clones, yielding a total of 30 unique transcripts. Five genes previously assigned to chromosome 18 were represented in these transcripts. Additional sequence analysis of the remaining 25 non-redundant cDNA clones and database comparisons failed to elicit any significant homology to known genes indicating that these brain-expressed transcripts represent novel genes.

So far, we have no evidence for possible redundancies among the unique transcripts due to alternative splicing or the presence of pseudogenes, but these probably are very minor components of the cDNA library. Polymeropoulos et al., Chromosomal distribution of 320 genes from a brain cDNA library, *Nature Gene* (1993) suggested the possibility that chromosome 18 may be gene-poor. A recent effort to sequence and map cDNAs yielded only four on chromosome 18 out of the several hundred cDNAs localized to other chromosomes (Berry et al., Gene-based sequence-tagged-sites (STSs) as the basis for a human gene map, *Nature Gene* 10:415–423 (1995). The 25 unique cDNA clones isolated in this study, therefore, represent a significant increase in the number of new genes on chromosome 18.

Example 12

Transmission Equilibrium Test (TDT) on Clone 22 in Two Pedigree Series

In the pedigree series described in Berrettini et al., *Psychiatric. Gene*. 2:125–160 (1991), incorporated herein by reference) linkage disequilibrium with manic-depressive illness is observed for genes within the region of the radiation hybrid map (FIG. 3) between markers D18S843 and D18S869. The best results are given by clone 22, where allele 2 shows preferential transmission in this and a second independent pedigree series (see Table 6, below).

The second pedigree series is the manic-depressive pedigree series recently made publicly available by the Nationals Institutes of Mental Health as part of its Genetics

TABLE 6

TRANSMISSION/DISEQUILIBRIUM TEST (TDT) ON CLONE 22 IN TWO PEDIGREE SERIES

| Allele | Freq | Transmitted | Not Transmitted | P-value |
|---|---|---|---|---|
| Bethesda Bipolar Pedigree Series | | | | |
| 1 | 0.344 | 37 | 59.$^{s,}$ | 0.025 |
| 2 | 0.656 | 59 | $37_{s\_}$* | |
| NIMH Genetics Initiative Collaborative Series | | | | |
| 1 | 0.376 | 83 | 116 | 0.019 |
| 2 | 0.622 | 118 | 83 | 0.014 |
| 3 | 0.002 | 0 | 2 | N/A |

Initiative. The statistical test is the transmission I disequilibrium test (TDT) of Spielman R. et al., *Am. J Hum. Gene.* 52:506–516 (1993). In the analysis of these two pedigrees, manic-depressive individuals are genotyped to determine the whether a particular allele of the clone 22 polymorphic marker has been transmitted or not transmitted to them. Given the relative frequencies of the alleles, the probability (P-value)of the co-occurrence of manic-depressive illness and a particular clone 22 allele is determined. The results indicate preferential transmission of allele 2 to manic-depressive affecteds.

Example 13

Discovery, Characterization and Isolation of IMP.18p

This example sets forth the discovery, characterization and isolation of the novel inositol monophosphatase gene and protein of the invention, designated IMP.18p.

Linkage of manic depression/bipolar disorder to the broad pericentromeric region of chromosome 18 (Berrettini (1994) siqjra; Stine (1995) *Am. J. Hum Genet*. 57:1384–1394) motivated a search for novel genes and gene products which are associated with this disease. The initial bipolar disorder-chromosome 18 linkage region spanned approximately 40 centimorgan (cM). Genetic analysis in the 22-pedigree series, reported by Berrettini (1994) supra, indicates that the highest allele sharing is in markers mapping to 18p 11.2. An association (nominal P<0.05) was found at either D18S53 or D18S37 (designated S53 and S73 (S37 and S73 amplify the same locus), respectively, in Table 3) on 18p 11.2.

As described in Example 11, above, markers within 18p11.2 showing increased sharing were mapped using a radiation hybrid (RH) panel to an approximately 6 megabase (Mb) region. These lines of evidence indicated this region on 18p11.2 is a site for the identification of transcripts and genes associated with bipolar disorder. Electronic databanks were searched for ESTs, sequence tag sites (STSs) and genes which had been mapped as being encoded in the general area of 18p11.2.

This search identified a human STS of 145 base pairs, identified as A006N05 (GenBank), localized between D18S464 and D18S71, markers that map to 18p11.2. This STS had been isolated and mapped by The Institute of Genome Research (TIGR) and was included in an approximately 1 kb TIGR EST, designated contig THC98649, described by Boguski (1997) *Nature Genet*. 10:369–371, http://www.ncbi.nlm.nih.gov/UniGene/index.html.

The STS sequence of A006N05 was searched using the transcript database of Schuler (1996) *Science* 274:540–546, http://www.ncbi.nlm.nih.gov/SCIENCE96/, and, updates in Unigene at http://www.tigr.org/tigr_home/index.htrnl, of the National Center for Biotechnology Information. Using the method (described in Altschul (1990) *J. Mol Biol*. 215:403–410), it was discovered that the human THC98649 EST contig contained an upstream sequence exhibiting about 60% nucleotide homology (sequence identity) with the inositol monophosphatase (IMP) of *Xenopus laevis*. Manipulation of these databanks further discovered that the THC98649 EST contig is included in the approximately 1.2 kb insert of the IMAGE human cDNA clone ID #39740 (I.M.A.G.E. Consortium, Human Genome Center, DOE, Lawrence Livermore National Laboratory, Livermore, Calif.).

To identify which human cells express this or a message closely related to clone ID #39740, Northern blots of various human tissues was performed. Northern blots of multiple human tissues were purchased from Clontech (Palo Alto, Calif.). The Northern's probe was prepared by amplifying the insert of the cDNA clone #39740 with M13 forward and reverse primers, then $^{32}$P labeling the amplified product using a standard random primer method. Blots were hybridized using Rapid-hyb buffer (Amersham, Cleveland Ohio) at 68° C., with 2×106 cpm/ml probe. The final wash was done at 68° C. with 0.1×SSC containing 0.1% SDS. The blots were exposed onto X-ray film overnight at −70° C. with intensifying screens.

Figure 4:
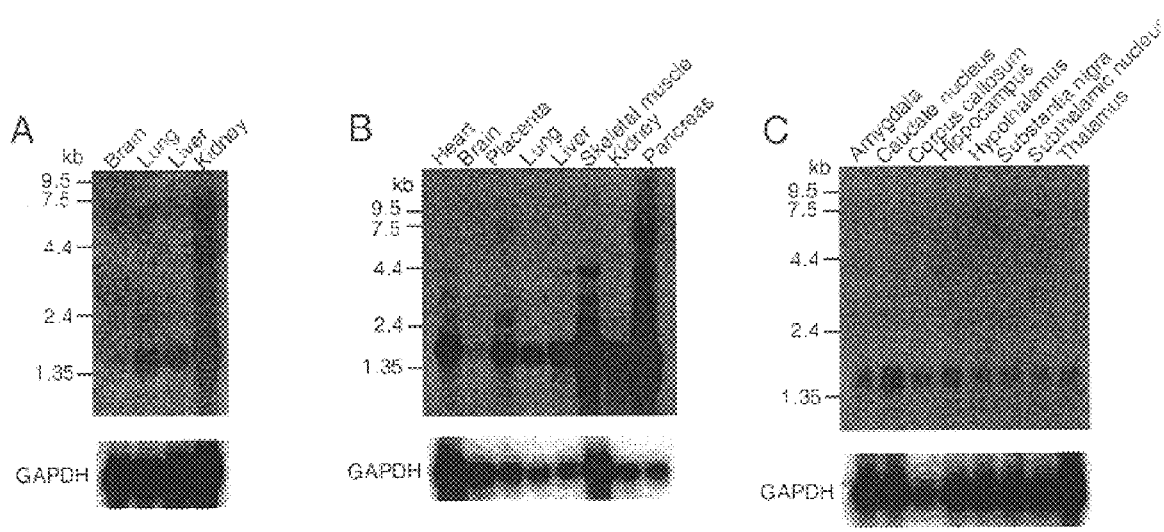
FIG. 4 shows that the amplified, radiolabeled probe from cDNA clone ID #39740 was found to detect a major band of approximately 1.5 kb in multiple tissues through Northern hybridization.

The amplified probe from cDNA clone ID #39740 was found to detect a major band of approximately 1.5 kb in multiple tissues through Northern hybridization, as shown in FIG. 4. FIGS. 4A, 4B, and 4C show that this cDNA probe hybridizes to a 1.5 kb message to varying degrees in: fetal brain, lung, liver and kidney; adult heart, brain, lung, liver, skeletal muscle, kidney, and pancreas; and, adult brain amygdala, caudate nucleus, corpus callosurn, hippocampus, hypothalamus, substantia nigra, subthalamic nucleus, and thalamus. Control hybridizations were done with GAPDH (constitutively expressed in all of these tissues). As can be seen by the relative intensities of the hybridization bands as compared to control, IMP.18p was abundantly expressed in both adult and fetal skeletal muscle, pancreas, heart, placenta, liver and lung, but to a more limited extent in whole brain. Contrary to the minimal level of IMP.18p transcript in whole brain, a substantial expression was found in brain subcortical regions with caudate showing a higher expression level than the other anatomical substrates (FIG. 4C).

cDNA clone #39740 was sequenced by conventional techniques. Analysis of this sequence showed that clone #39740 was missing its 5'-end coding sequence. Additional upstream coding sequence was acquired using rapid amplification of cDNA 5' ends (5' RACE) PCR, as described above. Marathon-Ready cDNA derived from human skeletal muscle (Clontech, Palo Alto, Calif.) and the clone-specific primer designated p1: 5'-ACGTCGGGCTGTGGGTGAGCACACACTTG (SEQ ID NO:24) (corresponding to nucleotides number 405 to 433 of clone #39740). PCR was performed using an initial one minute denaturation at 94° C., followed by 5 amplification cycles at 94° C. for 15 sec, 72° C. for 2 min; and, 30 cycles of 94° C. for 15 sec, 65° C. for 30 sec, 72° C. for 2 min, and final extension period at 72° C. for 5 min, using Taq DNA polymerase (Perkin Elmer) and MasterAmp 2×PCR PreMix I (Epicentre Technologies, Madison, Wis.). Sequencing was conducted using a dye terminator cycle sequencing kit with Taq FS (Perkin Elmer Applied Biosystems, Foster City, Calif.) and the ABI 373 DNA sequencer (Applied Biosystems, supra). Each nucleotide sequence was verified using at least two independent sequence reactions including both strands. Sequence similarity search, alignment and motif detection were done using the Genetics Computer Group, Inc. (GCG, Madison, Wis.) computer package.

The RACE method extended the upstream region of clone #39740 by 278 base pairs and included the potential initiation methionine. FIG. 5B shows the complete 1447 base pair full-length cDNA nucleotide sequence (SEQ ID NO:16) and the corresponding predicted amino acid sequence (SEQ ID NO:17). An in-frame stop codon in the 5' untranslated region (UTR) and a poly(A) signal in the 3' UTR are underlined. FIG. 5A shows a schematic representation of this newly discovered message aligned with clone #39740, the open triangle depicts the coding region. Also shown as arrows are location of the sequence used to design primers p2 and p3 used in radiation hybridization mapping, discussed below.

The location of this IMP gene on chromosome 8 was established using ESTs from the Unigene databank (Boguski (1995) supra).

The 1447 bp full-length cDNA has a predicted open reading frame encoding a protein with 288 amino acids and a G-C rich 5'-untranslated region (UTR) (FIG. 5B). A protein homology search (as described in Altschul (1990) supra) showed a 53.5% identity to a human brain myo-inositol monophosphatase (IMP) gene, as described by McAllister (1 992) Biochem. J. 284:749–754. The McAllister, (1992) supra, IMP cDNA has a considerable sequence difference and is encoded in a distinct chromosomal localization as compared to the IMP of the invention. Thus, this newly discovered IMP represents a novel gene and protein, and is designated IMP.18p. As shown in FIG. 6, IMPs protein sequences from Xenopus laevis (SEQ ID NO:25), rat (SEQ ID NO:26) and bovine (SEQ ID NO:27) have a 54.8%, 53.5% and 53.8% sequence identity, respectively, with the IMP.18p protein. Xen (SEQ ID NO:25), Bov (SEQ ID NO:27) and Hum (SEQ ID NO:28) represent Xenopus laevis, bovine and human sequences. Dots indicate identical amino acids. In further contrast to other IMPs, as shown in FIG. 6, the IMP.18p of the invention has an additional 11 amino terminal residues not seen in previously characterized inositol monophosphatases.

Two protein motifs characteristic of the myo-inositol monophosphatase protein family, which includes animal inositol phosphatases, fungal and bacterial regulatory proteins of unknown enzymatic activity, as found by Neuwald (1991) FEBS LETT 294:16–18, were also found in IMP.18p, as indicated in FIG. 6. Motif A has the consensus sequence (W)x(I)DP(I)D(G)Tx{2}(F)x(H) and motif B (SEQ ID NO:11) has the consensus sequence: Wdx{2}(A){2}x(V)(I){2}x{3}(G,A){2}(SEQ ID NO:196).

In IMP.18p, motif A and motif B correspond to amino acids number 98 to 111 and 230 to 244, respectively, see FIG. 6; as numbered in FIG. 5B. In IMP.18p, the amino acid residues Asp101, Ile103, Asp104, Thr106 and Asp231 (as identified by the amino acid numbering in FIG. 6) fall inside the motif regions characterized by Neuwald. These motifs have been suggested to exert an important role in metal binding (see Pollack (1994) "Mechanism of inositol monophosphatase, the putative target of lithium therapy" Proc. Natl. Acad. Sci. USA 91:5766–5770) and in the catalytic activity of the human IMP on chromosome 8 (see Pollack (1993) "Probing the role of metal ions in the mechanism of inositol monophosphatase by site-directed mutagenesis," Eur. J. Biochem. 217:281–287). Sharing these structural motifs, IMP.18p is also expected to have inositol monophosphatase and lithium binding capabilities.

Northern hybridization was conducted under high stringency conditions to minimize cross hybridization with homologous mRNAs (i.e., wash conditions that minimized cross hybridization were used: 0.1×SSC, 0.1% SDS, 65° C.). The human chromosome 8 IMP of McAllister, (1992) supra, expresses a transcript that is 2.2 kb (Pollack (1993) supra), which distinguishes it from the novel IMP of the invention, IMP.18p, whose primary mRNA transcript, as determined by Northern blot, is 1.5 kb in length (see FIG. 4).

Figure 7:
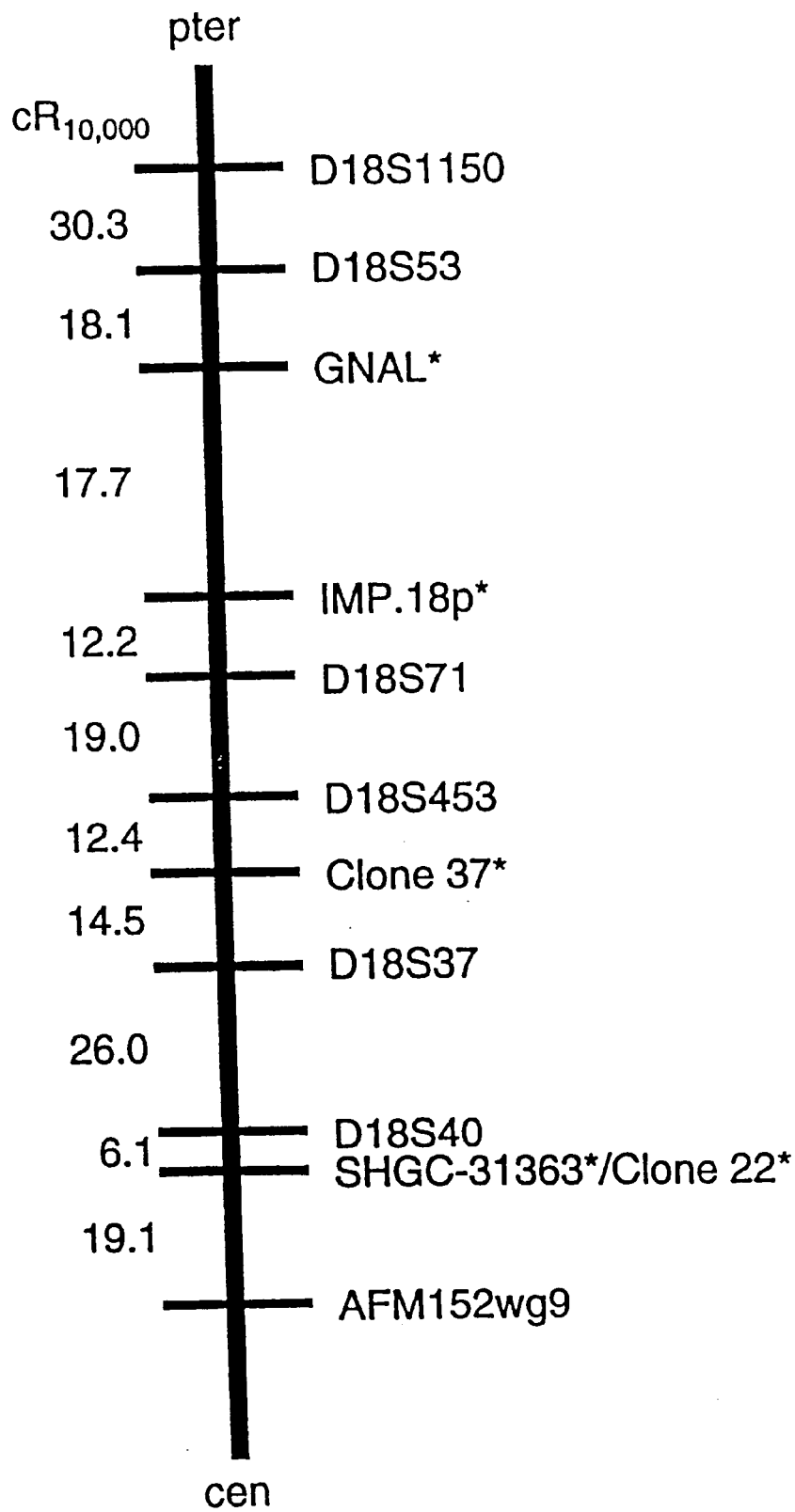
FIG. 7 shows the mapping position of the gene encoding the IMP.18p myo-inositol monophosphatase is within the bipolar susceptibility region at 18p11.2 of chromosome 18.

To achieve a fine physical localization on chromosome 18, IMP.18p was further mapped utilizing radiation hybrid (RH) mapping (using the Stanford Human Genome Center's (SHGC) G3 panel, as described by Cox (1990) "Radiation hybrid mapping: a somatic cell genetic method for constructing high resolution maps of mamnmalian chromosomes," Science 250:245–250), as described in Example 11, above. Multipoint RH mapping determined locus order and interlocus distance between IMP.18p and other markers on 18p11.2, using the MultiMap/RADMAP computer programs (as described in Matise (1995) "Automated construction of radiation hybrid maps using MultiMap," Am. J. Hum. Genet. (Suppl.) 57:A15), under an equal retention model. Strategies for multipoint RH mapping and selection of markers has been described, for example, in Lunetta (1 996) Am. J. Hum. Genet. 59:717–725; Francke (1994) "A radiation hybrid map of human chromosome 18," Cytogenet. Cell. Genet. 66:196–213; also, http://www.ebi.ac.uk/RHdb/vers_soft.html. Initially, a linkage group with the criteria of a lod 5 and a breakage probability of lod 0.3 was identified. Next, markers from the linkage group were mapped with a placement threshold of lod 3. This analysis ordered 11 loci in a region of 175.4 cR (approximately 4.7 megabase, assuming the mean ratio of 26.8 kb/cR in chromosome 18 (Cox (1990) supra) and placed IMP.18p between guanine nucleotide-binding protein-olfactory, type-a subunit, or G(olf), ("GNAL," Berrettini (1990) supra) and D18S71. This mapping positions the gene encoding the IMP.18p myo-inositol monophosphatase of the invention within the bipolar susceptibility region at 18p11.2, as shown in FIG. 7.

Example 14

Characterization of the promoter region of IMP.18p

This example sets forth the discovery and characterization of the promoter region of the novel inositol monophosphatase gene, IMP.18p, of the invention.

To facilitate screening of the entire IMP.18p genomic sequence and to provide for a monophosphatase-specific transcriptional regulatory element for use in the construction of, for example, tissue-specific expression vectors, transgenic animal expression cassettes, and targets for expression-regulating nucleotide sequences, the promoter of IMP.18p was identified and characterized.

Cosmid clones from a chromosome 18-specific cosmid library LL18NCO2, from Lawrence Berkeley Laboratory, were isolated by spotting the library onto nylon membranes to generate high density filters. These filters were hybridized with a IMP.18p cDNA probe (SEQ ID NO:16). Three clones, designated 119C4, 97A4 and 69E10, which hybridized to the cDNA probe were isolated. Sequencing was performed using the dye terminator cycle sequence kit with TaqFS from Perkin Elmer-Applied Biosystems, Inc. (ABI, Foster City, Calif.) and an ABI 373 DNA sequencer.

The transcriptional initiation site was determined by primer extension using a "Primer Extension System" from Promega (Madison, Wis.). An IMP.18p-specific antisense oligonucleotide primer (underlined coding sequence in FIG. 8, designated "p") was 5' end-labeled with gamma 32-P ATP and T4 polynucleotide kinase. 100 fmol of the labeled primer was annealed to 1.6 ug of poly(A)+ RNA derived from skeletal muscle (Clontech) at 58° C. for 20 minutes, and then kept at room temperature for 10 minutes. Annealed primers were extended with AMV reverse transcriptase at 42° C. for 30 minutes. The extended products were analyzed on a 6% sequencing gel, electrophoresed beside a sequence ladder that was generated by sequencing the appropriate region of cosmid 97A4 with the same primer used in primer extension analysis 5'-GGG CGA CCG ACG GGA AG-3' (SEQ ID NO:197).

The major extension product was 183 base pairs corresponding to 160 base pairs upstream of the initiation ATG, as shown in FIG. 8 (SEQ ID NO:25) (the nucleotide sequence of the 5' flanking region is lowercase, and the upstream portion of exon 1 is uppercase). The major cap site is indicated as nucleotide+1 and is denoted by an arrow pointed in the direction of transcription. A minor transcriptional start site, as shown by primer extension analysis, is a "T" residue at position (minus) −6. The translational initiation codon is boxed.

The sequence around the transcription initiation site did not indicate the presence of TATA and CAAT boxes. However, there were multiple, potential recognition sites for Sp1, in addition to consensus sites for other transcription factors, as indicated in FIG. 8. TATA-less promoters have been described in "housekeeping genes," oncogenes, growth factors and their receptors, and transcription factors (as reviewed in Azizkhan (1993) *Crit. Rev. Eukaryotic Gene Erpression* 3:229–254). The promoter region of IMP.18p gene has several features shared by other TATA-less genes, including a GC-rich sequence with multiple CpG islands; several Sp1 consensus motifs; and, heterogeneity in transcription initiation (FIG. 8).

All publications and patents mentioned in this specification are herein expressly incorporated by reference into the specification for all purposes to the same extent as if each individual publication or patent was specifically and individually indicated to be incorporated herein by reference.

What is claimed is:

1. An isolated nucleic acid encoding an IMP.18p myo-inositol monophosphatase, said protein defined as follows:
   (i) having a calculated molecular weight of between about 22 to 34 kDa;
   (ii) the protein's activity includes hydrolysis of myo-inositol 1-phosphate to generate inositol and inorganic phosphate;
   (iii) specifically binding to an antibody raised against an IMP.18p myo-inositol monophosphatase protein;
   wherein the nucleic acids amplifiable by a primer set of SEQ ID NO:18 and SEQ ID NO:19, and encodes a protein at least 80% identical to the sequence set forth in SEQ ID NO:17.

2. The isolated nucleic acid of claim 1, wherein the calculated molecular weight of the encoded protein is about 28 to 29 kDa.

3. The isolated nucleic acid of claim 1, wherein the encoded protein has the sequence set forth in SEQ ID NO:17.

4. The isolated nucleic acid of claim 1, wherein the nucleic acid has the sequence as set forth in SEQ ID NO; 16.

5. An expression vector comprising a nucleic acid encoding an IMP.18p myo-inositol monophosphatase protein, said protein defined as follows:
   (i) having a calculated molecular weight of between about 22 to 34 kDa,
   (ii) the protein's activity includes hydrolysis of myo-inositol 1-phosphate to generate inositol and inorganic phosphate,
   (iii) specifically binding to an antibody raised against an IMP.18p myo-inositol monophosphatase protein;
   wherein the nucleic acid is amplifiable by a primer set of SEQ ID NO:18 and SEQ ID NO:19, and encodes a protein at least 80% identical to the sequence sot forth in SEQ ID NO:17.

6. A cell comprising an exogenous nucleic acid sequence comprising a nucleic acid which encodes:
   an IMP.18p myo-inositol monophosphatase protein, said protein defined as follows:
   (i) having a calculated molecular weight of between about 22 to 34 kDa,
   (ii) the protein's activity includes hydrolysis of myo-inositol 1-phosphate to generate inositol and inorganic phosphate,
   (iii) specifically binding to an antibody raised against an IMP.18p myo-inositol monophosphatase protein;
   wherein the nucleic acid is amplifiable by a primer set of SEQ ID NO:18 and SEQ ID NO:19, and encodes a protein at least 80% identical to the sequence set forth in SEQ ID NO:17.

7. A method for detecting the presence of a polynucleotide sequence encoding at least a portion of an IMP.18p myo-inositol monophospbatase in a biological sample, comprising the steps of:
   a) providing:
      i) a biological sample suspected of containing a nucleic acid encoding an IMP.18p myo-inositol monophosphatase;
      ii) a probe comprising a sequence as set forth in SEQ ID NO:18, or its complement, that hybridizes under stringent conditions to a nucleotide sequence encoding an IMP.18p myo-inositol monophosphatase, wherein the nucleic acid encodes a protein at least 80% identical to the sequence set forth in SEQ ID NO:17, and is amplifiable by a primer set of SEQ ID NO:18 and SEQ ID NO:19;
   b) combining said nucleic acid-containing biological sample with said probe under conditions such that a specific hybridization complex is formed between said nucleic acid and said probe; and
   c) detecting said hybridization complex as indicative of the presence of said polynucleotide sequence.

8. The method of claim 7, wherein, said nucleic acid in said biological sample is ribonucleic acid.

9. The method of claim 8, wherein said detected hybridization complex correlates with expression of an IMP.18p myo-inositol monophosphatase in said biological sample.

\* \* \* \* \*

SEQUENCE LISTING (1) GENERAL INFORMATION:

(iii) NUMBER OF SEQUENCES: 197

(2) INFORMATION FOR SEQ ID NO: 1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1...22
      (D) OTHER INFORMATION: Clone 22 upstream primer (xi) SEQUENCE DESCRIPTION: SEQ ID NO: 1:

CAAGTTTATG TTACTGCCAG GG      22

(2) INFORMATION FOR SEQ ID NO: 2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (ix) FEATURE:

(A) NAME/KEY: -
            (B) LOCATION: 1...21
            (D) OTHER INFORMATION: Clone 22 downstream primer (xi) SEQUENCE DESCRIPTION: SEQ ID NO: 2:

GCAGCTTCCT AATGCATCCA G                                                21

(2) INFORMATION FOR SEQ ID NO: 3:

(i) SEQUENCE CHARACTERISTICS:
        (A) LENGTH: 306 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: mat_peptide
        (B) LOCATION: 1...306
        (D) OTHER INFORMATION: Clone 22 isoform 1,
            unspliced protein (xi) SEQUENCE DESCRIPTION: SEQ ID NO: 3:

Met Pro Glu Ala Gly Phe Gln Ala Thr Asn Ala Phe Thr Glu Cys Lys
 1               5                  10                  15

Phe Thr Cys Thr Ser Gly Lys Cys Leu Tyr Leu Gly Ser Leu Val Cys
                20                  25                  30

Asn Gln Gln Asn Asp Cys Gly Asp Asn Ser Asp Glu Glu Asn Cys Leu
            35                  40                  45

Leu Val Thr Glu His Pro Pro Gly Ile Phe Asn Ser Glu Leu Glu
 50                  55                  60

Phe Ala Gln Ile Ile Ile Ile Val Val Val Thr Val Met Val Val
 65                  70                  75                  80

Val Ile Val Cys Leu Leu Asn His Tyr Lys Val Ser Thr Arg Ser Phe
                85                  90                  95

Ile Asn Arg Pro Asn Gln Ser Arg Arg Arg Glu Asp Gly Leu Pro Gln
                100                 105                 110

Glu Gly Cys Leu Trp Pro Ser Asp Ser Ala Ala Pro Arg Leu Gly Ala
            115                 120                 125

Ser Glu Ile Met His Ala Pro Arg Ser Arg Asp Arg Phe Thr Ala Pro
    130                 135                 140

Ser Phe Ile Gln Arg Asp Arg Phe Ser Arg Phe Gln Pro Thr Tyr Pro
145                 150                 155                 160

Tyr Val Gln His Glu Ile Asp Leu Pro Pro Thr Ile Ser Leu Ser Asp
                165                 170                 175

Gly Glu Glu Pro Pro Tyr Gln Gly Pro Cys Thr Leu Gln Leu Arg
            180                 185                 190

Asp Pro Glu Gln Gln Met Glu Leu Asn Arg Glu Ser Val Arg Ala Pro
    195                 200                 205

Pro Asn Arg Thr Ile Phe Asp Ser Asp Leu Ile Asp Ile Ala Met Tyr
    210                 215                 220

Ser Gly Gly Pro Cys Pro Pro Ser Ser Asn Ser Gly Ile Ser Ala Ser
225                 230                 235                 240

Thr Cys Ser Ser Asn Gly Arg Met Glu Gly Pro Pro Thr Tyr Ser
                245                 250                 255

Glu Val Met Gly His His Pro Gly Ala Ser Phe Leu His His Gln Arg
            260                 265                 270

Ser Asn Ala His Arg Gly Ser Arg Leu Gln Phe Gln Gln Asn Asn Ala

```
                        275                 280                 285
Glu Ser Thr Ile Val Pro Ile Lys Gly Lys Asp Arg Lys Pro Gly Asn
    290                 295                 300

Leu Val
305
```

(2) INFORMATION FOR SEQ ID NO: 4:

(i) SEQUENCE CHARACTERISTICS:
        (A) LENGTH: 288 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: mat_peptide
        (B) LOCATION: 1...288
        (D) OTHER INFORMATION: Clone 22 isoform 2
            alternatively spliced
            protein (xi) SEQUENCE DESCRIPTION: SEQ ID NO: 4:

```
Met Pro Glu Ala Gly Phe Gln Ala Thr Asn Ala Phe Thr Glu Cys Lys
1               5                   10                  15

Phe Thr Cys Thr Ser Gly Lys Cys Leu Tyr Leu Gly Ser Leu Val Cys
                20                  25                  30

Asn Gln Gln Asn Asp Cys Gly Asp Asn Ser Asp Glu Glu Asn Cys Leu
            35                  40                  45

Leu Val Thr Glu His Pro Pro Gly Ile Phe Asn Ser Glu Leu Glu
    50                  55                  60

Phe Ala Gln Ile Ile Ile Ile Val Val Val Thr Val Met Val Val
65                  70                  75                  80

Val Ile Val Cys Leu Leu Asn His Tyr Lys Val Ser Thr Arg Ser Phe
                85                  90                  95

Ile Asn Arg Pro Asn Gln Ser Arg Arg Arg Glu Asp Gly Leu Pro Gln
            100                 105                 110

Ile Met His Ala Pro Arg Ser Arg Asp Arg Phe Thr Ala Pro Ser Phe
            115                 120                 125

Ile Gln Arg Asp Arg Phe Ser Arg Phe Gln Pro Thr Tyr Pro Tyr Val
            130                 135                 140

Gln His Glu Ile Asp Leu Pro Pro Thr Ile Ser Leu Ser Asp Gly Glu
145                 150                 155                 160

Glu Pro Pro Pro Tyr Gln Gly Pro Cys Thr Leu Gln Leu Arg Asp Pro
                165                 170                 175

Glu Gln Gln Met Glu Leu Asn Arg Glu Ser Val Arg Ala Pro Pro Asn
            180                 185                 190

Arg Thr Ile Phe Asp Ser Asp Leu Ile Asp Ile Ala Met Tyr Ser Gly
            195                 200                 205

Gly Pro Cys Pro Pro Ser Ser Asn Ser Gly Ile Ser Ala Ser Thr Cys
            210                 215                 220

Ser Ser Asn Gly Arg Met Glu Gly Pro Pro Thr Tyr Ser Glu Val
225                 230                 235                 240

Met Gly His His Pro Gly Ala Ser Phe Leu His His Gln Arg Ser Asn
                245                 250                 255

Ala His Arg Gly Ser Arg Leu Gln Phe Gln Gln Asn Asn Ala Glu Ser
            260                 265                 270
```

```
Thr Ile Val Pro Ile Lys Gly Lys Asp Arg Lys Pro Gly Asn Leu Val
    275                 280                 285
```

(2) INFORMATION FOR SEQ ID NO: 5:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (ix) FEATURE:
        (A) NAME/KEY: -
        (B) LOCATION: 1...18
        (D) OTHER INFORMATION: alternatively spliced portion
            lacking from isoform 2

(xi) SEQUENCE DESCRIPTION: SEQ ID NO: 5:

```
Glu Gly Cys Leu Trp Pro Ser Asp Ser Ala Ala Pro Arg Leu Gly Ala
 1               5                  10                  15

Ser Glu
```

(2) INFORMATION FOR SEQ ID NO: 6:

(i) SEQUENCE CHARACTERISTICS:
        (A) LENGTH: 8065 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1...8065
        (D) OTHER INFORMATION: Clone 22

(ix) FEATURE:
        (A) NAME/KEY: CDS
        (B) LOCATION: 116...1036
        (D) OTHER INFORMATION: Clone 22 coding region (ix) FEATURE:
        (A) NAME/KEY: misc_feature
        (B) LOCATION: 452...505
        (D) OTHER INFORMATION: alternatively spliced portion (ix) FEATURE:
        (A) NAME/KEY: misc_feature
        (B) LOCATION: 5595...5685
        (D) OTHER INFORMATION: amplified region for genotyping (xi) SEQUENCE DESCRIPTION: SEQ ID NO: 6:

```
CCCAGCAGAG CGATGGACTT GGACAGGCTA AGATGGAAGT GACCTGAGCC TCGCCCGGCG        60

GCTTCCTCGA CGGGACAGCG CAAGAGTTGG AGCACAGGCT TGTCCGGGGA GCAGTATGCC       120

GGAAGCTGGT TTTCAGGCCA CAAATGCTTT CACAGAGTGC AAATTCACCT GCACCAGTGG       180

TAAATGCTTG TATCTTGGTT CGCTGGTCTG TAACCAACAG AACGACTGTG GGACAACAG        240

TGACGAAGAG AACTGTCTCC TGGTGACCGA GCACCCGCCT CCGGGCATCT TCAACTCGGA       300

GCTGGAGTTC GCCCAAATCA TCATCATCGT CGTGGTGGTC ACGGTGATGG TGGTGGTCAT       360

CGTCTGCCTG CTGAACCACT ACAAAGTCTC CACGCGGTCC TTCATCAACC GCCCGAACCA       420

GAGCCGGAGG CGGGAGGACG GGCTGCCGCA GGAAGGGTGC CTGTGGCCTT CAGACAGCGC       480

CGCACCGCGG CTGGGCGCCT CGGAGATCAT GCATGCCCCG CGGTCCAGGG ACAGGTTCAC       540
```

```
AGCGCCGTCC TTCATCCAGA GGGATCGCTT CAGCCGCTTC CAGCCCACCT ACCCCTATGT    600

GCAGCACGAG ATTGATCTTC CTCCCACCAT CTCCCTGTCC GACGGTGAAG AGCCACCTCC    660

TTACCAGGGG CCCTGCACCC TGCAGCTCCG GGACCCTGAA CAGCAGATGG AACTCAACCG    720

AGAGTCCGTG AGGGCCCCAC CCAACCGAAC CATATTTGAC AGTGATTTAA TAGACATTGC    780

TATGTATAGC GGGGGTCCAT GCCCACCCAG CAGCAACTCG GCATCAGTG CAAGCACCTG    840

CAGCAGTAAC GGGAGGATGG AGGGGCCACC CCCCACATAC AGCGAGGTGA TGGGCCACCA    900

CCCAGGCGCC TCTTTCCTCC ATCACCAGCG CAGCAACGCA CACAGGGGCA GCAGACTGCA    960

GTTTCAGCAG AACAATGCAG AGAGCACAAT AGTACCCATC AAAGGCAAAG ATAGGAAGCC   1020

TGGGAACCTG GTCTGATTCC TTCCAACGTG CACTTCAGCT GGAGAAAGAA ACCAAGAAGG   1080

GAAGCGGCCG CTGGGCCCCT CCTGCGCACA GTGTTGTTCA GTTTCACATG GTACAAATAA   1140

GTAAAACCAA ATGAGCAAAC ACGGTCTTTG TTTCTGATTC CTTTTAGGGG AATTGCATGC   1200

AAACTAGACT GAAATGATAC AAACTTCCAT CTGGTCTGAC CGCAAACAGT GTTTATTTGG   1260

GGACAGGGGT TGGGATGGGG GTGTGGGCAG GGGAAAACAG AGAACGGGAT GCTTTGAAGA   1320

TACCATGAAA TAAAACCCAC AGAGGTATTT GATGTATTTA ATTGTGAAAG GAGACTTTGC   1380

AGATAAATGA GGCCAGAATG GCATGTTTTA TAATTAACTG AATAAAGAAG GAAGCATTAT   1440

TATATATTAT TGTGGGAAG AACCAGCCAG TTCGCTTTTT CTCCTAAGGT GTGGACTTTT   1500

ATTTTGTTTT AAAAATATGA ATCAAAATTC CTGTGTTGTG TGCCAAGGTA TAAAGTGGAG   1560

AAGTTAGATG AGTGCAAGGA GCTCCTTTGT GTTGTGATGA TGTGTTTTAA AAGTTGCACT   1620

ATCTTAATGT TGAAAATATT TACAAGGGAA CTGTTTTACG TGAAGTTCTG TATGTTGTCT   1680

TTTCACCTGT GGATTGTAAT CAGGCCCAAG GAATATCCTG GAGTGGTCCC CAGAAGCATC   1740

CAAGAAAAGA TATTTGGGGA CGTAGCCTAA CATTTTACCA ACTTACGTAA ATCAAAAAAA   1800

TCATTATTGT TGCAGGAGTT TGCATCAAAT AGCAGTGCAT CGCTGAAGCT TTTGGAGACT   1860

TTTGATGGA AGATAAGATA GGGAAGATTA AGTTCCAGCA TTTCTGACTT GTTATTTTGA   1920

GTTACTCTGC TACTCTTAGG CTGCATAGTT TATGAGAAAA TGAACACATG CATTTATGGA   1980

TCCAGTATCA TGCAGTGCTG CCCTCATCCT CCAGCAGTGC AATTTCTTCA GTAATTTAGA   2040

TTTTTTTCAC TATAGCATGA AATATATTCA AATACATACC TTATTTTATG CAATAAATTG   2100

TTTAAAATGC AAGGTGGTTA TTCTGCATAC TGTTGAAATA TGTGACTCCT CAGTATATTC   2160

CCATTGCCTC TCCCCCTTTC CTCGACAGCT TAGTTCAGTT CTGCAGGGCT GCTCAGTTCA   2220

CAGGAGGCTC CCAGCAGCCA CCCCACATCC AGCCTACACA GAACTTTCGT GTGGGAGTGG   2280

TGTGGGTGGT GGTTTTCTTA TGCTTTGGAA GCCCCTAGAA ATAATGACGG AAGAATGCCA   2340

TGTTGCTGAT CGTGGTAATA AGCCATTGTG GGTTATTGTA TGTCACTAGT ATTAGCATAG   2400

CATTCTTAAA GGAATGCAGT GTTCAAAACC TACCCAAATT CCCCGCAGGA TTTTACCAAA   2460

CCCTTCCCCA GGCCAGTTTT GTACTGAAGG CAAGAACTGG ACAGTCAGAG AACAGTGGAG   2520

GGGGCAAGTG ACTGAAGAGC ACCGGGTAAA AGCACAACA TGCAGTTAAA ATGCAAACTA   2580

GAAAACTAAT TTTAAATATT GTTAGTTTTA ATATTTCCTG ATATTTACAA ATATTCATTC   2640

TTATATACAA TGAAAAAAAT AACTTTCTTC TGCAGATGTA AGCACTGGCT TTTATAAGAG   2700

CAGCAGCCAA CACGTTTAGC AGACACTGCG CGTGGAGAAG GGCTTATCTG CAGTACACTC   2760

TGCCATGTGG AGGGTGGGCC TCTGTGGCCT CTTCACATAA CAAGATGAGC TGGAATGATG   2820

ATTCCATGAC TCCCACCTAT GCAGCCTTAA AGCCAAATCC GCGTGTGTGT GTTTGTGTCT   2880
```

```
GTCTGTGGGT CTCGAAGGTG ATCCGTCGGT GCGGTGGCTC TGTGCTGTAA CTGGAGAGAC    2940

TGTTCCAAAC CCCAAGAGTT GTCTGATCCT AGTCTGTTCC CTTCTGCTTC TTACCTCTGT    3000

AGATAGGTCA CTGGTTTTTG TTTGTTTGTT TTGAGGATTG GAATTTCCAT TACATTCATC    3060

CTTTGCACAC AGTAACATCC ACAGAACTAG TCCAACTCTT AAAAGGAGAG AGGAAAAACA    3120

CAGGCACCAG TTGTCAGCTC ATGCTTACAA CCTGTGTGGA AGTATATACA GTTGAGAGTC    3180

ACAGTGGAGG TTCTGAGACT GGATTCAGTC TTGTTCCAGT GACAGTTGGA AGGCCTCTGC    3240

TGGAGAGACA CCAGCTCTCA GGGCAGAGAT TGGCTTGGGG CCAGAAGGAC CCTCCCCAAC    3300

CCTGGAGACA CCCTGAAGGT TCACTGGCTC TCCAGATTAG CCTCTCTTCC TCTGTCAGGC    3360

AAAGATGAGG AGCCCGTGTT CCCATCGGGC CCTGCTGGCA GGGACTTGCA GTGGATTCTT    3420

GGTCAGGTGT GCCCACAGAT GCGGAGGCGA GGTGAGTGAT TCCATCATTT CAGTTCTCAC    3480

CTGCAGTTTT GGTGAAGCAG GAGATGCACC CCACAGCTCT AGCTCTCAAA TGGCTTCACA    3540

GTCCTTACTT CTCTACCTGC CTCAAGAAGG GGCTCAGAGC AGAGACTTGT GAATTCCTTA    3600

GTAACTGTGA GTATATGAAT GTGTTGCACA TGTCCACAGT ATTGGCGAGA TAATTACATA    3660

ATTCAGATAC CTTTAATCAT CTTTCAAGAA AGAGGCTCCT CCCATTCAAC CACCCTAGAG    3720

AACTGCCTTT GTTAAATAGT TATTTAAAGA CTCATACATA TCAAACCATG ACTTTGAAAG    3780

GTCTTCGAGG CTGGGCTCT GTAATGAATT AGTTTAAAAG CCAAGGTCAT AACATGAATT    3840

GATGGTCAAT TTCCCTTCAG CAGAAGGAAA AGGTGATTTA GATCAGTAGC TCTTTTGAAG    3900

GTTGTGGCTG ACCTGTTCAT ACCGTGTCGC CTCATGGCTA GTGTGGCGTT GAAAGAGTAG    3960

CGACTGGGAA GATACAACTT ACACAGTGGG GCCTATTGTT CTTTCAAGAA CCCTTTTTTT    4020

AGCTTATAGA ACCCATGGGT CCAGTTTAGT AACGAGTGAT TTAGGCAATC AATGATAGGT    4080

TTATAATCTT AGATTATTCC AGCAAAGTGT GGATTGCATT GTTAGGAAGA ACATTTGGTG    4140

GGAATGAACA CTCCTGGGCA TACCGCTGAC TTTTGTCCCT TGTTCCCGGT GTAGGAGACC    4200

CAAGGCATCT TGAATCCCAT CTATAAGAAC ACAATCTTCC AGCATACGTT GCTTTTTCA    4260

GAAACTCTAG CATTCTCTTT AAATACTGAC GCAATCCTTA ATGGAAAAGA GATTTCATGA    4320

AGCAAATTAT GTATTTCAAT AGTTCTTCTA TTTTTAGTGT CCAAAATTTA CTAATACAGA    4380

AGCTTGACAA GCATGTCCTC ACCCTCCCCA CCACATAAAC ACATGGACAC ACACCCAAGC    4440

CACAAGAAAT CCCAAGAGAG CAGAAGCGAA TTTTTAAAAG ATTTATCGTG AGGACTGCAT    4500

TTCCATTCAC TAATTTTGGC TCAAACTTAT GAGGCAGGAA ATAGGGGCCA ACAGTAAATG    4560

GGGGAGGCCT CCTGACACCA GCAGAGGAAT TTTGTACCCA GGCGAGGACT TCTTGAACTT    4620

CTGCGTATCT CCGTTTGATC TCTTTCACCT TTATTTCATC TTCATAAGAA TGAGAAAGGC    4680

TCAAAAGGAA GCACTTTTAG AAATCTTCTC TGACCTAGAA GAATCCATCC AAATCCCTGC    4740

CTTCCTCTCT GAACCAACAG TTCCCTTCTC TGACAGGGGG CCATCCTCTA TCTTCCACCA    4800

AGCGGCTCTT CCTTTTAGGA AGGCTCTGGT GCAGAGCACT TCAAATATGT CCTCAGGGAC    4860

GATACTGATT GCTAGTAGAG AGACACCCGG CACCCAGTCC GAAGCCCTCC CTCAAAGGAC    4920

CGGCTTATGG CGTTGGTCAC TGGCAGGCTC AGAGACATTC TACTGTGGGC GCAGGGAGCC    4980

CGGCCCCCCA TGCAGCCATG ACTGGATGCG CCCCATCTC GGGGGCTTGC TGCACTGCTT    5040

GTTTATTGAA TTTTGCTACT TAGAATGGCA ACATTAACTT TGTGTACCAT TCATTTTTA    5100

AAAATTTTCC AAAGCTCGGC AGTGTATGAA AGAAAAAACT GGGAAAGATA CTTGGTTTCT    5160

GTTAACTTTT GTGTTGCTTG CTTAAGTGAT TAAAGCCAGT GCTTGGAGCC AAGCCTTCAT    5220

GCCACGAACA TGCTCCACAG CCTGCCCTTT GCTCTCCTGC TCACACTGAC CAAGAATGCC    5280
```

```
GCGTGCTTGG CCTACTGAGG TGAAAGGACA ATTGAATGAC AGGTGGGCAA AGGGAGAACT    5340

TCCCCTTCTT GGTGCGAGGA AAGTCACAAA TTTAAAAATG TTGCTTCCAG CCCAGATCCT    5400

AAATGCTAGT TCTCAGCAGC TGCGTGGCTT ACCGTTCGCC ATTTCCACCA CCGCCAGCTG    5460

CCAGCACCGC TACAGATCAC AGAGATGTGA ACAGACAATG GAAAGCACTC TTAGCCTTGC    5520

AGTGGTCTAC ATTTTTTAGG AACCAATATT TCAGCATTCT TTATTACCCG GCACGCTGTG    5580

TCCTTTGCAG AGTTCAAGTT TATGTTACTG CCAGGGTCAG ACAGTCATTT GCTGCTGCTG    5640

CTGCTGCTGC TGCTGCTTCT CGAACTGGAT GCATTAGGAA GCTGCTGTCT GAGTGTAGGA    5700

ATGTCTTGCT AAGAAAGCAA TGTCTTCCTT CATCCTTTTC TTTCTTCCCT CTGCGTGTCC    5760

TTGTTTTTGT GTAATGCGGG AGAGGGTTAG AGCTATAGAG ATTATATATA CACTATCCGT    5820

GCACATTATA TATATGTAGA TATACCCCTA TCATGTCAGA GATCTGCATG TCAGTTTTTC    5880

AGCAACTAAG GTGCCTCATG TTCTGAGTTC AGCAGATATA GGAACCAAGC CGCCCCCTCC    5940

TGCACTTGAT GCTCCCACCT TTGTTGTGCC TCACTTAAAA TGGTGCTTTT TTCAGTTGTC    6000

TGTCTTTTCT TATGTTTTTA TTTGTAAGGT GCTGTATATA AGTTGAATAT ATTATGCACA    6060

TATCCTACCC AATGGGTAGA ACAAAAGTT GTTAATACTG TAATATAATG TATAGATGAT    6120

ACCAATTTTA ACAGAAATGG CATAGAATTT GTGAATGCCT ATGTGCTTTG TCCTCTTTTG    6180

TAAGGAAATT TGCAAATGGA TGCATACAGA TTAAAGTCTA TGTAGTTTAT TTTCCTATTA    6240

AATATCAATA TTATAACACA AGAGAAAGAA GTGTGAACAA ACAAGCAACA GTTTATGACC    6300

AGCGTATATA TAGCAATGGA AAGTTGCATC TTTGCTGTGA AAACACTTTA AAGAAAATAC    6360

TTTTTAAAAA ATCCCACAGC TTTTTGGTTG CCACTAGACG CTTCTTATTT TAATCATTTT    6420

AGTAATGCTC AGCTGGACCA GTGTTAGTTA TATTTGAGTC AGAAAAATGT TGTTTTTCAA    6480

CTTGCTTTAT AATCTCCTGC ATCTATCTCC TGCTGTAGCA TCAYGAAGGT GTCAGGCAAC    6540

AGTGAAAAGT GCACATTTTT GTTGTTGCAG AAACTGTGTC AGAGGAATAA GTAAATCAGC    6600

CTGCAGCAGA AGACTTTGTT CAGCTCCAGA GGCATCTGTG ACCGTCTGTG TCCAAGTCTC    6660

TCTGTGCCTT TTTCTTTTAC AAACTGAAGC TGTGGAGCCA ATGAAGTAAC AGTAGAGATT    6720

GTAGGGAAAG AATACCTCAG GAAAAACAAA TACACTTACA AGAAGACCCT GTTCTTAGAA    6780

AATGTGTTTA GTTATGGGTT AGCACTAGAA GAGACTTGGC TGTCAGCCAG CCAAGTGAAG    6840

GACCTCTCAT CCATTCCCAT TCATGTCCCA TCATAATACG GACMCAAAAA GCAAACTCGG    6900

TTTTGCCATC AGTTAGAAAT TACGTTTTGG ATTGTATATT GTTACATCTC TCTTCCAGCT    6960

TAGTTTTTAG TGTCTGATTG TGACCTCTGC ATTTATCTTC AAATACCCTA ATTTTAAAAC    7020

AAAAGAACAA GAAAAGTTTA TAACACCATG TTCACTAAAA CCACGGTTGA ATCTTGGGTG    7080

TGGGCATCCT TTCGAGTGTT GTCCATAAGA GCAGTTCGTG GAATTTTGCC CATCTGACCC    7140

ATATTATCAG CTTATTCTGC CACCAGAGTA GAGTCTAATA AATTCCAAAG TTTTTATTTC    7200

CTCCATGGTG TATGTTCTGA CTTTGAAAAT GTCAGATTCT ATAATCATAC CCCTAACATC    7260

CAGGAGACAA ATGACAGATT ATCTTTAAAC TGAAATTGAC TCTACAATGC AACCCTTATT    7320

GCTGAATGGA TTAAAAAAGT CAGCCCTTTT AGTATCTGTT TGAAAGGGCC GTAAAAAGTT    7380

GACACTTTTG TTGTTGTGGA TCCTGCGTGT CTAGACCCAC GTGTTGTTTC CATCGTATAC    7440

TGTAGGGTGC ACCCCTTGGG ATTCATCATT AAGAACTGAG GCTCACTGTT GTCAGAAACA    7500

AAGCTCCCAC CCCCCAGGTT CAACCTTGTG GGAGAACTGT TGAGCATGAG AATGTTCTAG    7560

ACTCAGAGGT ACTAAAATTT GTTACCACAT CATTGCTTCC TTTCTACAGG ACGAATTGAG    7620
```

```
GCTTAAACTT TACTGTTAAT GATACTGGTT CATTTTAATG TGCTTGTTGG TATGTTGCTA    7680

TTTTTCATTT CATAGCTTTC AAAAATCATG CTAATTGTAT ACTTGTCTAN TTTAAGGCTA    7740

TTTTAAAATA TGTACAATAC TATTCACAGC ATTTAGTTCG TTTAATTTTT ATTATAAAGC    7800

AATCTACTAA AAAAGTACAA CTGTATTTGA ACTTTTCAAT AGTTGTTTGT GAGCTATGAT    7860

AATCAAAAGT CATTAAAGTC TTTTTTAACA AACATTCGTG CTTACTTTTC AACATAATTC    7920

CCAGTTATAT ACAGAAAAAG ATTTCCACCT GTCACGTATC TGCCTCTTTT ACCTGAGCAA    7980

TGGTGTAGTT CTTANACCTA AGGTCTGTAA TTGCAATACT TTTAAAGAAA GAGTTGCTCT    8040

AAGTGCTGTT TGTTAGTTAT GAAAC                                         8065

(2) INFORMATION FOR SEQ ID NO: 7:

(i) SEQUENCE CHARACTERISTICS:
        (A) LENGTH: 921 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1...921
        (D) OTHER INFORMATION: Clone 22 coding region (xi) SEQUENCE DESCRIPTION: SEQ ID NO: 7:

ATGCCGGAAG CTGGTTTTCA GGCCACAAAT GCTTTCACAG AGTGCAAATT CACCTGCACC      60

AGTGGTAAAT GCTTGTATCT TGGTTCGCTG GTCTGTAACC AACAGAACGA CTGTGGGGAC     120

AACAGTGACG AAGAGAACTG TCTCCTGGTG ACCGAGCACC CGCCTCCGGG CATCTTCAAC     180

TCGGAGCTGG AGTTCGCCCA AATCATCATC ATCGTCGTGG TGGTCACGGT GATGGTGGTG     240

GTCATCGTCT GCCTGCTGAA CCACTACAAA GTCTCCACGG GTCCTTCAT CAACCGCCCG      300

AACCAGAGCC GGAGGCGGGA GGACGGGCTG CCGCAGGAAG GGTGCCTGTG GCCTTCAGAC     360

AGCGCCGCAC CGCGGCTGGG CGCCTCGGAG ATCATGCATG CCCCGCGGTC CAGGGACAGG     420

TTCACAGCGC CGTCCTTCAT CCAGAGGGAT CGCTTCAGCC GCTTCCAGCC CACCTACCCC     480

TATGTGCAGC ACGAGATTGA TCTTCCTCCC ACCATCTCCC TGTCCGACGG TGAAGAGCCA     540

CCTCCTTACC AGGGGCCCTG CACCCTGCAG CTCCGGGACC CTGAACAGCA GATGGAACTC     600

AACCGAGAGT CCGTGAGGGC CCCACCCAAC CGAACCATAT TTGACAGTGA TTTAATAGAC     660

ATTGCTATGT ATAGCGGGGG TCCATGCCCA CCCAGCAGCA ACTCGGGCAT CAGTGCAAGC     720

ACCTGCAGCA GTAACGGGAG GATGGAGGGG CCACCCCCCA CATACAGCGA GGTGATGGGC     780

CACCACCCAG GCGCCTCTTT CCTCCATCAC CAGCGCAGCA ACGCACACAG GGGCAGCAGA     840

CTGCAGTTTC AGCAGAACAA TGCAGAGAGC ACAATAGTAC CCATCAAAGG CAAAGATAGG     900

AAGCCTGGGA ACCTGGTCTG A                                              921

(2) INFORMATION FOR SEQ ID NO: 8:

(i) SEQUENCE CHARACTERISTICS:
        (A) LENGTH: 867 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
```

(B) LOCATION: 1...867
      (D) OTHER INFORMATION: Clone 22 isoform 2 alternatively
          spliced coding region (xi) SEQUENCE DESCRIPTION: SEQ ID NO: 8:

ATGCCGGAAG CTGGTTTTCA GGCCACAAAT GCTTTCACAG AGTGCAAATT CACCTGCACC      60

AGTGGTAAAT GCTTGTATCT TGGTTCGCTG GTCTGTAACC AACAGAACGA CTGTGGGGAC     120

AACAGTGACG AAGAGAACTG TCTCCTGGTG ACCGAGCACC CGCCTCCGGG CATCTTCAAC     180

TCGGAGCTGG AGTTCGCCCA AATCATCATC ATCGTCGTGG TGGTCACGGT GATGGTGGTG     240

GTCATCGTCT GCCTGCTGAA CCACTACAAA GTCTCCACGC GGTCCTTCAT CAACCGCCCG     300

AACCAGAGCC GGAGGCGGGA GGACGGGCTG CCGCAGATCA TGCATGCCCC GCGGTCCAGG     360

GACAGGTTCA CAGCGCCGTC CTTCATCCAG AGGGATCGCT TCAGCCGCTT CCAGCCCACC     420

TACCCCTATG TGCAGCACGA GATTGATCTT CCTCCCACCA TCTCCCTGTC CGACGGTGAA     480

GAGCCACCTC CTTACCAGGG GCCCTGCACC CTGCAGCTCC GGGACCCTGA ACAGCAGATG     540

GAACTCAACC GAGAGTCCGT GAGGGCCCCA CCCAACCGAA CCATATTTGA CAGTGATTTA     600

ATAGACATTG CTATGTATAG CGGGGGTCCA TGCCCACCCA GCAGCAACTC GGGCATCAGT     660

GCAAGCACCT GCAGCAGTAA CGGGAGGATG GAGGGGCCAC CCCCCACATA CAGCGAGGTG     720

ATGGGCCACC ACCCAGGCGC CTCTTTCCTC CATCACCAGC GCAGCAACGC ACACAGGGGC     780

AGCAGACTGC AGTTTCAGCA GAACAATGCA GAGAGCACAA TAGTACCCAT CAAAGGCAAA     840

GATAGGAAGC CTGGGAACCT GGTCTGA                                        867

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: primer A (xi) SEQUENCE DESCRIPTION: SEQ ID NO: 9:

ATGCCGGAAG CTGGTTTTCA GG                                              22

(2) INFORMATION FOR SEQ ID NO: 10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...23
        (D) OTHER INFORMATION: primer B (xi) SEQUENCE DESCRIPTION: SEQ ID NO: 10:

TCCAGCTGAA GTGCACGTTG GCT                                             23

(2) INFORMATION FOR SEQ ID NO: 11:

```
    (i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: -
        (B) LOCATION: 1...14
        (D) OTHER INFORMATION: Motif A (xi) SEQUENCE DESCRIPTION: SEQ ID NO: 11:

Trp Xaa Ile Asp Pro Ile Asp Gly Thr Xaa Xaa Phe Xaa His
 1               5                  10

(2) INFORMATION FOR SEQ ID NO: 12:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: 5'UTR
        (B) LOCATION: 1...44
        (D) OTHER INFORMATION: Clone 22 5' untranslated region (xi) SEQUENCE DESCRIPTION: SEQ ID NO: 12:

TGCGAGAGCC GGGCAGGTGG GCCGCGGATG CTCCCAGAGG CCGG          44

(2) INFORMATION FOR SEQ ID NO: 13:

(i) SEQUENCE CHARACTERISTICS:
        (A) LENGTH: 491 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: 5'UTR
        (B) LOCATION: 1...491
        (D) OTHER INFORMATION: Clone 22 5' untranslated region (xi) SEQUENCE DESCRIPTION: SEQ ID NO: 13:

ATTTGCAGTA GAGGTGGATA GAGATGGTGA GCAGCATTGA CTCTCAAAAA TAGGGTCCTA    60

TGGCTGGTAA GGAGGTTGGT GCCTTCTCGA AGGGCTAGTG CTGGGAAGCT TCCTTTTAAA   120

AACGGCCCTT TCTGCCGGTT TGGCTAGCCA AGAATGGCAT CCTCCTCTCT GTATCTTCCC   180

TGGAGCTTCA GGACTGAGTA TTGAATGACA GAGAAGGTTC TGCAAAGTCT GCACAGGGAG   240

ACTGCCATTG CATCAAGTCA TGTCTGCATT CTGTATATGC GGTTCAAGCT CTACGTTCGT   300

GACATCAAAC CTCCTGTTGG GCCATTTCCG AGAACTCCCA TCAGTTTCTG TATAGTGTAA   360

AAGTTTCAGA GGCGGAGGAC AGAGAGCTGC GGCTGGGACA AGGAGCACCC GCGTGCAGGT   420

GCGACCCTGC AGGATGCTGG CAGCGGCGTG GCCAGGGGCG CCCGTGTTCT GAGGGCCTGA   480

GGGCCAGCCC C                                                       491

(2) INFORMATION FOR SEQ ID NO: 14:

(i) SEQUENCE CHARACTERISTICS:
        (A) LENGTH: 94 base pairs
```

(B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1...94
        (D) OTHER INFORMATION: Clone 22 allele 1 polymorphic marker (ix) FEATURE:
        (A) NAME/KEY: repeat_region
        (B) LOCATION: 37...66
        (D) OTHER INFORMATION: Clone 22 allele 1 polymorphic repeat
            sequence (xi) SEQUENCE DESCRIPTION: SEQ ID NO: 14:

CAAGTTTATG TTACTGCCAG GGTCAGACAG TCATTTGCTG CTGCTGCTGC TGCTGCTGCT        60

GCTGCTTCTC GAACTGGATG CATTAGGAAG CTGC                                   94

(2) INFORMATION FOR SEQ ID NO: 15:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1...91
        (D) OTHER INFORMATION: Clone 22 allele 2 polymorphic marker (ix) FEATURE:
        (A) NAME/KEY: repeat_region
        (B) LOCATION: 37...63
        (D) OTHER INFORMATION: Clone 22 allele 2 polymorphic repeat
            sequence (xi) SEQUENCE DESCRIPTION: SEQ ID NO: 15:

CAAGTTTATG TTACTGCCAG GGTCAGACAG TCATTTGCTG CTGCTGCTGC TGCTGCTGCT        60

GCTTCTCGAA CTGGATGCAT TAGGAAGCTG C                                      91

(2) INFORMATION FOR SEQ ID NO: 16:

(i) SEQUENCE CHARACTERISTICS:
        (A) LENGTH: 1447 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 142...1008
        (D) OTHER INFORMATION: IMP.18p myo-inositol monophosphatase (xi) SEQUENCE DESCRIPTION: SEQ ID NO: 16:

GTGGGACGGG CGGCGGACTA GGCACAGAGC TGCGGGAGCA GGCACAGGGA GTGTGGAGCC        60

TGGCGGCGGG ACGGCGGGAT CCGGTGGGAG CCGGAGTCCC GCCGAGGGGG GCTGGAGGTG       120

GAGGGGCCCG GCGAGGCCGC G ATG AAG CCG AGC GGC GAG GAC CAG GCG GCG        171
                        Met Lys Pro Ser Gly Glu Asp Gln Ala Ala
                          1               5                  10

CTG GCG GCC GGC CCC TGG GAG GAG TGC TTC CAG GCG GCC GTG CAG CTG        219
Leu Ala Ala Gly Pro Trp Glu Glu Cys Phe Gln Ala Ala Val Gln Leu

-continued

```
                  15                  20                  25
GCG CTG CGG GCA GGA CAG ATC ATC AGA AAA GCC CTT ACT GAG GAA AAA      267
Ala Leu Arg Ala Gly Gln Ile Ile Arg Lys Ala Leu Thr Glu Glu Lys
            30                  35                  40

CGT GTC TCA ACA AAA ACA TCA GCT GCA GAT CTT GTG ACA GAA ACA GAT      315
Arg Val Ser Thr Lys Thr Ser Ala Ala Asp Leu Val Thr Glu Thr Asp
            45                  50                  55

CAC CTT GTG GAA GAT TTA ATT ATT TCT GAG TTG CGA GAG AGG TTT CCT      363
His Leu Val Glu Asp Leu Ile Ile Ser Glu Leu Arg Glu Arg Phe Pro
            60                  65                  70

TCA CAC AGG TTC ATT GCA GAA GAG GCC GCG GCT TCT GGG GCC AAG TGT      411
Ser His Arg Phe Ile Ala Glu Glu Ala Ala Ala Ser Gly Ala Lys Cys
75                  80                  85                  90

GTG CTC ACC CAC AGC CCG ACG TGG ATC ATC GAC CCC ATC GAC GGC ACC      459
Val Leu Thr His Ser Pro Thr Trp Ile Ile Asp Pro Ile Asp Gly Thr
                95                  100                 105

TGC AAT TTT GTG CAC AGA TTC CCG ACT GTG GCG GTT AGC ATT GGA TTT      507
Cys Asn Phe Val His Arg Phe Pro Thr Val Ala Val Ser Ile Gly Phe
            110                 115                 120

GCT GTT CGA CAA GAG CTT GAA TTC GGA GTG ATT TAC CAC TGC ACA GAG      555
Ala Val Arg Gln Glu Leu Glu Phe Gly Val Ile Tyr His Cys Thr Glu
            125                 130                 135

GAG CGG CTG TAC ACG GGC CGG CGG GGT CGG GGC GCC TTC TGC AAT GGC      603
Glu Arg Leu Tyr Thr Gly Arg Arg Gly Arg Gly Ala Phe Cys Asn Gly
140                 145                 150

CAG CGG CTC CGG GTC TCC GGG GAG ACA GAT CTC TCA AAG GCC TTG GTT      651
Gln Arg Leu Arg Val Ser Gly Glu Thr Asp Leu Ser Lys Ala Leu Val
155                 160                 165                 170

CTG ACA GAA ATT GGC CCC AAA CGT GAC CCT GCG ACC CTG AAG CTG TTC      699
Leu Thr Glu Ile Gly Pro Lys Arg Asp Pro Ala Thr Leu Lys Leu Phe
                175                 180                 185

CTG AGT AAC ATG GAG CGG CTG CTG CAT GCC AAG GCG CAT GGG GTC CGA      747
Leu Ser Asn Met Glu Arg Leu Leu His Ala Lys Ala His Gly Val Arg
            190                 195                 200

GTG ATT GGA AGC TCC ACA TTG GCA CTC TGC CAC CTG GCC TCA GGG GCC      795
Val Ile Gly Ser Ser Thr Leu Ala Leu Cys His Leu Ala Ser Gly Ala
            205                 210                 215

GCG GAT GCC TAT TAC CAG TTT GGC CTG CAC TGC TGG GAT CTG GCG GCT      843
Ala Asp Ala Tyr Tyr Gln Phe Gly Leu His Cys Trp Asp Leu Ala Ala
    220                 225                 230

GCC ACA GTC ATC ATC AGA GAA GCA GGC GGC ATC GTG ATA GAC ACT TCG      891
Ala Thr Val Ile Ile Arg Glu Ala Gly Gly Ile Val Ile Asp Thr Ser
235                 240                 245                 250

GGT GGA CCC CTC GAC CTC ATG GCT TGC AGA GTG GTT GCG GCC AGC ACC      939
Gly Gly Pro Leu Asp Leu Met Ala Cys Arg Val Val Ala Ala Ser Thr
                255                 260                 265

CGG GAG ATG GCG ATG CTC ATA GCT CAG GCC TTA CAG ACC ATT AAC TAT      987
Arg Glu Met Ala Met Leu Ile Ala Gln Ala Leu Gln Thr Ile Asn Tyr
            270                 275                 280

GGG CGG GAT GAT GAG AAG TGACTGCGGC TGAGGCAAAG CTGCTCCCAA GGCCT      1043
Gly Arg Asp Asp Glu Lys
            285

TGGGCTGCTG TGGGCTCCTG GGGAGGTGGC CCTCGTGGCC CACGCTCCAT GCCAGTGGCT    1103

CACGCTCTGC TCCTGGCTAC CCCAGAGGGA GTTGTCACGC TACAGTGAGT GGCTGGCCTT    1163

TTAAATCGAC GTCTCTCTCA CCAGGATTTG GTGTTTAGCT GTTTCTCTCT TTAATCTCAC    1223

GTAGCCTTTT TCAGGTTAGT ACGTGTTCTT CTGTCAGGGC CAAAACTCAA ATCTCCTGTG    1283

AAATACGTAT TGATAATCCA ATCTTGATTT TTCCCCCCAG AATATAAATC TCAGGTAATA    1343
```

```
AGGCTTTAGA ACTGCTGATA AAGCGGATCG TTCTCAGGCC CTCCCCCCGG AGTACTTCAG      1403

AATGCAATAA ATCAAAATAA TGGGCAAAAA AAAAAAAAAA AAAA                       1447
```

(2) INFORMATION FOR SEQ ID NO: 17:

(i) SEQUENCE CHARACTERISTICS:
        (A) LENGTH: 288 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: mat_peptide
        (B) LOCATION: 1...288
        (D) OTHER INFORMATION: IMP.18p myo-inositol monophosphatase (xi) SEQUENCE DESCRIPTION: SEQ ID NO: 17:

```
Met Lys Pro Ser Gly Glu Asp Gln Ala Ala Leu Ala Ala Gly Pro Trp
 1               5                  10                  15

Glu Glu Cys Phe Gln Ala Ala Val Gln Leu Ala Leu Arg Ala Gly Gln
                20                  25                  30

Ile Ile Arg Lys Ala Leu Thr Glu Lys Arg Val Ser Thr Lys Thr
             35                  40                  45

Ser Ala Ala Asp Leu Val Thr Glu Thr Asp His Leu Val Glu Asp Leu
 50                  55                  60

Ile Ile Ser Glu Leu Arg Glu Arg Phe Pro Ser His Arg Phe Ile Ala
 65                  70                  75                  80

Glu Glu Ala Ala Ala Ser Gly Ala Lys Cys Val Leu Thr His Ser Pro
                 85                  90                  95

Thr Trp Ile Ile Asp Pro Ile Asp Gly Thr Cys Asn Phe Val His Arg
             100                 105                 110

Phe Pro Thr Val Ala Val Ser Ile Gly Phe Ala Val Arg Gln Glu Leu
            115                 120                 125

Glu Phe Gly Val Ile Tyr His Cys Thr Glu Glu Arg Leu Tyr Thr Gly
        130                 135                 140

Arg Arg Gly Arg Gly Ala Phe Cys Asn Gly Gln Arg Leu Arg Val Ser
145                 150                 155                 160

Gly Glu Thr Asp Leu Ser Lys Ala Leu Val Leu Thr Glu Ile Gly Pro
                165                 170                 175

Lys Arg Asp Pro Ala Thr Leu Lys Leu Phe Leu Ser Asn Met Glu Arg
            180                 185                 190

Leu Leu His Ala Lys Ala His Gly Val Arg Val Ile Gly Ser Ser Thr
        195                 200                 205

Leu Ala Leu Cys His Leu Ala Ser Gly Ala Ala Asp Ala Tyr Tyr Gln
    210                 215                 220

Phe Gly Leu His Cys Trp Asp Leu Ala Ala Ala Thr Val Ile Ile Arg
225                 230                 235                 240

Glu Ala Gly Gly Ile Val Ile Asp Thr Ser Gly Gly Pro Leu Asp Leu
                245                 250                 255

Met Ala Cys Arg Val Val Ala Ser Thr Arg Glu Met Ala Met Leu
                260                 265                 270

Ile Ala Gln Ala Leu Gln Thr Ile Asn Tyr Gly Arg Asp Asp Glu Lys
        275                 280                 285
```

(2) INFORMATION FOR SEQ ID NO: 18:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: forward primer (xi) SEQUENCE DESCRIPTION: SEQ ID NO: 18:

ATGAAGCCGA GCGGCGAGGA C                                              21

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: reverse primer (xi) SEQUENCE DESCRIPTION: SEQ ID NO: 19:

CTTCTCATCA TCCCGCCCAT AG                                             22

(2) INFORMATION FOR SEQ ID NO: 20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: forward primer (xi) SEQUENCE DESCRIPTION: SEQ ID NO: 20:

CTCGACCTCA TGGCTTGCAG AG                                             22

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: reverse primer (xi) SEQUENCE DESCRIPTION: SEQ ID NO: 21:

CTGAGAACGA TCCGCTTTAT C                                              21
```

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: forward primer (xi) SEQUENCE DESCRIPTION: SEQ ID NO: 22:

GTGTGTGCTC ACCCCGACTG T                                  21

(2) INFORMATION FOR SEQ ID NO: 23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: reverse primer (xi) SEQUENCE DESCRIPTION: SEQ ID NO: 23:

CCCGAAGTGT CTATCACGAT G                                  21

(2) INFORMATION FOR SEQ ID NO: 24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...29
        (D) OTHER INFORMATION: clone #39740 specific primer p1

(xi) SEQUENCE DESCRIPTION: SEQ ID NO: 24:

ACGTCGGGCT GTGGGTGAGC ACACACTTG                            29

(2) INFORMATION FOR SEQ ID NO: 25:

(i) SEQUENCE CHARACTERISTICS:
        (A) LENGTH: 285 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: mat_peptide
        (B) LOCATION: 1...285
        (D) OTHER INFORMATION: Xenopus IMP (xi) SEQUENCE DESCRIPTION: SEQ ID NO: 25:

Met Glu Asp Arg Trp Gln Glu Cys Met Asp Phe Leu Ala Val Ser Ile
1               5               10              15

```
Ala Arg Lys Ala Gly Ser Val Val Cys Ala Ala Leu Lys Glu Asp Val
            20                  25                  30

Ser Ile Met Val Lys Thr Ser Leu Ala Pro Ala Asp Leu Val Thr Ala
            35                  40                  45

Thr Asp Gln Lys Val Glu Glu Met Ile Ile Ser Ser Ile Lys Glu Lys
 50                      55                  60

Tyr Pro Ser His Ser Phe Ile Gly Glu Glu Ser Val Ala Ala Gly Ala
 65                  70                  75                  80

Gly Ser Thr Leu Thr Asp Asn Pro Thr Trp Ile Ile Asp Pro Ile Asp
                85                  90                  95

Gly Thr Thr Asn Phe Val His Arg Phe Pro Phe Val Ala Val Ser Ile
                100                 105                 110

Gly Phe Ala Val His Lys Gln Val Glu Phe Gly Val Val Tyr Ser Cys
            115                 120                 125

Val Glu Asp Lys Met Tyr Thr Gly Arg Lys Gly Lys Gly Ser Phe Cys
130                     135                 140

Asn Gly Gln Lys Leu Gln Val Ser Gly Gln Lys Asp Ile Thr Lys Ser
145                 150                 155                 160

Met Ile Ile Thr Glu Leu Gly Ser Asn Arg Asn Pro Glu Phe Ile Lys
                165                 170                 175

Thr Val Ser Leu Ser Asn Met Glu Arg Leu Leu Cys Ile Pro Ile His
                180                 185                 190

Gly Ile Arg Ala Val Gly Thr Ala Ala Val Asn Met Cys Leu Val Ala
            195                 200                 205

Thr Gly Gly Ala Asp Ala Tyr Tyr Glu Met Gly Leu His Cys Trp Asp
210                     215                 220

Met Ala Ala Ser Val Ile Val Thr Glu Ala Gly Gly Thr Ile Leu
225                 230                 235                 240

Asp Ala Thr Gly Gly Leu Phe Asp Leu Met Ser Cys Arg Ile Ile Ser
                245                 250                 255

Ala Ser Ser Arg Glu Ile Ala Glu Arg Ile Ala Lys Glu Leu Gln Ile
            260                 265                 270

Ile Pro Leu Glu Arg Asp Asp Gly Lys Ser Thr Asn Ser
            275                 280                 285

(2) INFORMATION FOR SEQ ID NO: 26:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: mat_peptide
        (B) LOCATION: 1...277
        (D) OTHER INFORMATION: rat IMP (xi) SEQUENCE DESCRIPTION: SEQ ID NO: 26:

Met Ala Asp Pro Trp Gln Glu Cys Met Asp Tyr Ala Val Thr Leu Ala
 1               5                  10                  15

Arg Gln Ala Gly Glu Val Val Cys Glu Ala Ile Lys Asn Glu Met Asn
            20                  25                  30

Val Met Leu Lys Ser Ser Pro Val Asp Leu Val Thr Ala Thr Asp Gln
            35                  40                  45
```

```
Lys Val Glu Lys Met Leu Ile Ser Ser Ile Lys Glu Lys Tyr Pro Ser
     50                  55                  60

His Ser Phe Ile Gly Glu Glu Ser Val Ala Ala Gly Glu Lys Ser Ile
 65                  70                  75                  80

Leu Thr Asp Asn Pro Thr Trp Ile Ile Asp Pro Ile Asp Gly Thr Thr
                 85                  90                  95

Asn Phe Val His Arg Phe Pro Val Ala Val Ser Ile Gly Phe Ala
                100                 105                 110

Val Asn Lys Lys Ile Glu Phe Gly Val Val Tyr Ser Cys Val Glu Gly
                115                 120                 125

Lys Met Tyr Thr Ala Arg Lys Gly Lys Gly Ala Phe Cys Asn Gly Gln
    130                 135                 140

Lys Leu Gln Val Ser Gln Gln Glu Asp Ile Thr Lys Ser Leu Leu Val
145                 150                 155                 160

Thr Glu Leu Gly Ser Ser Arg Thr Pro Glu Thr Val Arg Met Val Leu
                165                 170                 175

Ser Asn Met Glu Lys Leu Phe Cys Ile Pro Val His Gly Ile Arg Ser
                180                 185                 190

Val Gly Thr Ala Ala Val Asn Met Cys Leu Val Ala Thr Gly Gly Ala
            195                 200                 205

Asp Ala Tyr Tyr Glu Met Gly Ile His Cys Trp Asp Val Ala Gly Ala
    210                 215                 220

Gly Ile Ile Val Thr Glu Ala Gly Gly Val Leu Met Asp Val Thr Gly
225                 230                 235                 240

Gly Pro Phe Asp Leu Met Ser Arg Arg Val Ile Ala Ala Asn Asn Arg
                245                 250                 255

Ile Leu Ala Glu Arg Ile Ala Lys Glu Ile Gln Val Ile Pro Leu Gln
                260                 265                 270

Arg Asp Asp Glu Ser
                275

(2) INFORMATION FOR SEQ ID NO: 27:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: mat_peptide
        (B) LOCATION: 1...277
        (D) OTHER INFORMATION: bovine IMP (xi) SEQUENCE DESCRIPTION: SEQ ID NO: 27:

Met Ala Asp Pro Trp Gln Glu Cys Met Asp Tyr Ala Val Thr Leu Ala
 1               5                  10                  15

Gly Gln Ala Gly Glu Val Val Arg Glu Ala Leu Lys Asn Glu Met Asn
                 20                  25                  30

Ile Met Val Lys Ser Ser Pro Ala Asp Leu Val Thr Ala Thr Asp Gln
             35                  40                  45

Lys Val Glu Lys Met Leu Ile Thr Ser Ile Lys Glu Lys Tyr Pro Ser
     50                  55                  60

His Ser Phe Ile Gly Glu Glu Ser Val Ala Ala Gly Glu Lys Ser Ile
 65                  70                  75                  80

Leu Thr Asp Asn Pro Thr Trp Ile Ile Asp Pro Ile Asp Gly Thr Thr
```

```
                    85                  90                  95
Asn Phe Val His Gly Phe Pro Phe Val Ala Val Ser Ile Gly Phe Val
                100                 105                 110
Val Asn Lys Lys Met Glu Phe Gly Ile Val Tyr Ser Cys Leu Glu Asp
            115                 120                 125
Lys Met Tyr Thr Gly Arg Lys Gly Lys Gly Ala Phe Cys Asn Gly Gln
        130                 135                 140
Lys Leu Gln Val Ser His Gln Glu Asp Ile Thr Lys Ser Leu Leu Val
145                 150                 155                 160
Thr Glu Leu Gly Ser Ser Arg Thr Pro Glu Thr Val Arg Ile Ile Leu
                165                 170                 175
Ser Asn Ile Glu Arg Leu Leu Cys Leu Pro Ile His Gly Ile Arg Gly
            180                 185                 190
Val Gly Thr Ala Ala Leu Asn Met Cys Leu Val Ala Ala Gly Ala Ala
        195                 200                 205
Asp Ala Tyr Tyr Glu Met Gly Ile His Cys Trp Asp Val Ala Gly Ala
210                 215                 220
Gly Ile Ile Val Thr Glu Ala Gly Gly Val Leu Leu Asp Val Thr Gly
225                 230                 235                 240
Gly Pro Phe Asp Leu Met Ser Arg Arg Val Ile Ala Ser Ser Asn Lys
                245                 250                 255
Thr Leu Ala Glu Arg Ile Ala Lys Glu Ile Gln Ile Ile Pro Leu Gln
            260                 265                 270
Arg Asp Asp Glu Asp
        275

(2) INFORMATION FOR SEQ ID NO: 28:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: mat_peptide
        (B) LOCATION: 1...277
        (D) OTHER INFORMATION: human IMP (xi) SEQUENCE DESCRIPTION: SEQ ID NO: 28:

Met Ala Asp Pro Trp Gln Glu Cys Met Asp Tyr Ala Val Thr Leu Ala
1               5                   10                  15
Arg Gln Ala Gly Glu Val Val Cys Glu Ala Ile Lys Asn Glu Met Asn
            20                  25                  30
Val Met Leu Lys Ser Ser Pro Val Asp Leu Val Thr Ala Thr Asp Gln
        35                  40                  45
Lys Val Glu Lys Met Leu Ile Ser Ser Ile Lys Glu Lys Tyr Pro Ser
50                  55                  60
His Ser Phe Ile Gly Glu Glu Ser Val Ala Ala Gly Glu Lys Ser Ile
65                  70                  75                  80
Leu Thr Asp Asn Pro Thr Trp Ile Ile Asp Pro Ile Asp Gly Thr Thr
                85                  90                  95
Asn Phe Val His Arg Phe Pro Phe Val Ala Val Ser Ile Gly Phe Ala
                100                 105                 110
Val Asn Lys Lys Ile Glu Phe Gly Val Val Tyr Ser Cys Val Glu Gly
            115                 120                 125
```

```
Lys Met Tyr Thr Ala Arg Lys Gly Lys Gly Ala Phe Cys Asn Gly Gln
    130                 135                 140

Lys Leu Gln Val Ser Gln Gln Glu Asp Ile Thr Lys Ser Leu Leu Val
145                 150                 155                 160

Thr Glu Leu Gly Ser Ser Arg Thr Pro Glu Thr Val Arg Met Val Leu
                165                 170                 175

Ser Asn Met Glu Lys Leu Phe Cys Ile Pro Val His Gly Ile Arg Ser
            180                 185                 190

Val Gly Thr Ala Ala Val Asn Met Cys Leu Val Ala Thr Gly Gly Ala
        195                 200                 205

Asp Ala Tyr Tyr Glu Met Gly Ile His Cys Trp Asp Val Ala Gly Ala
        210                 215                 220

Gly Ile Ile Val Thr Glu Ala Gly Gly Val Leu Met Asp Val Thr Gly
225                 230                 235                 240

Gly Pro Phe Asp Leu Met Ser Arg Arg Val Ile Ala Ala Asn Asn Arg
                245                 250                 255

Ile Leu Ala Glu Arg Ile Ala Lys Glu Ile Gln Val Ile Pro Leu Gln
            260                 265                 270

Arg Asp Asp Glu Asp
        275
```

(2) INFORMATION FOR SEQ ID NO: 29:

(i) SEQUENCE CHARACTERISTICS:
        (A) LENGTH: 1215 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1...1215
        (D) OTHER INFORMATION: IMP.18p promoter sequence (ix) FEATURE:
        (A) NAME/KEY: misc_feature
        (B) LOCATION: 1...1026
        (D) OTHER INFORMATION: 5' flanking region (ix) FEATURE:
        (A) NAME/KEY: misc_feature
        (B) LOCATION: 1027...1215
        (D) OTHER INFORMATION: upstream portion of exon 1

(ix) FEATURE:
        (A) NAME/KEY: misc_feature
        (B) LOCATION: 1027
        (D) OTHER INFORMATION: minor transcriptional start site (ix) FEATURE:
        (A) NAME/KEY: misc_feature
        (B) LOCATION: 1033
        (D) OTHER INFORMATION: major cap site (ix) FEATURE:
        (A) NAME/KEY: misc_feature
        (B) LOCATION: 1193...1195
        (D) OTHER INFORMATION: translational initiation codon (ix) FEATURE:
        (A) NAME/KEY: misc_feature
        (B) LOCATION: 1193...1215
        (D) OTHER INFORMATION: complementary sequence to
            IMP.18p-specific antisense
            oligonucleotide primer p (xi) SEQUENCE DESCRIPTION: SEQ ID NO: 29:

```
GTCCAGCCGC TGTCCTCGCA GTGTTTGGGG TTAGCGGAGG GAGAGCTTGT TTGCGACCAA      60

ACTTGCCGCG CGGGGCGGCC GCTTGCAGGA ACACTGCGGC CTTGTGCGCT CGGCGGTCTG     120

AGCTCCTGCG AGGCCGAGAA CGACGCCTAG CGCCCAGCGG CCTCCGCGAA CAAAAAGCGA     180

CCGGTCGGAA GGTGCTGGCC CAGCCGCCCC TGGCGCTCGA GCCCGAATCC GGCCACAGAC     240

CATGAAGGGA CGCCCGGCAC CACGTGCGCG GGGATCCGCG GACGGGACGC TCCCCGGCAC     300

CTCCGGGGCT GGGCCGGCAC CGCACGGTCC CACCCAGACA GTAGCTGCCC CGGGCCCCCA     360

AAACAGCCGT TCCTAGCTCC TCCCTCCCAG TTTCTGCGGT GGCCCAAGCC GCCCTCCGCG     420

CGCTTGACCC AGAACAGTAC GGAGTTCTGC ACGAGCCGGG GGTGGGGCCT GTCTCAGCGC     480

GCGGCGGTGG GGCGGGGCTT GGACACGGGC CCGGCTCAAC TTGAGGGAGG CGGGGCTCGA     540

GGCTCAGAGG AGTTGGAGCC CGCTCTGCGC GCTGCGGGAC GGGGCACGGC GGAGCAGGGT     600

TGGGTCCGCC TCGAGCGGGG AGGGTGATGC TGCACCACAG GGGCGGGGCT GGAGGTAAAG     660

CGCGGAGCGG AGAGGGACCA GGCTCGGCAC TGATTTGTGT TCAGGGCTAG CCCAGAGGGG     720

CGGGGCCAGG TACGGGCGC AGCCGGGAGC GGGAGGGGCG GTGCAGGACG GGGCCGGGCA     780

CGGCGCGGGA AGAGGCCAGG AGCAGCAACG GGTGCGGGGC GGGGCCGGGA GCGTCAAGGG     840

GCGGGGAAGA GGGGGGAATG GGCGGGGCCG AGCTCTGCGA GGGGCGAGGT GGGGAATGCA     900

GAGCGGGGCC GGACGCGGGA GCAGGGAGCT GGGCGGGGAG CGGGGCGGGG AGCTGGGCTG     960

GGCTCGGCAC GGGGCGGGGC GGAGGGTGGG GAGCGGAAAG CAGGACGCGC GGCTCCCGCG    1020

GCCCGCTGGC TGCCCTTCCC GCCAGCGCAG GTGTGGGACG GGCGGCGGAC TAGGCACAGA    1080

GCTGCGGGAG CAGGCACAGG GAGTGTGGAG CCTGGCGGCG GGACGGCGGG TCCGGTGGGA    1140

GCCGGAGTCC CGCCGAGGGG GGCTGGAGGT GGAGGGGCCC GGCGAGGCCG CGATGAAGCC    1200

GAGCGGCGAG GACCA                                                    1215
```

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 22 forward primer (xi) SEQUENCE DESCRIPTION: SEQ ID NO: 30:

```
TACAAAAGAG GACAAAGCAC                                                 20
```

(2) INFORMATION FOR SEQ ID NO: 31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...17
        (D) OTHER INFORMATION: D18S73 forward primer (xi) SEQUENCE DESCRIPTION: SEQ ID NO: 31:

TGCCACTGCA ACAATGC                                                                17

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 22 reverse primer (xi) SEQUENCE DESCRIPTION: SEQ ID NO: 32:

GGTGCCTGTA TATAAGTTGA                                                             20

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY:
        (B) LOCATION: 1...20
        (D) OTHER INFORMATION: D18S73 reverse primer (xi) SEQUENCE DESCRIPTION: SEQ ID NO: 33:

CCCAGCAATC AACCTTTAAG                                                             20

(2) INFORMATION FOR SEQ ID NO: 34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: Clone 24 forward primer (xi) SEQUENCE DESCRIPTION: SEQ ID NO: 34:

CTACAGAATA GAATACATGG CG                                                          22

(2) INFORMATION FOR SEQ ID NO: 35:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...23

```
        (D) OTHER INFORMATION: D18S869 forward primer (xi) SEQUENCE DESCRIPTION: SEQ ID NO: 35:

TGTTTATTTG TTTGACTCAA TGG                                          23

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: Clone 24 reverse primer (xi) SEQUENCE DESCRIPTION: SEQ ID NO: 36:

GAGCTCTGAA CTGTATTCAG A                                            21

(2) INFORMATION FOR SEQ ID NO: 37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: D18S869 reverse primer (xi) SEQUENCE DESCRIPTION: SEQ ID NO: 37:

GAGTGAATGC TGTACAAACA GC                                           22

(2) INFORMATION FOR SEQ ID NO: 38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...18
        (D) OTHER INFORMATION: Clone 29 forward primer (xi) SEQUENCE DESCRIPTION: SEQ ID NO: 38:

TCTCAGCTTA CTCAACCT                                                18

(2) INFORMATION FOR SEQ ID NO: 39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
```

(B) LOCATION: 1...23
            (D) OTHER INFORMATION: D18S996 forward primer (xi) SEQUENCE DESCRIPTION: SEQ ID NO: 39:

GATGGAAAGC CATTTTATTT TTC                                              23

(2) INFORMATION FOR SEQ ID NO: 40:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...19
            (D) OTHER INFORMATION: Clone 29 reverse primer (xi) SEQUENCE DESCRIPTION: SEQ ID NO: 40:

GATGAGGTGG AACAATCAC                                                   19

(2) INFORMATION FOR SEQ ID NO: 41:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...25
            (D) OTHER INFORMATION: D18S996 reverse primer (xi) SEQUENCE DESCRIPTION: SEQ ID NO: 41:

TCGTACTATG AAATTTTAA GCCTT                                             25

(2) INFORMATION FOR SEQ ID NO: 42:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...22
            (D) OTHER INFORMATION: GNAL (Clone 31) forward primer (xi) SEQUENCE DESCRIPTION: SEQ ID NO: 42:

GGTCTGTACA GTGTAATAAA CC                                               22

(2) INFORMATION FOR SEQ ID NO: 43:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:

```
        (A) NAME/KEY: -
        (B) LOCATION: 1...20
        (D) OTHER INFORMATION: FB14A10 forward primer (xi) SEQUENCE DESCRIPTION: SEQ ID NO: 43:

CCTTCCCCTC TATTCTCAAA                                            20

(2) INFORMATION FOR SEQ ID NO: 44:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: GNAL (Clone 31) reverse primer (xi) SEQUENCE DESCRIPTION: SEQ ID NO: 44:

CTACTGCAAA ATGTGTCCTG TC                                         22

(2) INFORMATION FOR SEQ ID NO: 45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: FB14A10 reverse primer (xi) SEQUENCE DESCRIPTION: SEQ ID NO: 45:

GAGCGAGACT GTCTCAAAAA                                            20

(2) INFORMATION FOR SEQ ID NO: 46:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: Clone 37 forward primer (xi) SEQUENCE DESCRIPTION: SEQ ID NO: 46:

CACATTAGCC AGTCTGATAA AG                                         22

(2) INFORMATION FOR SEQ ID NO: 47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA
```

```
    (ix) FEATURE:
         (A) NAME/KEY: -
         (B) LOCATION: 1...20
         (D) OTHER INFORMATION: GC32001 forward primer (xi) SEQUENCE DESCRIPTION: SEQ ID NO: 47:

GAGTTGTGGG GGGGAATAGT                                                      20

(2) INFORMATION FOR SEQ ID NO: 48:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1...20
         (D) OTHER INFORMATION: Clone 37 reverse primer (xi) SEQUENCE DESCRIPTION: SEQ ID NO: 48:

AAGTTACACA CAGTAGCTGA                                                      20

(2) INFORMATION FOR SEQ ID NO: 49:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1...23
         (D) OTHER INFORMATION: GC32001 reverse primer (xi) SEQUENCE DESCRIPTION: SEQ ID NO: 49:

ATACGGAGGT TGAACTAGGA AGG                                                  23

(2) INFORMATION FOR SEQ ID NO: 50:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1...25
         (D) OTHER INFORMATION: AFMa058yg5 forward primer (xi) SEQUENCE DESCRIPTION: SEQ ID NO: 50:

TAGATGCTAT ATTAGGCTGG GTCTC                                                25

(2) INFORMATION FOR SEQ ID NO: 51:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA
```

(ix) FEATURE:
            (A) NAME/KEY: -
            (B) LOCATION: 1...20
            (D) OTHER INFORMATION: GP4B15 forward primer (xi) SEQUENCE DESCRIPTION: SEQ ID NO: 51:

CGGTTCTGGA TTTATCAGTA                                                           20

(2) INFORMATION FOR SEQ ID NO: 52:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...22
            (D) OTHER INFORMATION: AFMa058yg5 reverse primer (xi) SEQUENCE DESCRIPTION: SEQ ID NO: 52:

GAACTTACAG CACTGGCTCT CC                                                        22

(2) INFORMATION FOR SEQ ID NO: 53:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...19
            (D) OTHER INFORMATION: GP4B15 reverse primer (xi) SEQUENCE DESCRIPTION: SEQ ID NO: 53:

AGGGTTGCAA TGAGCTGAG                                                            19

(2) INFORMATION FOR SEQ ID NO: 54:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...22
            (D) OTHER INFORMATION: AFMa152wg9 forward primer (xi) SEQUENCE DESCRIPTION: SEQ ID NO: 54:

AAGAACAAAA GGTCACCTGT CA                                                        22

(2) INFORMATION FOR SEQ ID NO: 55:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
              (A) NAME/KEY: -
              (B) LOCATION: 1...20
              (D) OTHER INFORMATION: IB-1114 forward primer (xi) SEQUENCE DESCRIPTION: SEQ ID NO: 55:

GCCACACACA AATTTTTCTC                                                   20

(2) INFORMATION FOR SEQ ID NO: 56:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...22
              (D) OTHER INFORMATION: AFMa152wg9 reverse primer (xi) SEQUENCE DESCRIPTION: SEQ ID NO: 56:

TGTCTCACCT CTGCTCACTC AT                                                22

(2) INFORMATION FOR SEQ ID NO: 57:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...20
              (D) OTHER INFORMATION: IB-1114 reverse primer (xi) SEQUENCE DESCRIPTION: SEQ ID NO: 57:

ACAGGGTGTA AGAGGAGAGG                                                   20

(2) INFORMATION FOR SEQ ID NO: 58:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...20
              (D) OTHER INFORMATION: CHLC.GGAA16G02 forward primer (xi) SEQUENCE DESCRIPTION: SEQ ID NO: 58:

ATGGAAGGAA AAACAGAGGG                                                   20

(2) INFORMATION FOR SEQ ID NO: 59:

(i) SEQUENCE CHARACTERISTICS:
              (A) LENGTH: 20 base pairs
              (B) TYPE: nucleic acid
              (C) STRANDEDNESS: single
              (D) TOPOLOGY: linear

```
    (ii) MOLECULE TYPE: DNA (ix) FEATURE:
         (A) NAME/KEY: -
         (B) LOCATION: 1...20
         (D) OTHER INFORMATION: NIB-1802 forward primer (xi) SEQUENCE DESCRIPTION: SEQ ID NO: 59:

CTGATCACAT TTCATACAGC                                                   20

(2) INFORMATION FOR SEQ ID NO: 60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1...20
         (D) OTHER INFORMATION: CHLC.GGAA16G02 reverse primer (xi) SEQUENCE DESCRIPTION: SEQ ID NO: 60:

GAACTCTTCA AGAGGGGAGC                                                   20

(2) INFORMATION FOR SEQ ID NO: 61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1...20
         (D) OTHER INFORMATION: NIB-1802 reverse primer (xi) SEQUENCE DESCRIPTION: SEQ ID NO: 61:

TGTATGTGGG CTTAACTGTT                                                   20

(2) INFORMATION FOR SEQ ID NO: 62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1...25
         (D) OTHER INFORMATION: D18S1114 forward primer (xi) SEQUENCE DESCRIPTION: SEQ ID NO: 62:

ATCAGTATAA TGATGGATGA ATCAC                                             25

(2) INFORMATION FOR SEQ ID NO: 63:

(i) SEQUENCE CHARACTERISTICS:
        (A) LENGTH: 24 base pairs
        (B) TYPE: nucleic acid
        (C) STRANDEDNESS: single
```

```
            (D) TOPOLOGY: linear (ii) MOLECULE TYPE: DNA (ix) FEATURE:
            (A) NAME/KEY: -
            (B) LOCATION: 1...24
            (D) OTHER INFORMATION: SGC-31363 forward primer (xi) SEQUENCE DESCRIPTION: SEQ ID NO: 63:

CTACTGGGAG GTAGGTAATC TCAG                                              24

(2) INFORMATION FOR SEQ ID NO: 64:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...17
            (D) OTHER INFORMATION: D18S1114 reverse primer (xi) SEQUENCE DESCRIPTION: SEQ ID NO: 64:

TGAGGCAAGA GGGTCAC                                                      17

(2) INFORMATION FOR SEQ ID NO: 65:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...20
            (D) OTHER INFORMATION: SGC-31363 reverse primer (xi) SEQUENCE DESCRIPTION: SEQ ID NO: 65:

GCAAAACCAA CCACATCAAA                                                   20

(2) INFORMATION FOR SEQ ID NO: 66:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...18
            (D) OTHER INFORMATION: D18S1116 forward primer (xi) SEQUENCE DESCRIPTION: SEQ ID NO: 66:

TCTGCCACTT TTTATGGG                                                     18

(2) INFORMATION FOR SEQ ID NO: 67:

(i) SEQUENCE CHARACTERISTICS:
            (A) LENGTH: 20 base pairs
            (B) TYPE: nucleic acid
```

```
          (C) STRANDEDNESS: single
          (D) TOPOLOGY: linear (ii) MOLECULE TYPE: DNA (ix) FEATURE:
          (A) NAME/KEY: -
          (B) LOCATION: 1...20
          (D) OTHER INFORMATION: SGC34207 forward primer (xi) SEQUENCE DESCRIPTION: SEQ ID NO: 67:

GATCCTGTTC TTTCAGCAGG                                              20

(2) INFORMATION FOR SEQ ID NO: 68:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...25
          (D) OTHER INFORMATION: D18S1116 reverse primer (xi) SEQUENCE DESCRIPTION: SEQ ID NO: 68:

CAATGTTTTA ACTTCTAGGA CAAAT                                        25

(2) INFORMATION FOR SEQ ID NO: 69:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...21
          (D) OTHER INFORMATION: SGC34207 reverse primer (xi) SEQUENCE DESCRIPTION: SEQ ID NO: 69:

TTTAACCAGC TGGAGTGAAG G                                            21

(2) INFORMATION FOR SEQ ID NO: 70:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...18
          (D) OTHER INFORMATION: D18S1150 forward primer (xi) SEQUENCE DESCRIPTION: SEQ ID NO: 70:

GGCACAGGAA ACGTGAAT                                                18

(2) INFORMATION FOR SEQ ID NO: 71:

(i) SEQUENCE CHARACTERISTICS:
          (A) LENGTH: 22 base pairs
```

```
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...22
            (D) OTHER INFORMATION: WI-11680 forward primer (xi) SEQUENCE DESCRIPTION: SEQ ID NO: 71:

ACAGATACTT TTCCACGCAA CA                                                22

(2) INFORMATION FOR SEQ ID NO: 72:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...16
            (D) OTHER INFORMATION: D18S1150 reverse primer (xi) SEQUENCE DESCRIPTION: SEQ ID NO: 72:

CACAAGGATG CCAGCC                                                       16

(2) INFORMATION FOR SEQ ID NO: 73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...21
            (D) OTHER INFORMATION: WI-11680 reverse primer (xi) SEQUENCE DESCRIPTION: SEQ ID NO: 73:

AAAAAGATGT ACGGTCTGGC C                                                 21

(2) INFORMATION FOR SEQ ID NO: 74:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...20
            (D) OTHER INFORMATION: D18S1153 forward primer (xi) SEQUENCE DESCRIPTION: SEQ ID NO: 74:

ATGGAGGCTC TGAGACCCTT                                                   20

(2) INFORMATION FOR SEQ ID NO: 75:

(i) SEQUENCE CHARACTERISTICS:
```

(A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...25
            (D) OTHER INFORMATION: WI-13171 forward primer (xi) SEQUENCE DESCRIPTION: SEQ ID NO: 75:

TTTTATTTGG ACAAGAGAAC TTGTG                                                         25

(2) INFORMATION FOR SEQ ID NO: 76:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...19
            (D) OTHER INFORMATION: D18S1153 reverse primer (xi) SEQUENCE DESCRIPTION: SEQ ID NO: 76:

CTTGCCTGAT GCCTGAAAT                                                                19

(2) INFORMATION FOR SEQ ID NO: 77:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...20
            (D) OTHER INFORMATION: WI-13171 reverse primer (xi) SEQUENCE DESCRIPTION: SEQ ID NO: 77:

ATGATCAGCT CTGAGGTGCA                                                               20

(2) INFORMATION FOR SEQ ID NO: 78:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...20
            (D) OTHER INFORMATION: D18S1158 forward primer (xi) SEQUENCE DESCRIPTION: SEQ ID NO: 78:

GCATCTATGC AGTGCCAAAT                                                               20

(2) INFORMATION FOR SEQ ID NO: 79:

```
    (i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...23
        (D) OTHER INFORMATION: WI-18080 forward primer (xi) SEQUENCE DESCRIPTION: SEQ ID NO: 79:

TGGCATAAAG TTTGCAAATA TCA                                            23

(2) INFORMATION FOR SEQ ID NO: 80:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...23
        (D) OTHER INFORMATION: D18S1158 reverse primer (xi) SEQUENCE DESCRIPTION: SEQ ID NO: 80:

TCATTAGCAA CAAGGATCTC C                                              21

(2) INFORMATION FOR SEQ ID NO: 81:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...25
        (D) OTHER INFORMATION: WI-18080 reverse primer (xi) SEQUENCE DESCRIPTION: SEQ ID NO: 81:

ATACACCAAA GGAGAAGGAT TAACA                                          25

(2) INFORMATION FOR SEQ ID NO: 82:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...24
        (D) OTHER INFORMATION: D18S1228 forward primer (xi) SEQUENCE DESCRIPTION: SEQ ID NO: 82:

AGACAGTTGA AAAGGACACA AATG                                           24

(2) INFORMATION FOR SEQ ID NO: 83:
```

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...22
            (D) OTHER INFORMATION: D18S1066 forward primer (xi) SEQUENCE DESCRIPTION: SEQ ID NO: 83:

TGCTGTTGCC TCTCAGCATC TC                                              22

(2) INFORMATION FOR SEQ ID NO: 84:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...20
            (D) OTHER INFORMATION: D18S1228 reverse primer (xi) SEQUENCE DESCRIPTION: SEQ ID NO: 84:

TGGTGATGGG ACTTTTCAAA                                                 20

(2) INFORMATION FOR SEQ ID NO: 85:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...23
            (D) OTHER INFORMATION: D18S1066 reverse primer (xi) SEQUENCE DESCRIPTION: SEQ ID NO: 85:

CACCTTTCAA GTGCTTGGCA GTC                                             23

(2) INFORMATION FOR SEQ ID NO: 86:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...19
            (D) OTHER INFORMATION: D18S378 forward primer (xi) SEQUENCE DESCRIPTION: SEQ ID NO: 86:

AGCCTGGGTG ACAGAGCAA                                                  19

(2) INFORMATION FOR SEQ ID NO: 87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S1215 forward primer (xi) SEQUENCE DESCRIPTION: SEQ ID NO: 87:

GTTTGCTGCA TCTCCCAATT                                20

(2) INFORMATION FOR SEQ ID NO: 88:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...19
        (D) OTHER INFORMATION: D18S378 reverse primer (xi) SEQUENCE DESCRIPTION: SEQ ID NO: 88:

ACAGGGAAAG CTGGGGGAT                                 19

(2) INFORMATION FOR SEQ ID NO: 89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S1215 reverse primer (xi) SEQUENCE DESCRIPTION: SEQ ID NO: 89:

GTGCCCACAT TGTTGTGAAG                                20

(2) INFORMATION FOR SEQ ID NO: 90:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: D18S40 forward primer (xi) SEQUENCE DESCRIPTION: SEQ ID NO: 90:

CAAGATAGAT GCATTTTCCA GT                            22

(2) INFORMATION FOR SEQ ID NO: 91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S1299 forward primer (xi) SEQUENCE DESCRIPTION: SEQ ID NO: 91:

TTTAAGCCTC AAGGGACCCT                                              20

(2) INFORMATION FOR SEQ ID NO: 92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S40 reverse primer (xi) SEQUENCE DESCRIPTION: SEQ ID NO: 92:

CATCCAAAGG GTGAATGTGT                                              20

(2) INFORMATION FOR SEQ ID NO: 93:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S1299 reverse primer (xi) SEQUENCE DESCRIPTION: SEQ ID NO: 93:

AGATTGAGGA CCAGGTGGTG                                              20

(2) INFORMATION FOR SEQ ID NO: 94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S464 forward primer (xi) SEQUENCE DESCRIPTION: SEQ ID NO: 94:

GCCAGACTTT GTGCCATTTC                                              20

(2) INFORMATION FOR SEQ ID NO: 95:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...25
        (D) OTHER INFORMATION: D18S1226 forward primer (xi) SEQUENCE DESCRIPTION: SEQ ID NO: 95:

CTCTTAAGTT GAGTGAAGTG GAAGC    25

(2) INFORMATION FOR SEQ ID NO: 96:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...23
        (D) OTHER INFORMATION: D18S464 reverse primer (xi) SEQUENCE DESCRIPTION: SEQ ID NO: 96:

TTTCCTGAAT CTCTTGTGGT TTG    23

(2) INFORMATION FOR SEQ ID NO: 97:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S1226 reverse primer (xi) SEQUENCE DESCRIPTION: SEQ ID NO: 97:

CGCAAAAGTC AGGAAAGAGG    20

(2) INFORMATION FOR SEQ ID NO: 98:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S482 forward primer (xi) SEQUENCE DESCRIPTION: SEQ ID NO: 98:

```
ATGAGTGAAT GCCAACTTCG                                                    20

(2) INFORMATION FOR SEQ ID NO: 99:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...25
        (D) OTHER INFORMATION: SHGC-32282 forward primer (xi) SEQUENCE DESCRIPTION: SEQ ID NO: 99:

TTACGCATTT TGTATCAGAC TTACA                                              25

(2) INFORMATION FOR SEQ ID NO: 100:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...19
        (D) OTHER INFORMATION: D18S482 reverse primer (xi) SEQUENCE DESCRIPTION: SEQ ID NO: 100:

CCTGGCTGAC AGAGTGAGT                                                     19

(2) INFORMATION FOR SEQ ID NO: 101:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...25
        (D) OTHER INFORMATION: SHGC-32282 reverse primer (xi) SEQUENCE DESCRIPTION: SEQ ID NO: 101:

GGTGGAGTAT CAGAAGTGAT TTTAG                                              25

(2) INFORMATION FOR SEQ ID NO: 102:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: D18S53 forward primer (xi) SEQUENCE DESCRIPTION: SEQ ID NO: 102:
```

```
GGTCACCTAC AACTTTGGAT G                                              21
```

(2) INFORMATION FOR SEQ ID NO: 103:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S1315 forward primer (xi) SEQUENCE DESCRIPTION: SEQ ID NO: 103:

```
TGGACTTCTA CCCCCATCTG                                                20
```

(2) INFORMATION FOR SEQ ID NO: 104:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...24
        (D) OTHER INFORMATION: D18S53 reverse primer (xi) SEQUENCE DESCRIPTION: SEQ ID NO: 104:

```
TGCATGTAAA TATCAGAGTC TGTT                                           24
```

(2) INFORMATION FOR SEQ ID NO: 105:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: D18S1315 reverse primer (xi) SEQUENCE DESCRIPTION: SEQ ID NO: 105:

```
TTTGAAACCT GGACACTTTG G                                              21
```

(2) INFORMATION FOR SEQ ID NO: 106:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...16
        (D) OTHER INFORMATION: D18S71 forward primer (xi) SEQUENCE DESCRIPTION: SEQ ID NO: 106:

ACCCGCTCAA AAGCCT                                                           16

(2) INFORMATION FOR SEQ ID NO: 107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: D18S843 forward primer (xi) SEQUENCE DESCRIPTION: SEQ ID NO: 107:

GTCCTCATCT GTAAAACGGG                                                       20

(2) INFORMATION FOR SEQ ID NO: 108:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...25
        (D) OTHER INFORMATION: D18S71 reverse primer (xi) SEQUENCE DESCRIPTION: SEQ ID NO: 108:

TTAATGGATT ATCAAGAGTG GTTCT                                                 25

(2) INFORMATION FOR SEQ ID NO: 109:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...24
        (D) OTHER INFORMATION: D18S843 reverse primer (xi) SEQUENCE DESCRIPTION: SEQ ID NO: 109:

CCACTAACTA GTTTGTGACT TTGG                                                  24

(2) INFORMATION FOR SEQ ID NO: 110:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...19
        (D) OTHER INFORMATION: Clone 1 forward primer (xi) SEQUENCE DESCRIPTION: SEQ ID NO: 110:

AGGAGTGGTG TACATTTCT                                                19

(2) INFORMATION FOR SEQ ID NO: 111:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...23
        (D) OTHER INFORMATION: Clone 1 reverse primer (xi) SEQUENCE DESCRIPTION: SEQ ID NO: 111:

ACCTGCAACA CATTAGAAAC                                               20

(2) INFORMATION FOR SEQ ID NO: 112:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...25
        (D) OTHER INFORMATION: Clone 2 forward primer (xi) SEQUENCE DESCRIPTION: SEQ ID NO: 112:

GGTTTCTTCA AAATTTTATT AACAA                                         25

(2) INFORMATION FOR SEQ ID NO: 113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 2 reverse primer (xi) SEQUENCE DESCRIPTION: SEQ ID NO: 113:

TCCTCCACTC ATCTGTTTCT                                               20

(2) INFORMATION FOR SEQ ID NO: 114:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...19

(D) OTHER INFORMATION: Clone 3 forward primer (xi) SEQUENCE DESCRIPTION: SEQ ID NO: 114:

CCTGACCTGA TCAAGTTTA                                                    19

(2) INFORMATION FOR SEQ ID NO: 115:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...18
            (D) OTHER INFORMATION: Clone 3 reverse primer (xi) SEQUENCE DESCRIPTION: SEQ ID NO: 115:

GGTAAAGGAA CAAGCTGC                                                     18

(2) INFORMATION FOR SEQ ID NO: 116:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...21
            (D) OTHER INFORMATION: Clone 4 forward primer (xi) SEQUENCE DESCRIPTION: SEQ ID NO: 116:

TGATCACACA GTCAGCACTG T                                                 21

(2) INFORMATION FOR SEQ ID NO: 117:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...21
            (D) OTHER INFORMATION: Clone 4 reverse primer (xi) SEQUENCE DESCRIPTION: SEQ ID NO: 117:

GGGCAGAAGT TTCCAATTAC C                                                 21

(2) INFORMATION FOR SEQ ID NO: 118:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -

(B) LOCATION: 1...23
          (D) OTHER INFORMATION: Clone 5 forward primer (xi) SEQUENCE DESCRIPTION: SEQ ID NO: 118:

TATTGAGACC TAAGTCAGCA TCC                                    23

(2) INFORMATION FOR SEQ ID NO: 119:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...21
          (D) OTHER INFORMATION: Clone 5 reverse primer (xi) SEQUENCE DESCRIPTION: SEQ ID NO: 119:

GACAGAAAGC AGGTTAGAGG T                                      21

(2) INFORMATION FOR SEQ ID NO: 120:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...22
          (D) OTHER INFORMATION: Clone 6 forward primer (xi) SEQUENCE DESCRIPTION: SEQ ID NO: 120:

GAAACTTTAC ATCAGGTGTC TC                                     22

(2) INFORMATION FOR SEQ ID NO: 121:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...19
          (D) OTHER INFORMATION: Clone 6 reverse primer (xi) SEQUENCE DESCRIPTION: SEQ ID NO: 121:

ATGGACTAGG AGTTTAAGC                                         19

(2) INFORMATION FOR SEQ ID NO: 122:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (ix) FEATURE:

```
            (A) NAME/KEY: -
            (B) LOCATION: 1...19
            (D) OTHER INFORMATION: Clone 7 forward primer (xi) SEQUENCE DESCRIPTION: SEQ ID NO: 122:

GGAACAGTGT ACACTTTCC                                                    19

(2) INFORMATION FOR SEQ ID NO: 123:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...22
            (D) OTHER INFORMATION: Clone 7 reverse primer (xi) SEQUENCE DESCRIPTION: SEQ ID NO: 123:

TATATAGCCT CGATGATGAG AG                                                22

(2) INFORMATION FOR SEQ ID NO: 124:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...22
            (D) OTHER INFORMATION: Clone 8 forward primer (xi) SEQUENCE DESCRIPTION: SEQ ID NO: 124:

CATGAGAGGA AGAGGTCTTT AT                                                22

(2) INFORMATION FOR SEQ ID NO: 125:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...19
            (D) OTHER INFORMATION: Clone 8 reverse primer (xi) SEQUENCE DESCRIPTION: SEQ ID NO: 125:

GGGTTATGTC TTAGTCGAG                                                    19

(2) INFORMATION FOR SEQ ID NO: 126:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA
```

```
    (ix) FEATURE:
         (A) NAME/KEY: -
         (B) LOCATION: 1...23
         (D) OTHER INFORMATION: Clone 9 forward primer (xi) SEQUENCE DESCRIPTION: SEQ ID NO: 126:

TCAGTAGAAA CTCAAGCTGC TTC                                                23

(2) INFORMATION FOR SEQ ID NO: 127:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1...20
         (D) OTHER INFORMATION: Clone 9 reverse primer (xi) SEQUENCE DESCRIPTION: SEQ ID NO: 127:

CTCCCTCTCA GTGTGAGGCT                                                    20

(2) INFORMATION FOR SEQ ID NO: 128:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1...20
         (D) OTHER INFORMATION: Clone 10 forward primer (xi) SEQUENCE DESCRIPTION: SEQ ID NO: 128:

CCTGACCTGA TCAAGTTTAA                                                    20

(2) INFORMATION FOR SEQ ID NO: 129:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1...19
         (D) OTHER INFORMATION: Clone 10 reverse primer (xi) SEQUENCE DESCRIPTION: SEQ ID NO: 129:

TGTACACCAC TCCTCATGT                                                     19

(2) INFORMATION FOR SEQ ID NO: 130:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA
```

```
        (ix) FEATURE:
              (A) NAME/KEY: -
              (B) LOCATION: 1...21
              (D) OTHER INFORMATION: Clone 11 forward primer (xi) SEQUENCE DESCRIPTION: SEQ ID NO: 130:

CGACGACTCA TACAACATAT C                                         21

(2) INFORMATION FOR SEQ ID NO: 131:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...19
              (D) OTHER INFORMATION: Clone 11 reverse primer (xi) SEQUENCE DESCRIPTION: SEQ ID NO: 131:

GGTTACAGCT GAAGTGTAT                                            19

(2) INFORMATION FOR SEQ ID NO: 132:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...20
              (D) OTHER INFORMATION: Clone 12 forward primer (xi) SEQUENCE DESCRIPTION: SEQ ID NO: 132:

TATTCAGGAA CAGTGTACAC                                           20

(2) INFORMATION FOR SEQ ID NO: 133:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...19
              (D) OTHER INFORMATION: Clone 12 reverse primer (xi) SEQUENCE DESCRIPTION: SEQ ID NO: 133:

TCGATGATGA GAGGGTTAC                                            19

(2) INFORMATION FOR SEQ ID NO: 134:

(i) SEQUENCE CHARACTERISTICS:
              (A) LENGTH: 22 base pairs
              (B) TYPE: nucleic acid
              (C) STRANDEDNESS: single
              (D) TOPOLOGY: linear
```

```
     (ii) MOLECULE TYPE: DNA (ix) FEATURE:
          (A) NAME/KEY: -
          (B) LOCATION: 1...22
          (D) OTHER INFORMATION: Clone 13 forward primer (xi) SEQUENCE DESCRIPTION: SEQ ID NO: 134:

GAACACTTAT CTCCTTCTTC AG                                                  22

(2) INFORMATION FOR SEQ ID NO: 135:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (ix) FEATURE:
          (A) NAME/KEY: -
          (B) LOCATION: 1...21
          (D) OTHER INFORMATION: Clone 13 reverse primer (xi) SEQUENCE DESCRIPTION: SEQ ID NO: 135:

TCCACTCCTT TCACCTCTTC T                                                   21

(2) INFORMATION FOR SEQ ID NO: 136:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (ix) FEATURE:
          (A) NAME/KEY: -
          (B) LOCATION: 1...20
          (D) OTHER INFORMATION: Clone 14 forward primer (xi) SEQUENCE DESCRIPTION: SEQ ID NO: 136:

AGACAAGAGC AAAACACAAC                                                     20

(2) INFORMATION FOR SEQ ID NO: 137:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (ix) FEATURE:
          (A) NAME/KEY: -
          (B) LOCATION: 1...19
          (D) OTHER INFORMATION: Clone 14 reverse primer (xi) SEQUENCE DESCRIPTION: SEQ ID NO: 137:

CTCTTTGCAG TTCAGTCTA                                                      19

(2) INFORMATION FOR SEQ ID NO: 138:

(i) SEQUENCE CHARACTERISTICS:
         (A) LENGTH: 22 base pairs
         (B) TYPE: nucleic acid
         (C) STRANDEDNESS: single
         (D) TOPOLOGY: linear
```

```
        (ii) MOLECULE TYPE: DNA (ix) FEATURE:
              (A) NAME/KEY: -
              (B) LOCATION: 1...22
              (D) OTHER INFORMATION: Clone 15 forward primer (ix) FEATURE:
              (A) NAME/KEY: modified_base
              (B) LOCATION: 4
              (D) OTHER INFORMATION: N = inosine (xi) SEQUENCE DESCRIPTION: SEQ ID NO: 138:

AGGNGAACCA TTTGACTGGT TT                                          22

(2) INFORMATION FOR SEQ ID NO: 139:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...20
              (D) OTHER INFORMATION: Clone 15 reverse primer (xi) SEQUENCE DESCRIPTION: SEQ ID NO: 139:

GCTTGTGTGT GGCTGTCCTT                                             20

(2) INFORMATION FOR SEQ ID NO: 140:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...25
              (D) OTHER INFORMATION: Clone 16 forward primer (xi) SEQUENCE DESCRIPTION: SEQ ID NO: 140:

GGCTAAACTT ACAGTATGTA AGGAG                                       25

(2) INFORMATION FOR SEQ ID NO: 141:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1...20
              (D) OTHER INFORMATION: Clone 16 reverse primer (xi) SEQUENCE DESCRIPTION: SEQ ID NO: 141:

CTGTAAGGAC AGACTACTCA                                             20

(2) INFORMATION FOR SEQ ID NO: 142:
```

```
       (i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: -
           (B) LOCATION: 1...17
           (D) OTHER INFORMATION: Clone 17 forward primer (xi) SEQUENCE DESCRIPTION: SEQ ID NO: 142:

CCAGGAGGTT CAGCGGT                                                            17

(2) INFORMATION FOR SEQ ID NO: 143:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: -
           (B) LOCATION: 1...20
           (D) OTHER INFORMATION: Clone 17 reverse primer (ix) FEATURE:
           (A) NAME/KEY: Modified Base
           (B) LOCATION: 14
           (D) OTHER INFORMATION: N = inosine (xi) SEQUENCE DESCRIPTION: SEQ ID NO: 143:

CGCAAAGCCA TGANAAACCG                                                         20

(2) INFORMATION FOR SEQ ID NO: 144:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: -
           (B) LOCATION: 1...21
           (D) OTHER INFORMATION: Clone 18 forward primer (xi) SEQUENCE DESCRIPTION: SEQ ID NO: 144:

TCAGGAACAG TGTACACTTT C                                                       21

(2) INFORMATION FOR SEQ ID NO: 145:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: -
           (B) LOCATION: 1...21
           (D) OTHER INFORMATION: Clone 18 reverse primer
```

(xi) SEQUENCE DESCRIPTION: SEQ ID NO: 145:

TGTGGGCTTA ATACCATGTC T                                          21

(2) INFORMATION FOR SEQ ID NO: 146:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...18
        (D) OTHER INFORMATION: Clone 19 forward primer (xi) SEQUENCE DESCRIPTION: SEQ ID NO: 146:

GGAATCTCTG TACTTGCT                                              18

(2) INFORMATION FOR SEQ ID NO: 147:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...19
        (D) OTHER INFORMATION: Clone 19 forward primer (xi) SEQUENCE DESCRIPTION: SEQ ID NO: 147:

GTGACACATT ACAAAGCCA                                             19

(2) INFORMATION FOR SEQ ID NO: 148:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 20 forward primer (xi) SEQUENCE DESCRIPTION: SEQ ID NO: 148:

TCAGTAGAAA CTCAAGCTGC                                            20

(2) INFORMATION FOR SEQ ID NO: 149:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...19
        (D) OTHER INFORMATION: Clone 20 reverse primer (xi) SEQUENCE DESCRIPTION: SEQ ID NO: 149:

CCTCTTCCTC TTAAAGTGT                                                              19

(2) INFORMATION FOR SEQ ID NO: 150:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 21 forward primer (xi) SEQUENCE DESCRIPTION: SEQ ID NO: 150:

TCACTTCAGA ATCACTACTC                                                             20

(2) INFORMATION FOR SEQ ID NO: 151:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 21 reverse primer (xi) SEQUENCE DESCRIPTION: SEQ ID NO: 151:

ACCCATCCTA TATGAAAAGC                                                             20

(2) INFORMATION FOR SEQ ID NO: 152:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 23 forward primer (xi) SEQUENCE DESCRIPTION: SEQ ID NO: 152:

GGGATCATAC TAAAGAGAAG                                                             20

(2) INFORMATION FOR SEQ ID NO: 153:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20

(D) OTHER INFORMATION: Clone 23 reverse primer (xi) SEQUENCE DESCRIPTION: SEQ ID NO: 153:

GGATAAACAG AGAGCTTGAT                                               20

(2) INFORMATION FOR SEQ ID NO: 154:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1...22
      (D) OTHER INFORMATION: Clone 25 forward primer (xi) SEQUENCE DESCRIPTION: SEQ ID NO: 154:

GTCAGTTACT CTATTTGCTG TG                                            22

(2) INFORMATION FOR SEQ ID NO: 155:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1...20
      (D) OTHER INFORMATION: Clone 25 reverse primer (xi) SEQUENCE DESCRIPTION: SEQ ID NO: 155:

AACCTGTGCT GTAAAGTTCA                                               20

(2) INFORMATION FOR SEQ ID NO: 156:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1...19
      (D) OTHER INFORMATION: Clone 26 forward primer (xi) SEQUENCE DESCRIPTION: SEQ ID NO: 156:

CTTAAGAGGA AGAGGCCAT                                                19

(2) INFORMATION FOR SEQ ID NO: 157:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -

```
        (B) LOCATION: 1...19
        (D) OTHER INFORMATION: Clone 26 reverse primer (xi) SEQUENCE DESCRIPTION: SEQ ID NO: 157:

CTCTCCCTCT CAGTGTGAG                                                19

(2) INFORMATION FOR SEQ ID NO: 158:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: Clone 27 forward primer (xi) SEQUENCE DESCRIPTION: SEQ ID NO: 158:

ACAATTAGGC ATTGTTGATG G                                             21

(2) INFORMATION FOR SEQ ID NO: 159:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: Clone 27 reverse primer (ix) FEATURE:
        (A) NAME/KEY: modified_base
        (B) LOCATION: 4
        (D) OTHER INFORMATION: N = inosine (xi) SEQUENCE DESCRIPTION: SEQ ID NO: 159:

CAGNTCTTGC ACATACAAGA CA                                            22

(2) INFORMATION FOR SEQ ID NO: 160:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 28 forward primer (xi) SEQUENCE DESCRIPTION: SEQ ID NO: 160:

ACCTTTGGCA AGGGGTATGA                                               20

(2) INFORMATION FOR SEQ ID NO: 161:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (ii) MOLECULE TYPE: DNA (ix) FEATURE:
            (A) NAME/KEY: -
            (B) LOCATION: 1...20
            (D) OTHER INFORMATION: Clone 28 reverse primer (xi) SEQUENCE DESCRIPTION: SEQ ID NO: 161:

TGTGAAGGCT GGGAAACACT                                                    20

(2) INFORMATION FOR SEQ ID NO: 162:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...19
            (D) OTHER INFORMATION: Clone 30 forward primer (xi) SEQUENCE DESCRIPTION: SEQ ID NO: 162:

AACACTCAGC TCTGTAGAA                                                     19

(2) INFORMATION FOR SEQ ID NO: 163:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...19
            (D) OTHER INFORMATION: Clone 30 reverse primer (xi) SEQUENCE DESCRIPTION: SEQ ID NO: 163:

CGAGTCATCA ATAGGACAA                                                     19

(2) INFORMATION FOR SEQ ID NO: 164:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...21
            (D) OTHER INFORMATION: Clone 32 forward primer (xi) SEQUENCE DESCRIPTION: SEQ ID NO: 164:

GAGCCAAGTG GAACTCTTGA A                                                  21

(2) INFORMATION FOR SEQ ID NO: 165:

(i) SEQUENCE CHARACTERISTICS:
            (A) LENGTH: 21 base pairs
            (B) TYPE: nucleic acid

```
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: Clone 32 reverse primer (xi) SEQUENCE DESCRIPTION: SEQ ID NO: 165:

GTCAGGAAAG AGGTTGTGAG C                                              21

(2) INFORMATION FOR SEQ ID NO: 166:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 33 forward primer (xi) SEQUENCE DESCRIPTION: SEQ ID NO: 166:

ACACATATGT ACACAGGAAC                                                20

(2) INFORMATION FOR SEQ ID NO: 167:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 33 reverse primer (xi) SEQUENCE DESCRIPTION: SEQ ID NO: 167:

TGTGTACAGC GAGTGAATTA                                                20

(2) INFORMATION FOR SEQ ID NO: 168:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 34 forward primer (xi) SEQUENCE DESCRIPTION: SEQ ID NO: 168:

TTGTTCACAC ACAATCTAGG                                                20

(2) INFORMATION FOR SEQ ID NO: 169:

(i) SEQUENCE CHARACTERISTICS:
        (A) LENGTH: 21 base pairs
```

```
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: Clone 34 reverse primer (xi) SEQUENCE DESCRIPTION: SEQ ID NO: 169:

ACTAGCATAT CTGAATTCCC A                                          21

(2) INFORMATION FOR SEQ ID NO: 170:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...22
        (D) OTHER INFORMATION: Clone 35 forward primer (xi) SEQUENCE DESCRIPTION: SEQ ID NO: 170:

CTACAGAATA GAATACATGG CG                                         22

(2) INFORMATION FOR SEQ ID NO: 171:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 35 reverse primer (xi) SEQUENCE DESCRIPTION: SEQ ID NO: 171:

TTGAAACCAG ACCCTGTAGT                                            20

(2) INFORMATION FOR SEQ ID NO: 172:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 36 forward primer (xi) SEQUENCE DESCRIPTION: SEQ ID NO: 172:

CATTTAGTCC AGAGGCTCTT                                            20

(2) INFORMATION FOR SEQ ID NO: 173:

(i) SEQUENCE CHARACTERISTICS:
```

(A) LENGTH: 19 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1...19
(D) OTHER INFORMATION: Clone 36 reverse primer (xi) SEQUENCE DESCRIPTION: SEQ ID NO: 173:

TCCTCGAAGA GGTTGCAGC                                19

(2) INFORMATION FOR SEQ ID NO: 174:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1...22
(D) OTHER INFORMATION: Clone 38 forward primer (xi) SEQUENCE DESCRIPTION: SEQ ID NO: 174:

CATTCAGCAC ACATAGAGTC TA                            22

(2) INFORMATION FOR SEQ ID NO: 175:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1...20
(D) OTHER INFORMATION: Clone 38 reverse primer (xi) SEQUENCE DESCRIPTION: SEQ ID NO: 175:

CCCTGTCCCT TGTATATGTA                               20

(2) INFORMATION FOR SEQ ID NO: 176:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1...24
(D) OTHER INFORMATION: Clone 39 forward primer (xi) SEQUENCE DESCRIPTION: SEQ ID NO: 176:

AGTGTATCTA CAACCTCAAC TGTC                          24

(2) INFORMATION FOR SEQ ID NO: 177:

```
        (i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...22
            (D) OTHER INFORMATION: Clone 39 reverse primer (xi) SEQUENCE DESCRIPTION: SEQ ID NO: 177:

GTAAAGGCCC AATCAATGCA CT                                              22

(2) INFORMATION FOR SEQ ID NO: 178:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...20
            (D) OTHER INFORMATION: Clone 40 forward primer (xi) SEQUENCE DESCRIPTION: SEQ ID NO: 178:

GCCAGATTCA CAATTGATAG                                                 20

(2) INFORMATION FOR SEQ ID NO: 179:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...19
            (D) OTHER INFORMATION: Clone 40 reverse primer (xi) SEQUENCE DESCRIPTION: SEQ ID NO: 179:

CTGAAGGCAC TTTATGTAC                                                  19

(2) INFORMATION FOR SEQ ID NO: 180:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1...21
            (D) OTHER INFORMATION: Clone 41 forward primer (xi) SEQUENCE DESCRIPTION: SEQ ID NO: 180:

CTGGAGCAGG TTAGATACAC C                                               21

(2) INFORMATION FOR SEQ ID NO: 181:
```

```
      (i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...22
          (D) OTHER INFORMATION: Clone 41 reverse primer (xi) SEQUENCE DESCRIPTION: SEQ ID NO: 181:

CTTCCCTCTT AACCTTTAGT GC                                              22

(2) INFORMATION FOR SEQ ID NO: 182:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...21
          (D) OTHER INFORMATION: Clone 42 forward primer (xi) SEQUENCE DESCRIPTION: SEQ ID NO: 182:

GTGTCTTGTA TGTGCAAGAA C                                               21

(2) INFORMATION FOR SEQ ID NO: 183:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...20
          (D) OTHER INFORMATION: Clone 42 reverse primer (xi) SEQUENCE DESCRIPTION: SEQ ID NO: 183:

GACTGGGTAT CCTAGCTTAC                                                 20

(2) INFORMATION FOR SEQ ID NO: 184:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1...20
          (D) OTHER INFORMATION: Clone 43 forward primer (xi) SEQUENCE DESCRIPTION: SEQ ID NO: 184:

TTAGTCAGAC CCATTCAGTC                                                 20
```

(2) INFORMATION FOR SEQ ID NO: 185:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 43 reverse primer (xi) SEQUENCE DESCRIPTION: SEQ ID NO: 185:

CCAGACTGCT TTATGTTAG                                                19

(2) INFORMATION FOR SEQ ID NO: 186:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...21
        (D) OTHER INFORMATION: Clone 44 forward primer (xi) SEQUENCE DESCRIPTION: SEQ ID NO: 186:

GTGTCTTGTA TGTGCAAGAA C                                             21

(2) INFORMATION FOR SEQ ID NO: 187:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 44 reverse primer (xi) SEQUENCE DESCRIPTION: SEQ ID NO: 187:

CCTAGCCTTA CTGTTTTAAC                                               20

(2) INFORMATION FOR SEQ ID NO: 188:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...18
        (D) OTHER INFORMATION: Clone 45 forward primer (xi) SEQUENCE DESCRIPTION: SEQ ID NO: 188:

ACGATGCGAT CCTGGAAG                                                 18

(2) INFORMATION FOR SEQ ID NO: 189:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...18
        (D) OTHER INFORMATION: Clone 45 reverse primer (xi) SEQUENCE DESCRIPTION: SEQ ID NO: 189:

CTGGCTTGAG TTTGTCTG                                                        18

(2) INFORMATION FOR SEQ ID NO: 190:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 46 forward primer (xi) SEQUENCE DESCRIPTION: SEQ ID NO: 190:

CCTTTCTGTG TGAAGATCAC                                               20

(2) INFORMATION FOR SEQ ID NO: 191:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 46 reverse primer (xi) SEQUENCE DESCRIPTION: SEQ ID NO: 191:

AAGAAAGTCC CAAGGGTGGA                                               20

(2) INFORMATION FOR SEQ ID NO: 192:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...19
        (D) OTHER INFORMATION: Clone 47 forward primer (xi) SEQUENCE DESCRIPTION: SEQ ID NO: 192:

GGAATGAGGG TTAGAGTCC                                                   19

(2) INFORMATION FOR SEQ ID NO: 193:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...18
        (D) OTHER INFORMATION: Clone 47 reverse primer (xi) SEQUENCE DESCRIPTION: SEQ ID NO: 193:

AGTGCTTCTG TAGCTCTT                                        18

(2) INFORMATION FOR SEQ ID NO: 194:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 48 forward primer (xi) SEQUENCE DESCRIPTION: SEQ ID NO: 194:

TGAGGGTGTG AACCACTCTG                                   20

(2) INFORMATION FOR SEQ ID NO: 195:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...20
        (D) OTHER INFORMATION: Clone 48 reverse primer (xi) SEQUENCE DESCRIPTION: SEQ ID NO: 195:

GAATCCTGGT GTGCCCAAGT                                   20

(2) INFORMATION FOR SEQ ID NO: 196:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 13...14
        (D) OTHER INFORMATION: Xaa = Gly or Ala (xi) SEQUENCE DESCRIPTION: SEQ ID NO: 196:

-continued

```
Trp Asp Xaa Xaa Ala Ala Xaa Val Ile Xaa Xaa Xaa Xaa Xaa
 1               5                   10
```

(2) INFORMATION FOR SEQ ID NO: 197:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1...17
        (D) OTHER INFORMATION: primer used for primer
            extension analysis (xi) SEQUENCE DESCRIPTION: SEQ ID NO: 197:

GGGCGACCGA CGGGAAG                                    17